United States Patent [19]
Wong et al.

[11] Patent Number: 5,760,203
[45] Date of Patent: Jun. 2, 1998

[54] GAP GENE SEQUENCES

[75] Inventors: Gail L. Wong, Oakland; George Martin, Berkeley; Francis P. McCormick, Albany; Bonnee Rubinfeld, Danville; Edward C. O'Rourke; Robin Clark, both of Oakland, all of Calif.

[73] Assignee: Chiron Corporation, Emeryville, Calif.

[21] Appl. No.: 190,687

[22] Filed: Feb. 2, 1994

Related U.S. Application Data

[63] Continuation of Ser. No. 774,644, Oct. 11, 1991, abandoned, which is a continuation of Ser. No. 260,807, Oct. 21, 1988, abandoned, which is a continuation-in-part of Ser. No. 230,761, Aug. 10, 1988, abandoned.

[51] Int. Cl.⁶ .................................................. C07H 21/04
[52] U.S. Cl. .................... 536/23.1; 435/6; 435/69.1; 435/172.3; 435/240.1; 536/24.1; 536/24.3; 536/24.31; 536/24.32; 536/24.33; 935/9; 935/77; 935/78
[58] Field of Search .................... 435/6, 69.1, 240.1, 435/172.3, 810; 436/501, 63; 536/22.1, 23.1, 24.1, 24.3–24.33; 935/9, 77, 78

[56] References Cited

U.S. PATENT DOCUMENTS

| | | | |
|---|---|---|---|
| 4,518,584 | 5/1985 | Mark et al. | 424/85 |
| 4,542,092 | 9/1985 | Toya et al. | 430/510 |
| 4,588,585 | 5/1986 | Mark et al. | 424/85 |
| 4,683,195 | 7/1987 | Mullis et al. | 435/6 |
| 4,683,202 | 7/1987 | Mullis | 435/91 |
| 4,699,877 | 10/1987 | Cline et al. | 435/6 |
| 4,745,051 | 5/1988 | Smith et al. | 435/68 |
| 4,762,706 | 8/1988 | McCormick et al. | 424/85 |
| 4,800,159 | 1/1989 | Mullis et al. | 435/172.3 |
| 4,889,818 | 12/1989 | Gelfand et al. | 435/194 |
| 4,965,188 | 10/1990 | Mullis et al. | 435/6 |
| 5,024,947 | 6/1991 | Inlow et al. | 435/240.31 |
| 5,066,584 | 11/1991 | Gyllensten et al. | 435/91 |
| 5,104,975 | 4/1992 | McCormick et al. | 530/350 |
| 5,234,839 | 8/1993 | McCormick et al. | 436/501 |
| 5,372,943 | 12/1994 | Inlow et al. | 435/240.31 |

FOREIGN PATENT DOCUMENTS

| | | |
|---|---|---|
| 0 108 564 A1 | 5/1984 | European Pat. Off. . |
| 0 127 839 A2 | 12/1984 | European Pat. Off. . |
| 0 258 017 A2 | 3/1988 | European Pat. Off. . |
| WO 84/01389 | 4/1984 | WIPO . |
| WO 85/00974 | 3/1985 | WIPO . |
| WO 89/01027 | 2/1989 | WIPO . |
| WO 89/01029 | 2/1989 | WIPO . |

OTHER PUBLICATIONS

New England Biolabs Catalog [Published by New England Biolabs, Beverly, Massachusetts (1986/87)], pp. 60–62.

Grand et al., *Oncongene*, "Purification and characterisation of the protein encoded by the activated human N–ras gene and its membrane localisation," vol. 1, pp. 305–314, 1987.

Tamaoki et al., *Biochem. and Biophys. Res. Comm.*, "Expression of Intact Ki–ras p21 Protein in *Escherichia coli*", vol. 132, No. 1, pp. 126–133, Oct. 15, 1985.

Manne et al., Proc. Natl. Acad. Sci. USA, "Guanosine nucleotide binding by highly purified Ha–ras–encoded p21 protein produced in *Escherichia coli*", vol. 81, pp. 6953–6957, November 1984.

Lacal et al., *Proc. Natl. Acad. Sci. USA*, "Expression of normal and transforming H–ras–genes in *Escherichia coli* and purification of their encoded p21 proteins", vol. 81, pp. 5305–5309, September 1984.

(List continued on next page.)

*Primary Examiner*—Ardin H. Marschel
*Attorney, Agent, or Firm*—Marshall, O'Toole et al.; Jane E. R. Potter; Robert P. Blackburn

[57] ABSTRACT

Guanosine triphosphatase activating protein (GAP) DNA sequences are described that are useful as cancer diagnostics, particularly to detect cancer cells that express the ras oncogene protein p21 by measuring the level of GAP gene expression or amplification.

39 Claims, 10 Drawing Sheets

OTHER PUBLICATIONS

Papageorge et al., Journal of Virology, "Comparative Biochemical Properties of p21 ras Molecules Coded for by Viral and Cellular ras Genes", vol. 44, No. 2, pp. 509–519, November 1982.

McCormick, et al., 1988, Cold Spring Harbor Symposia on Quantitative Biology, LIII:849–854.

Adari, H., et al., 1988, Science, 240:518–521.

Sigal, I.S., 1988, Nature, 332:485–486.

McCormick, F., et al., 1988, CSH, (Abstract Only).

Trahey, M., et al., 1987, Meeting on Oncogenes NCI (Abstract Only).

Adari, et al., "Guanosine Triphosphatase Activating Protein (GAP) Interacts with the p21 ras Effector Binding Domain", Science 240:518–521 (Apr. 22, 1988).

Aviv, et al., "Purification of Biologically Active Globin Messenger RNA by Chromatography on Oligothymidylic acid–Cellulose", Proc. Natl. Acad. Sci. (U.S.A.) 69:1408–1412 (June 1972).

Barbacid, M., "ras GENES", Ann. Rev. Biochem. 56:779–827 (1987).

Barbacid, M., "Human Oncogenes", In Important Advances in Oncology (ed.s DeVita, B., Helman, S., Rosenberg, S.) Philadelphia:Lippincott, pp. 3–22 (1986).

Bos, et al., "Amino–acid substitutions at codon 13 of the N–ras oncogene in human acute myeloid leukaemia", Nature 315:726–730 (1985).

Burand, et al., "Transfection with Baculovirus DNA", Virology 101:286–290 (1980).

Burnette, "'Western Blotting': Electrophoretic Transfer of Proteins from Sodium Dodecyl Sulfate–Polyacrylamide Gels to Unmodified Nitrocellulose and Radiographic Detection with Antibody and Radioiodinated Protein A", Anal. Biochem. 112:195–203 (1981).

Cales, et al., "The Cytoplasmic Protein GAP Is Implicated As The Target For Regulation By the ras Gene Product", Nature 332:548 (Apr. 7, 1988).

Carstens, et al., "Infectious DNA from *Autographa Californica* Nuclear Polyhedrosis Virus", Virology 101:311–314 (1980).

Chang, et al., "Tumorigenic transformation of mammalian cells induced by a normal human gene homologous to the oncogene of Harvey murine sarcoma virus", Nature 297:479–483 (Jun. 10, 1982).

Clark, et al., "Antibodies specific for amino acid 12 of the ras oncogene product inhibit GTP binding", Proc. Natl. Acad. Sci. (U.S.A.) 82:5280–5284 (Aug. 1985).

Cohen, "Nonchromosomal Antibiotic Resistance in Bacteria: Genetic Transformation of *Escherichia coli* by R–factor DNA", Proc. Natl. Acad. Sci. U.S.A.) 69:2110–2114 (Aug. 1972).

Feramisco, et al., "Transient reversion of ras oncogene–induced cell transformation by antibodies specific for amino acid 12 of ras protein", Nature 314:639–642 (Apr. 1985).

Gibbs, et al., "Purification of ras GTPase activating protein from bovine brain", Proc. Natl. Acad. Sci. (U.S.A.) 85:5026–5030 (1988).

Graham, et al., "A New Technique for the Assay of Infectivity of Human Adenovirus 5 DNA", Virology 52:456–467 (1973).

Hunkapiller, et al., "Isolation of Microgram Quantities of Proteins from Polyacrylamide Gels for Amino Acid Sequence Analysis", Meth. Enzymol. 91:227–236 (1983).

Hunkapiller, et al., "High–Sensitivity Sequencing With A Gas–Phase Sequenator", Meth. Enzymol. 91:399 (1983).

Huynh, et al., "Constructing and Screening cDNA Libraries in $\lambda$gt10 and $\lambda$gt11", In DNA Cloning Techniques: A Practical Approach (Ed. D. Glover), IRL Press, Oxford, pp. 49–78 (1985).

Ish–Horowicz, et al., "Rapid and Efficient Cosmid Cloning", Nucl. Acids Res. 9:2989–2998 (1981).

Laemmli, "Cleavage of Structural Proteins during the Assembly of the Head of Bacteriophage T4", Nature 227:680–685 (Aug. 1970).

Lane, "Activation of related transforming genes in mouse and human mammary carcinomas", Proc. Natl. Acad. Sci. (U.S.A.) 78:5185–5189 (1981).

Lowry, et al., "Protein Measurement With the Folin Phenol Reagent", J. Biol. Chem. 193:265 (1951).

Luckow, et al., "Trends in the Development of Baculovirus Expression Vectors", Bio/Technology 6:47–55 (Jan. 1988).

Maiorella, et al., "Large–Scale Insect Cell–Culture For Recombinant Protein Production", Bio/Technology 6:1406 (1988).

Mateucci, et al., "Synthesis of Deoxyoligonucleotides on a Polymer Support", J. Am. Chem. Soc. 103:3185–3191 (1981).

Maxam, et al., "Sequencing End–Labeled DNA with Base–Specific Chemical Cleavages", Meth. Enzymol. 65:499–560 (1980).

McCormick, et al., "Interaction of ras p21 Proteins with GTPase Activating Protein", Cold Spring Harbor Symp. Quant. Biol. 53:849–854 (1988).

Mes–Masson, et al., "Overlapping CDNA clones define the complete coding region for the $P210^{c-abl}$ gene product associated with chronic myelogenous leukemia cells containing the Philadelphia chromosome", Proc. Natl. Acad. Sci. 83:9768–9772 (1986).

Messing, "New M13 Vectors for Cloning", Meth. Enzymol. 101:20–78 (1983).

Messing, et al., "A system for shotgun DNA sequencing", Nucl. Acids Res. 9:309–321 (1981).

Mulcahy, et al., "Requirement for ras proto–oncogene function during serum–stimulated growth of NIH 3T3 cells", Nature 313:241–243 (1985).

Mumby, et al., "Chromatographic Resolution and Immunologic Identification of the $\alpha_{40}$ and $\alpha_{41}$ Subunits of Guanine Nucleotide–binding Regulatory Proteins from Bovine Brain", J. Biol. Chem. 263:2020–2026 (Feb. 5 1988).

Myers, et al., "Detection of single base substitutions in total genomic DNA", Nature 313:495–498 (1985).

Myers, et al., "Detection of Single Base Substitutions by Ribonuclease Cleavage at Mismatches in RNA:DNA Duplexes", Science 230:1242–1246 (1985).

Okayama, et al., "A cDNA Cloning Vector That Permits Expression of CDNA Inserts in Mammalian Cells", Mol. Cell. Biol. 3:280–289 (Feb. 1983).

Pizon, et al., "Human cDNAs rap1 and rap2 homologous to the Drosophila gene Dras3 encode proteins closely related to ras in the 'effector'region", Oncogene 3:201–204 (1988).

Polakis, et al., "The Formylpeptide Chemoattractant Receptor Copurifies with a GTP–binding Protein Containing a Distinct 40–kDa Pertussis Toxin Substrate", J. Biol. Chem. 263:4969–4976 (1988).

Pulciani, et al., "ras Gene Amplification and Malignant Transformation", Mol. Cell. Biol., 5:2836–2841 (Oct. 1985).

Regnier, F., "High–Performance Liquid Chromatography of Proteins", Meth. Enzymol. 91:137–190 (1983).

Sanger, et al., "DNA sequencing with chain–terminating inhibitors", Proc. Natl. Acad. Sci. (U.S.A.) 74:5463–5467 (Dec. 1977).

Schägger, et al., "Tricine–Sodium Dodecyl Sulfate–Polyacrylamide Gel Electrophoresis For The Separation Of Proteins In The Range From 1 To 100 KDa", Anal. Biochem. 166:368–379 (1987).

Shaltiel, "Hydrophobic Chromatography", Meth. Enzymol. 104:69–96 (1984).

Shilo, et al., "Unique Transforming Gene In Carcinogen-–Transformed Mouse Cells", Nature 289;607 (1981).

Slamon, et al., "Human Breast Cancer: Correlation of Relapse and Survival with Amplification of the HER–2/neu Oncogene", Science 235:177–182 (1987).

Smith, et al., "Production of Human Beta Interferon In Insect Cells Infected With A Boculovirus Expression Vector", Mol. Cell. Biol. 3:2156–2165 (1983).

Southern, E., "Detection of Specific Sequences Among DNA Fragments Separated by Gel Electrophoresis", J. Mol. Biol. 98:503–517 (1975).

Summers, et al., "A Manual of Methods for Baculovirus Vectors and Insect Cell Culture Procedures", Texas Agricultural Experiment Station, Bulletin No. 155. pp. 1–56 (May 1987).

Takai, et al., "Multiple Small Molecular Weight GTP–Binding Proteins in Bovine Brain Membranes", In Progress in Endocrinology, (ed.s H. Imura, et al.) Elsevier Science Publishers, B.V., Amsterdam 2:995–1000 (1988).

Tamura, et al., "Antibodies Against Synthetic Peptides Or A Tool For Functional Analysis Of The Transforming Protein pp60$^{src}$", Cell 34:587 (1983).

Temeles, et al., "Yeast and mammalian ras proteins have conserved biochemical properties", Nature 313:700–703 (Feb.1985).

Tjian, et al., "Catalytic Properties of the SV40 Large T Antigen", Cold Spring Harbor Symp. Quant. Biol. 44:103–111 (1980).

Trahey, et al., "A Cytoplasmic Protein Stimulates Normal N–ras p21 GTPase, but Does Not Affect Oncogenic Mutants", Science 238:542–545 (Oct. 1987).

Trahey, et al., "Biochemical and Biological Properties of the Human N–ras p21 Protein", Mol. Cell. Biol. 7:541–544 (1987).

Valenzuela, et al., "Four Human Carcinoma Cell Lines With Novel Mutations In Position 12 of c–k–ras Oncogene", Nucl. Acids Res. 14:843 (1986).

Valeriote, et al., "Proliferation–Dependent Cytotoxicity Of Anticancer Agents: A Review", Cancer Res. 35:2619 (1975).

Varmus, H., "The Molecular Genetics of Cellular Oncogenes", Ann. Rev. Genetics 18:553–612 (1984).

Vieira, et al., "The pUC Plasmids, an M13mp7–derived System for Insertion Mutagenesis and Sequencing with Synthetic Universal Primers", Gene 19:259–268 (1982).

Vogel, et al., "Cloning of bovine GAP and its interaction with oncogenic ras p21", Nature 335:90–93 (Sep. 1, 1988).

Waldo, et al., "Identification and purification from bovine brain of a guanine–nucleotide–binding protein distinct from $G_r$, $G_i$ and $G_o$", Biochem. J. 246:431–439 (1987).

Wilchek, et al., "Affinity Chromatography", Meth. Enzymol. 104:3–55 (1984).

Willumsen, et al., "Mutational Analysis of a ras Catalytic Domain", Mol. Cell. Biol. 6:2646–2654 (1986).

Winter, et al., "A Method To Detect And Characterize Point Mutations In Transcribed Genes: Amplification And Overexpression Of The Mutant c–Ki–ras Allele In Human Tumor Cells", Proc. Natl. Acad. Sci. (U.S.A.) 82:7575–7579 (1985).

Wong, et al., "Detection of Activated $M_r$ 21,000 Protein, the Product of ras Oncogenes, Using Antibodies with Specificity for Amino Acid 12", Cancer Res. 46:6029–6033 (1986).

Yokota, et al., "Alterations of myc, myb, and ras$^{Ha}$ Proto–oncogenes in Cancers are Frequent and Show Clinical Correlation", Science 231:261–265 (Jan. 1986).

Borregaard et al., "Subcellular Localization of the b–Cytochrome Component of the Human Neutrophil Microbicidal Oxidase:Translocation during Activation," J. Cell Biol., 97:52–61 (Jul. , 1983).

DeClue et al., "A Conserved Domain Regulates Interactions of the v–fps Protein–Tyrosine Kinase With the Host Cell," Proc. Nat'l Acad. Sci., USA, 84:9064–9068) (Dec. 1987).

Gibbs et al., "Purification of ras GTPase Activating Protein from Bovine Brain," Chemical Abstracts, 109:295 (1988) (ABSTRACT 109:106932q).

Gilboa, E., "Retrovirus Vectors Their Therapeutic Uses in the Molecular Biology," Bioassays, 5(6):252–257 (1986).

Hall et al., "Analysis of Mammalian Ras Effector Function," Cold Spring Harbor Laboratory, Cold Spring Harbor Press, p. 85 (1988) (ABSTRACT).

Higuchi et al., "A General Method of In Vitro Preparation and Specific Mutagenesis of DNA Fragments: Study of Protein and DNA Interactions," Nucleic Acids Res., 16(15):7351–7367 (1988).

Hopp et al., "A Short Polypeptide Marker Sequence Useful For Recombinant Protein Identification and Purification," Bio/Technology, 6:1204–1210 (Oct., 1988).

McCormick et al., "GTPase Activating Protein (GAP) May Be The Ras Effector," Cold Spring Harbor Laboratory, Cold Spring Harbor Press, p.84 (1988).

Mullis et al., "Specific Enzymatic Amplification of DNA In Vitro; The Polymerase Chain Reaction," Cold Spring Harbor Symp. Quant. Biol., 51:263–273 (1986).

Mullis et al., "Specific Synthesis of DNA In Vitro via a Polymerase–Catalyzed Chain Reaction," Meth. Enymology, 155:335–350 (1987).

Sadowski and Pawson, "Catalytic and Non–catalytic Domains of the Fujinami Sarcoma Virus $P_{130gag-fps}$ Protein-–tyrosine Kinase Distinguished by the Expression of v–fps Polypeptides in Escherichia coli," Oncogene, 1: 181–191 (1987).

Sadowski et al., "A Noncatalytic Domain Conserved among Cytoplasmic Protein–Tyrosine Kinases Modifies the Kinase Function and Transforming Activity of Fujinami Sarcoma Virus P130$^{gag-fps}$," Mol. and Cell. Biol., 6(12):4396–4408 (Dec., 1986).

Saiki et al., "Primer–Directed Enzymatic Amplification of DNA with a Thermostable DNA Polymerase," Science, 239:487–491 (Jan. 29, 1988).

Trahey and McCormick, "Control of Ras p21 Function In Vivo By Guanine Nucleotides," Meeting on Oncogenes, NCI, p. 257 (Jul. , 1987).

Wells et al., "An Improved Method for Purifying 2',5'–Oligoadenylate Synthetases," J. Biol. Chem., 259(2):1363–1370 (Jan. 25, 1984).

Clonetech Laboratories, Inc., Product Literature, Human Placenta DNA Library, pp. 11, 41–43.

Higashijima et al., "Mastoparan, a Peptide Toxin from Wasp Venom, Mimics Receptors by Activating GTP–binding Regulatory Protein (G Proteins)," *J. Biol. Chem.*, 263:6491–6494 (May 15, 1988).

Jacobs et al., "Isolation and Characterization of Genomic and cDNA Clones of Human Erythropoietin," *Nature*, 313:806–810 (Feb. 28, 1985).

Köhler and Milstein, "Continuous Cultures of Fused Cells Secreting Antibody of Predefined Specificity," *Nature*, 256:495–497 (Aug. 7, 1975).

Lathe, R., "Synthetic Oligonucleotide Probes Deduced From Amino Acid Sequence Data Theoretical and Practical Considerations," *J. Mol. Biol.*, 183:1–12 (1985).

Lehninger, A.L., "Chapter 7, Proteins:Purification and Characterization," in *Biochemistry*, Second Edition, Worth Publishers, Inc., New York, pp. 157–172 (1975).

Lehninger, A.L., *Biochemistry*, Worth Publishers, Inc., New York, pp. 434–435 (1970).

Lide, (Ed.), CRC Handbook of Chemistry and Physics, 71st Edition, CRC Press, Boca Raton, p. 1–33 (1990).

Maniatis et al., *Molecular Cloning: A Labortory Manual*, Cold Spring Harbor Laboratory, Cold Spring Harbor Press, p. 254–255 (1982).

Merrifield, B., "Solid Phase Synthesis," *Science*, 232(4748):341–347 (Apr. 18, 1986).

Merrifield, B., "Solid Phase Synthesis," *Bioscience Reports*, 5:353–376 (1985).

Miller, J. H., (Ed)., *A Short Course in Bacterial Genetics: A Laboratory Manual and Handbook for Escherichia coli and Related Bacteria*, Cold Spring Harbor Laboratory Press, Cold Spring Harbor, pp. 9.1–9.3, 9.11–9.12, 9.14 (1992).

Record et al., "A Rapid Isolation Procedure of Plasma Membranes From Human Neutrophils Using Self–Generating Percoll Gradients. Importance of pH in Avoiding Contamination by Intracellular Membranes," *Biochimica et Biophysica Acta*, 819:1–9 (1985).

Sambrook et al., *Molecular Cloning A Laboraotry Manual*, Second Edition, Cold Spring Harbor Laboraotry, Cold Spring Harbor Press, pp. 11.7–11.8, 11.45–11.49,11.55–11.57, (1989).

Shacter, E., "Organic Extraction of $P_i$ with Isobutanol/ Toluene," *Anal. Biochem.*, 138:416–420 (1984).

Sigal et al., "Identification of Effector Residues and a Neutralizing Epitope of Ha–ras–Encoded p21," *Proc. Nat'l Acad. Sci., USA*, 83(13):4725–4729 (Jun., 1986).

Sigal et al., "Identification of Effector Residues and a Neutralizing Epitope of Ha–ras–Encoded p21," *Chemical Abstracts*, 105(9):261 (Sep., 1986) (ABSTRACT 74565w).

Suggs et al., "Use of Synthetic Oligonucleotides As Hybridization Probes: Isolation of Cloned cDNA Sequences for Human $\beta_2$–Microglobulin," *Proc. Nat'l Acad. Sci., USA*, 78(11):6613–6617 (Nov., 1981).

Trahey et al., "Molecular Cloning of Two Types of GaP Complementary DNA From Human Placenta," *Science*, 242:1697–1700 (Dec. 23, 1988).

Weaver et al., Genetics, Wm. C. Brown Publishers, Dubuque, Iowa, pp. 451–457 (1989).

REDUCED 10% SDS PAGE
(COOMASSIE-STAINED)

FIG. 3

ILE MET PRO GLU GLU GLU TYR SER GLU PHE LYS

```
  ATC ATG CCC GAG CAG GAG TAC TCC GAG TTC AAG
   T       A   AGA  A   T   T   A   T   A
5  A       T                   A
           G                   G
                             AGC
                               T
```

FIG. 4

Ile MET Pro Glu Glu Glu Tyr Ser Glu Phe Lys

GW13 5'ATC ATG CCT GAG CAG GAG TAC TCT GAG TTC AAG'3

GW15 5'ATC ATG CCT GAG CAG GAG TAC AGT GAG TTC AAG'3

5  GW17 5'ATC ATG CCT GAG GAG GAG TAC TCT GAG TTC AAG'3

GW19 5'ATC ATG CCT GAG GAG GAG TAC AGT GAG TTC AAG'3

```
1681  TCCAGAACAAGCAGAGGATTGGATGAAAGTAGTCCAGGGACATCCAATAAACGCCTTGTCAGGTCAGC     1780
562    P  E  Q  A  E  D  W  M  K  G  L  Q  A  F  C  N  L  R  K  S  S  P  G  T  S  N  K  R  L  R  Q  V  S        594

1781  AGCCTTGTTTTACATATTGAAGAAGCCCATAAACTCCCAGTAAACATTTACTATCCATTGTAACATCTGAATAGTGTCCAAGTAGCAAAAA     1880
595    S  L  V  L  H  I  E  E  A  H  K  L  P  V  K  H  F  T  N  P  Y  C  N  I  Y  L  N  S  V  Q  V  A  K  T        628
           I

1881  CTCATGCAAGGGCAAGGGCAAAACCAGTATGTCAGAGAGTTTGTCTTTGATGATCTTCCCCTGACATCAATAGATTTGAAATAACTCTTAGTAATAA     1980
629    H  A  R  E  G  O  N  P  V  W  S  E  E  F  V  F  D  D  L  P  P  D  I  N  R  F  E  I  T  L  S  N  K        661

1981  AACAAGAAAAGACAAAGATCCTGATATCTCTATTTATGCCGCTGCCAGTTGAGCCCGATTACAGAAAGGGCATGCCACAGATGAATGGTTTCTGCTCAGCTCC     2080
662    T  K  K  S  K  D  P  D  I  L  F  M  R  C  Q  L  S  R  L  Q  K  G  H  A  T  D  E  W  F  L  L  S  S        694

2081  CATATACCATTAAAAGGTATTGAACCAGGGTCTCCCTGCGTGTTCCAGCACGATACTCTATGGAAAATCATGCCAGAAGAGTACAGTGAATTTAAAG     2180
695    H  I  P  L  K  G  I  E  P  G  S  L  R  V  R  A  R  Y  S  M  E  K  I  M  P  E  E  E  Y  S  E  F  K  E        728

2181  AGCTTATACTGCAAAAGCTTCATCAGTAGTCTTATCGTATCGTTATCATGTGGACAGACGACCGGACACTGGCCAGCATCCTACTGAGGATTTTCT     2280
729    L  I  L  Q  K  E  L  H  V  V  Y  A  L  S  H  V  C  G  Q  D  R  T  L  L  A  S  I  L  L  R  I  F  L        761
                                                                                    K

2281  TCACGAAAAGCTTGAATCGTTGTTGTTATGCAGTAAATGACAGAGAAATAAGCATGGAAGATGAAGCCCTATTTCGAGCCACAACACTTGCA     2380
762    H  E  K  L  E  S  L  L  L  C  T  L  N  D  R  E  I  S  M  E  D  E  A  T  T  L  F  R  A  T  T  L  A        794

2381  AGCACCCTTGATGGAGCAGTATGAAGCAGTTGTTCATCATGCTTTGAAAGACTCTATTTTAAAGATAATGGAAAGCAAGCAGTCTT     2480
795    S  T  L  M  E  Q  Y  M  K  A  T  A  T  Q  F  V  H  H  A  L  K  D  S  I  L  K  I  M  E  S  K  Q  S  C        828
                    S                                                               R

2481  GTCAGTTAAGTCCATCAAAGTTAGAACATCAATGAAGAAGAATGAACACTATTGAACACTAATTTAACACACTTTCAGAGCTTGTGGAGAAATATTCAT     2580
829    E  L  S  P  S  K  L  E  K  N  E  D  V  N  T  L  T  H  L  N  I  L  S  E  L  V  E  K  I  F  M        861
                                                       A

2581  GGCTTCAGAAATACTTCCACCGACATTGAGATATATTTATGGTGTTTTACAGAAATCTGTTCAGCATAAGTGGCCTACAAATACCACCATGAGAACAAGA     2680
862    A  S  E  I  L  P  P  T  L  R  Y  I  Y  G  C  L  Q  K  S  V  Q  H  K  W  P  T  N  T  T  M  R  T  R        894
```

FIG.5C

```
2681  GTTGTTAGTGGTTTTGTTTTCTCGACTCATCTCGCCATCCTCAGATTCTCCATCTCCTATTGCTGCAA    2780
 895  V V V S G F V F L R L I C P A I L N P R M F N I I S D S P S P I A A R     928

2781  GAACACTGATATTAGTGGCTAAATCTGTGCAGAACTTGTAGAAGTTTGGAGCTAAGGAGCCCTACATGGAAGGTGTCAATCCATTCATCAA    2880
 929  T L L L V A K S V Q N L V E F G A K E P Y M E G V N P F I K             961
            I
            T

2881  AAGCAACAAACATCGTATGATCATGTTTTTAGATGAACTTGGGAATGGAAACTTCCGGAATCCGAACTTGGGAATGGAAACGTAACCTGAACTTCAGAGACCATTCCGGAATCTACCTGAACTTGCCGATACCTGATACCTGATACCTGATACCTGATACCTGAA    2980
 962  S N K H R M I M F L D E L G N V P E L P D T T E H S R T D L S R D     994
                                                                        C

2981  TTAGCAGCCATTGCATGAGATTTGCCTGGCCTCATTCAGATGAACTTCGAACCTCAGTAATGAGCCGTGCCACAGCAGCACGTATTGAAAAGCTTCTGG    3080
 995  L A A L H E I C V A H S D E L R T L S N E R G A Q Q H V L K K L L A    1028

3081  CTATAACAGAACTGCTTCAACAAAACAAAAACCAGTATACAAAAAACCAATGATGTCAGGTAGCAGCCTTCGCCCCAGTGTCTCGCATGGATTCAGCATGT    3180
1029  I T E L L Q Q K Q N Q Y T K T N D V R                                 1047

3181  CCAACACTGGTAATTCACTTCAGTTTAATGTCTCCTTGCTTCTCTTGCCAAAAATAGCCACACTTTCCACATTCCAGTGATGTGAGCTATGCAAACAAAA    3280

3281  TCCAAGATTCTGCTGGTACAGACCAACCTGTAAGCTATCTGTGCAGGATATATCTGCACTATTCCACATGGAATCAATCTTTAACAACCTC    3380

3381  TGACCCTTGGTGTACAGACCACCTTTCACAAAACGAAATGCTATGACTGTATCTGAACTTCTGATATCTCATTGACAATGTGTATAACTGGATTGCAGACTGTTCTTAC    3480

3481  AAAGTTTTGCTGTCTTTAGAGAAGAATGTCAATGACAATCAAACATTCTATTGACAATGTGTATAACTGGATTGCAGACTGTTCTTAC    3580

3581  TGTAACTACTTCCTGATTAGGAATATGACCATTGACGTTCTTCTGCGAACTGTGAAGTGATAATATAGAATGATCTATTGCTCATCAGCTTTATTTTTAAACA    3680

3681  CTGTATACTTTAAAAAATACTCGATATTCTGTGAAGACTGTATTAGATCTCATAATGCCTTTGTAAATGTTACAAGTAAATAGTTTGAATTCAGTAAATATTATT    3780

3781  TACGACTTATTTGTTGAAATTGCATAATGCAATGTTACCTTCAACCATTTATTAACCTAGAATGTTGTTAAAAGTTATTTGTT    3880

3881  GGTTGTGTATTGCATCAATGCAGTTACCCCTTTGATTATGCAGACAAACCTCATCAGCTGCCTAACTATCTTGAACTTCTGACTACTGTTGTATCTGCTGATATT    3980

3981  CATTATTTGTACTGTATAGTTTTATTTACTTCGTATGTGATGTATTTTTTGTCAAGTTAAGTATTCACAAAGGTTAAGTTAAGTAATAAAACAAGGAATATCTTGCAAAAA    4080

4081  TAGTTCAACGTAGTAGTTTTATTTACTTCGTATGTGATGTATTTTTTTGTCAAGTTAAGT   4180

4181  AAAAAAA 4187
```

FIG.5D

Orientation of polylinker in pAcC6, pAcC8 :

```
        BamHI        Sac I      Bgl II   Eco RI           Sma I
        GATCCACCATGGAGCTCGAGATCTAGAATTCTGCAGCCCGGGTACCGATC
             Nco I        Xho I    Xba I      Pst I       Kpn I
```

Orientation of polylinker in pAcC7, pAcC9, and pAcC12 :

```
            Sma I              Eco RI    Bgl II     Sac I           BamHI
        GATCGGTACCCGGGCTGCAGAATTCTAGATCTCGAGCTCCATGGTGGATC
            Kpn I         Pst I         Xba I      Xho I     Nco I
```

GAP GENE SEQUENCES

The instant application is a continuation of U.S. patent application Ser. No. 07/774,644, filed Oct. 4, 1991, abandoned as of the filing date granted this application; in turn a continuation of U.S. patent application Ser. No. 07/260,807, filed Oct. 21, 1988, now abandoned; in turn a continuation-in-part of U.S. patent application Ser. No. 07/230,761, filed Aug. 10, 1988, now abandoned.

FIELD OF THE INVENTION

This invention relates generally to the field of oncology, and particularly to compositions useful in diagnostic testing for cancer. More specifically, the invention concerns DNA sequences, and compositions containing the same, that can be employed as cancer diagnostics.

BACKGROUND OF THE INVENTION

Several genes have been identified that are thought to play a role in regulating normal cell growth. A subset of these genes, termed ras, consists of at least three members, N-ras, H-ras, and K-ras2. Altered forms of ras, termed oncogenes, have been implicated as causative agents in cancer. Both the normal cellular genes and the oncogenes encode chemically related proteins, generically referred to as p21.

Ras oncogenes, and their normal cellular counterparts, have been cloned and sequenced from a variety of species. Comparison of the structure of these two genes has revealed that they differ by point mutations that alter the amino acid sequence of the p21 protein. Naturally occurring mutations in the ras oncogenes have been identified in codons 12, 13, 59, and 61. In vitro mutagenesis work has shown that mutations in codon 63, 116, 117 and 119 also result in transforming activity. The most frequently observed mutation which converts a normal cellular ras gene into its oncogenic counterpart is a substitution of glycine at position 12 by any other amino acid residue, with the exception of proline. Transforming activity is also observed if glycine is deleted, or if amino acids are inserted between alanine at position 11 and glycine at position 12.

Mutations at position 61 also play an important role in the generation of ras oncogenes. Substitution of glutamine by any other amino acid, except proline or glutamic acid in the cellular ras gene yields ras oncogenes with transforming activity.

In relation to normal cellular ras genes and their oncogenic counterparts, there are at least four known retroviral ras oncogenes which exhibit transforming activity. Unlike their non-retroviral analogues, the retroviral genes exhibit two mutations. The biological significance of these double mutations is at present unclear.

Both the normal ras and oncogenic p21 proteins, regardless of their phylogenetic origin, bind guanine nucleotides, GTP and GDP, and possess intrinsic GTPase activity. See Temeles et al., 1985 *Nature*, 313:700. The significance of these biochemical properties to the biological activities of the ras proteins has been demonstrated as follows: first, microinjection of anti-ras antibodies that interfere with guanine nucleotide binding reverses the malignant phenotype of NIH 3T3 cells transformed by ras oncogenes. See Clark et al., 1985 *Proc. Natl. Acad. Sci. U.S.A.*, 82:5280 and Feramisco et al., 1985 *Nature*, 314:639. Second, ras oncogenic proteins that exhibit mutations which result in the inability of p21 to bind guanine nucleotides do not transform NIH 3T3 cells. Willumsen et al., 1986 *Mol. Cell. Biol.*, 6:2646. Third, some ras oncogenes produce p21 proteins that have much reduced GTPase activity compared to their normal cellular counterparts. The biological role of GTPase activity associated with either ras or its oncogenic counterpart remains unknown.

Recently a cytoplasmic factor has been identified which stimulates normal ras p21 GTPase activity, but does not effect GTPase activity associated with the oncogenic mutants. See M. Trahey and F. McCormick, 1987 *Science*, 238:542. The activity has been associated with a protein, termed GAP, which is the acronym for GTPase activating protein. GAP is thought to be a cytoplasmic protein but is presumably capable of moving from the cytosol to the plasma membrane where it interacts with p21.

As alluded to above, ras oncogenes have been implicated in the development of a variety of tumors, and have been shown to be involved in about 10–40% of the most common forms of human cancer. See H. Varmus, 1984 *Annual Rev. Genetics*, 18:553 and M. Barbacid, 1986, in *Important Advances in Oncology*, ed. B. DeVita, S. Helman, S. Rosenberg, pages 3–22, Philadelphia: Lippincott. For example, ras oncogenes have been consistently identified in carcinomas of the bladder, colon, kidney, liver, lung, ovary, pancreas and stomach. They also have been identified in hematopoietic tumors of lymphoid and myeloid lineage, as well as in tumors of mesenchymal origin. Furthermore, melanomas, teratocarcinomas, neuroblastomas, and gliomas have also been shown to possess ras oncogenes.

Considering the possible association of ras oncogenes and cancer, there has been considerable work focused on diagnostic tests for detecting the presence of the oncogene product, p21, or the mutant oncogenes. Early tests, which are still employed in many instances, identify the presence of ras oncogenes in transfection assays which identify p21 by its ability to transform NIH 3T3 cells. See Lane et al., 1981 *Proc. Natl. Acad. Sci. USA*, 78:5185 and B. Shilo, and R. A. Weinberg, 1981 *Nature*, 289:607. This method is insensitive, laborious, and to be performed adequately, requires a skilled laboratory technician.

A second diagnostic method centers around oligonucleotide probes to identify single, point mutations in genomic DNA. This technique is based on the observation that hybrids between oligonucleotides form a perfect match with genomic sequences, that is, non-mutated genomic sequences are more stable than those that contain a single mismatch. An example of the latter is a point mutation in p21 associated with the ras oncogenes. Although this technique is clearly more sensitive and easier to perform than the transfection assay, it is nevertheless also cumbersome to perform. This is because there are theoretically almost 100 base substitutions which can yield ras oncogenes. Thus, in order to be able to detect these substitutions, multiple oligonucleotide probes must be employed containing each of the three possible substitutions at a particular residue. See Bos et al., 1985 *Nature*, 315:726 and Valenzuela et al., 1986 *Nuc. Acid Res.*, 14:843.

In addition to the transfection and oligonucleotide assays, additional nucleic acid hybridization techniques have been developed to identify ras oncogenes. One such method is based on the unusual electrophoretic migration of DNA heteroduplexes containing single based mismatches in denaturing gradient gels. See Myers et al., 1985 *Nature*, 313:495. This technique only detects between about 25–40% of all possible base substitutions, and requires a skilled technician to prepare the denaturing gradient gels. More sensitive techniques which are refinements of this technique are described by Winter et al., 1985 *Proc. Natl. Acad. Sci. USA*, 82:7575 and Myers et al., 1985 *Science*, 230:1242.

Immunologic approaches have been taken to detect the product of the ras oncogenes. Polyclonal or monoclonal antibodies have been generated against the intact ras oncogene p21, or against chemically synthesized peptides having sequences similar to oncogene p21, or the non-transforming counterpart. See U.S. patent application Ser. No. 938,598; (Cetus 2188A, now abandoned EP Patent Publication 108, 564 to Cline et al.; Tamura et al., 1983 Cell, 34:587; PCT Application WO/84/01389 to Weinberg et al. For the most part antibodies have been disappointing as diagnostic tools with which to identify ras oncogenic p21 in human tissue sections. This is because either the antibodies that have been generated to date recognize the normal cellular ras protein as well as the oncogenic protein, or, in those instances in which a monoclonal antibody has been generated that specifically recognizes the oncogenic protein, nonspecific staining of tumor biopsies is still observed.

While ras oncogenic p21 is an effective tumorigenic agent, recent studies have shown that normal ras p21 can induce the malignant phenotype. See Chang et al., 1982 Nature, 297:7479 and Pulciani et al., 1985 Mol. Cell. Biol., 5:2836. For example, transfection of normal H-ras DNA has been shown to induce malignant transformation. It is further noteworthy that normal ras gene amplification has been observed in several human tumors, and has an apparent incidence of about 1%. Pulciani, et al., above; Yokota et al., 1986 Science, 231:261. The various diagnostic tests used to detect ras oncogenes or oncogenic p21 have been applied to the detection of normal ras p21 with similar limited success.

It should be apparent from the foregoing that while there are a number of diagnostic methods for determining the presence of ras oncogenes, or their transforming proteins, there is still a need for fast and reliable diagnostic methods that will permit the routine identification of a wide variety of ras related tumors.

SUMMARY OF THE INVENTION

In accordance with the present invention, DNA sequences are described that are useful as diagnostics for cancers arising from the expression of normal cellular or oncogenic ras genes.

A second aspect of the invention is a description of GAP cDNA sequences, and methods for isolating and identifying the same, that are useful in cancer diagnosis.

A third aspect of the invention is a description of a full length GAP cDNA sequence that encodes a molecule with a molecular weight of about 116,000, and cDNAs that encode shorter GAP molecules resulting from differential splicing.

A fourth aspect of the invention is a description of the procedures employed to realize the expression of GAP cDNA in bacteria or insect cells.

A fifth aspect of the invention consists of diagnostic methods for detecting cancer using GAP gene sequences.

Further aspects of the invention will become apparent upon consideration of the following description of the invention.

BRIEF DESCRIPTION OF THE DRAWINGS

FIG. 3 shows the GAP amino acid sequence (SEQ ID NO: 1)used to generate DNA probes that were used to identify the lambda gt11 clone, GAP 6. Also shown is the corresponding DNA encoding sequence (SEQ ID NO: 2 with possible codon redundancies.

FIG. 4 shows the DNA probes (SEQ ID NOS: 3–6) used to identify GAP 6.

FIG. 5 presents the DNA (SEQ ID NO: 7) and amino acid sequence (SEQ ID NO: 8) of lambda clone, clone 101.

DETAILED DESCRIPTION OF THE INVENTION

Figure 1:
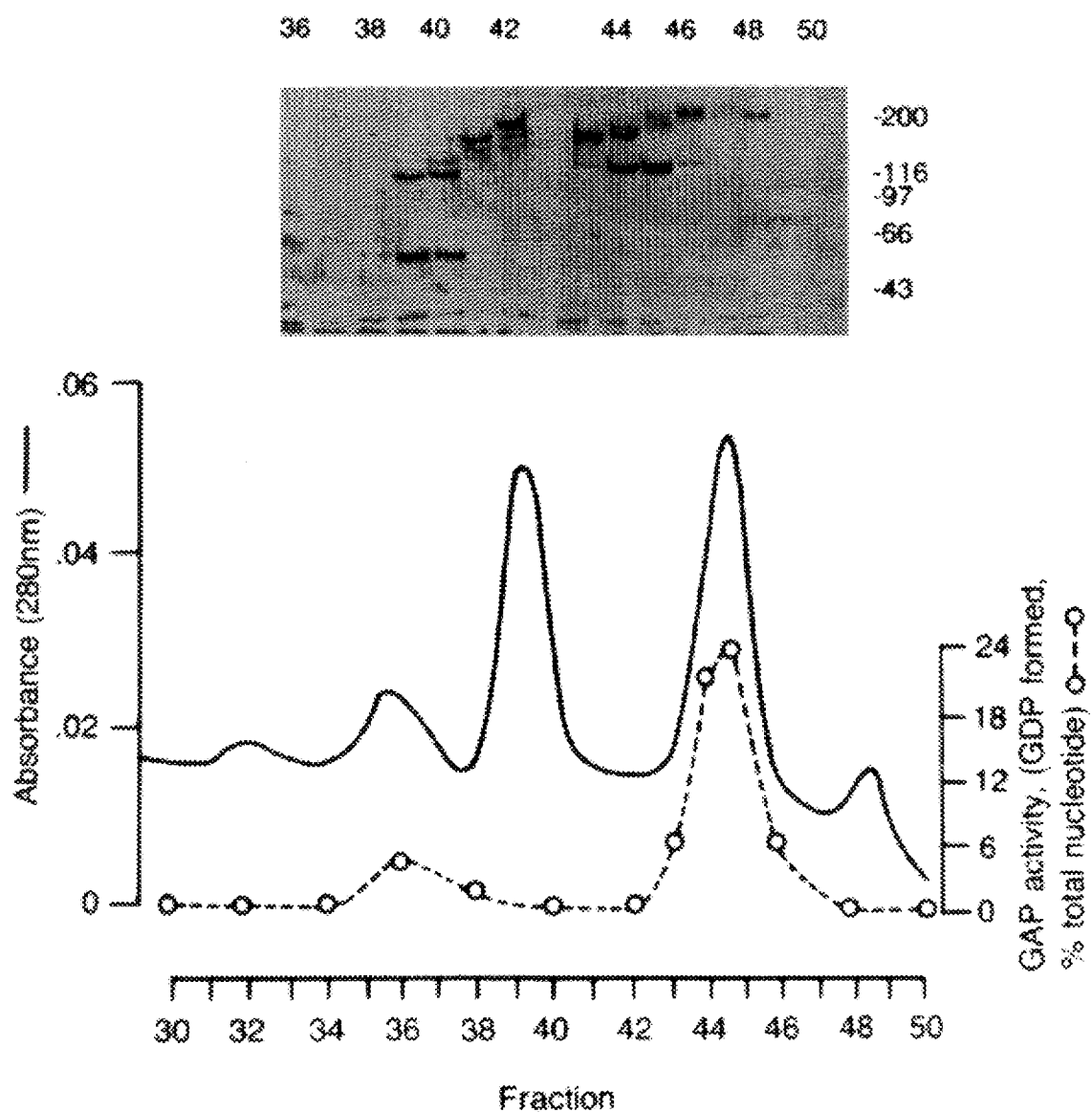
FIG. 1 shows the TSK phenyl column elution profile and silver staining of SDS PAGE fractions thereof.

A better understanding of the invention described herein will be realized by providing a brief description of some of the materials and methods used in the invention.

The normal cellular ras gene and its oncogenic counterparts are defined as described by N. Barbacid, 1987 Ann. Rev. Biochem., 56:779. Similarly, the proteins encoded by these genes are also defined as described by Barbacid. Moreover, it will be appreciated that fragments of normal cellular p21 that bind GTP, and exhibit GAP stimulated GTPase activity are intended to come within the definition of ras p21.

GAP is the acronym for guanine triphosphatase activating protein, and is defined as a protein having a molecular weight and amino acid sequence as described herein, and that has the further properties of stimulating GTPase activity of normal cellular ras p21, while having little or no stimulatory activity when combined with oncogenic ras p21 proteins and GTP. Of course, it will be understood by those skilled in the art that GAP may also exist as aggregates or multimers under certain conditions, and these forms are intended to come within the scope of the definition. Moreover, the definition is further intended to cover fragments of GAP that exhibit activity. Exemplary of such a fragment is a molecule having a reduced subunit molecular weight of about 35,000 as shown herein.

It will further be appreciated with regard to the chemical structure of GAP, that its precise structure may depend on a number of factors. As all proteins contain ionizable amino and carboxyl groups, it is, of course, apparent that GAP may be obtained in acid or basic salt form, or in neutral form. It is further apparent, that the primary amino acid sequence may be augmented by derivatization using sugar molecules (glycosylation) or by other chemical derivatizations involving covalent or ionic attachment to GAP with, for example, lipids, phosphate, acetyl groups and the like, often occurring through association with saccharides. These modifications may occur in vitro or in vivo, the latter being performed by a host cell through post-translational processing systems. It will be understood that such modifications, regardless of how they occur, are intended to come within the definition of GAP so long as the activity of the protein, as defined herein, is not significantly altered.

As used herein, "chromatography" is defined to include application of a solution containing a mixture of compounds to an adsorbent, or other support material which is eluted, usually with a gradient or other sequential eluant. Material eluted from the support matrix is designated eluate. The sequential elution is most routinely performed by isolating the support matrix in a column and passing the eluting solution(s), which changes affinity for the support matrix, either stepwise or preferably by a gradient, through the matrix. It will be appreciated that encompassed within the definition "chromatography" is the positioning of the support matrix in a filter and the sequential administering of eluant through the filter, or in a batch-mode.

The phrase "hydrophobic interaction matrix" is defined to mean an adsorbent that is a hydrophobic solid such as polystyrene resin beads, rubber, silica-coated silica gel, or crosslinked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high salt eluant containing anions such as chloride ion which bind to the anion exchange matrix and displace the adsorbed material.

By the phrase "high salt concentration conditions" is meant an aqueous solution wherein an ionic substance is present to create conditions of high ionic strength. Ionic strength is defined as is generally understood in the art and can be calculated from the putative concentrations of the various ions placed in solution modified by their activity coefficient. High salt concentrations that are routinely employed are typified by solutions containing high concentrations of ammonium sulfate; however, other salts, such as sodium chloride, potassium chloride, sodium sulfate, sodium nitrate, or sodium phosphate may also be employed.

The definition of "affinity chromatography" is understood to be similar to that of Wilchek et al., 1984 *Methods in Enzymology*, 104:3. In its broadest intended definition, "affinity chromatography" is a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

GENERAL DESCRIPTION

The instant invention provides a description of DNA sequences that encode GAP, and materials and methods for identifying and isolating the same. The DNA sequences, or fragments derived therefrom, are useful as cancer diagnostics, being particularly useful to diagnose for ras p21 related cancers. The identification and isolation of the instant GAP DNA sequences is facilitated by the availability of DNA oligonucleotide probes substantially homologous to the GAP sequence. Because such probes were generated based on a knowledge of the partial amino acid sequence of GAP, the order of discussion of the invention will be: purification of GAP; methods of assaying GAP; the partial amino acid sequence of GAP; cloning of GAP using GAP probes based on the amino acid sequence and the identification of GAP DNA sequences in a cDNA library, along with subcloning of the sequences. In this section is also described the expression of the GAP sequences along with methods of using the same to diagnose for cancer.

GAP PURIFICATION

Guanosine triphosphatase activating protein, or GAP, is widely expressed in higher eukaryotes. GAP has been detected in cell extracts from human and mouse normal tissues including brain, liver, placenta, B cells, and platelets. It has additionally been found in non-transformed cell cultures including NIH 3T3, as well as transformed cell lines, including human mammary cancer cells (MCF-7), retinoblastoma cells (Y79), and Wilm's tumor (G401). GAP is also present in insect cells such as, for example, Spodoptera frugiperda. From many of these cells or tissues, GAP may be isolated, albeit with minor variations in the purification protocols and the like.

The general scheme for GAP isolation and purification consists of releasing the molecule from the cytoplasm of appropriate cells, tissues or organs, followed by removing insoluble material and subjecting the soluble GAP fraction to cation exchange chromatography, followed by a second chromatographic step wherein the eluant from the cation exchanger is passed over an anion exchanger. GAP is eluted from the anion exchanger, and further purified by subjecting it to a third chromatographic step, either hydrophobic chromatography, or a second cation exchange step.

More specifically, GAP is prepared by releasing the molecule from the cytosol using any number of techniques including freeze thawing, sonication, mild detergent extraction, etc. This procedure is preferably carried out in a physiologically buffered solution containing one or more protease inhibitors. Moreover, to further inhibit protease activity, especially those proteases that rely on metal ions for activity, the extraction solution may contain metal ion chelators. The preferred extraction solution is a physiologically balanced salt solution containing the chelators ethyleneglycoltrichloroacetic acid (EGTA), or ethylenediaminetrichloroacetic acid (EDTA), plus the protease inhibitor phenylmethylsulfonylfluoride (PMSF). The metal ion chelator(s), as well as the protease inhibitor(s) are present at concentrations that effectively inhibit proteolysis, preferably about 5 mM and 100 µM, respectively. However, it will, of course, be appreciated by those skilled in the art that since the types and amounts of proteases vary depending on the starting material used to extract GAP, the concentrations that the protease inhibitors or chelators are used at, if indeed used at all, will also vary.

The mixture containing GAP is clarified by centrifugation, or in other ways to remove insoluble material from the aqueous cytosol fraction. If the cytosol fraction contains low amounts of GAP it can be concentrated by any one of several techniques well known to those skilled in the art, including high salt precipitation, such as, for example, with ammonium sulfate, or by ultra filtration. If GAP is concentrated by precipitation, it is preferably subsequently resuspended in a suitable physiologically balanced salt solution containing protease inhibitor(s) and preferably about 0.1% of a nonionic detergent, such as NP40. This solution is then prepared for ion exchange chromatography by dialyzing it against a compatibly buffered chromatographic solution, preferably containing millimolar phosphate, a metal ion chelator, a reducing agent, and a protease inhibitor. Additionally, because GAP activity is stimulated by the presence of divalent cations such as magnesium chloride, it may also be present in the solution. The pH of the solution is preferably about 6.0.

The GAP dialyzate is then subjected to chromatographic purification consisting preferably of three steps. The first involves purification using an ion exchange chromatographic step compatible with the GAP extraction buffer. Since the preferred extraction buffer contains phosphate, the initial step is purification of GAP by cation exchange chromatography. The second consists of ion exchange chromatography wherein the ion exchange matrix has the opposite ion binding capacity from that of the first ion exchanger employed.

Thus, the preferred purification scheme will consist of applying the phosphate solution containing GAP to a cation exchanger, and eluting GAP therefrom, preferably using solutions which alter the pH or conductivity of the solution. More preferably, GAP will be eluted by applying either a gradient or non-gradient salt solution, and most preferably will be eluted using a linear gradient of sodium chloride over the range of about 0–0.6 molar.

The preferred cation exchanger is a SP-cellulose cation exchanger. Such are commercially available from AMF Molecular Separations Division, Meridian, CT under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the GAP solution. The flow rate of the solution through the matrix will depend upon the size and geometry of the matrix used. It will be apparent to those skilled in the art, however, that care should be taken to avoid exceeding the unit capacity of the matrix with GAP. If the capacity is exceeded, GAP will not be totally retained and excess unretained GAP will be present in the effluent. The capacity of the matrix to retain GAP can be monitored by assaying for GAP in the effluent using one of the assays described below.

Fractions containing GAP are prepared for the second chromatographic step, that is, anion exchange chromatography. This consists of combining the fractions and adjusting the solution to a pH, and ionic strength compatible with anion exchange chromatography. A variety of anion exchangers are available, and depending on the type employed, the concentrations of these reagents will vary. DEAE-Sepharose or TSK-DEAE-5-PW may be employed. The general procedures for preparing and using these matrices are known to those skilled in the art. The preferred anion exchanger is TSK-DEAE-5-PW matrix. It is prepared by equilibrating it with a solution containing chloride ions at a pH of 8.5. More preferably, the solution will consist of Tris hydrochloride, pH 8.5 plus a reducing agent, a metal chelator, magnesium chloride, and a protease inhibitor. The concentrations of the metal chelator and protease inhibitor will vary and depend on how extensively GAP is proteolyzed, and whether the proteases responsible are activated by metal ions. The concentration of monovalent cations, such as magnesium chloride and reducing agent can be determined empirically by monitoring GAP activity. Those concentrations which maintain the highest activity will be utilized. Generally, it is preferred that magnesium chloride and the reducing agent be present in the range of about 0.5–1 mM, and 0.1–1 mM, respectively.

The solution is then passed through the anion exchange matrix whereupon GAP binds to the matrix. GAP is subsequently eluted from the matrix using solutions which alter the pH or conductivity. The preferred elution method consists of eluting GAP using a linear salt gradient ranging from 0–0.6 molar sodium chloride. The purity and activity of GAP so obtained can be monitored by the GTPase assay described below, and by sodium dodecyl sulfate polyacrylamide gel electrophoresis run under reducing conditions. Using these techniques it was determined that GAP has a molecular weight of about 115,000–120,000 daltons.

The third chromatographic step consists of applying, after the anion exchange chromatography, either a second cation exchange step, or a hydrophobic interaction chromatographic step. The most preferred purification scheme utilizes a second cation exchange step. Application of either of these methods will generally increase the purity of GAP to about 95%. If a cation exchange column is chosen, the materials and methods described above are similarly applicable here. Generally, this will consist of decreasing the salt concentration present in the anion column eluates and adjusting the pH to about 6.0. Here, as in the initial cation chromatographic step, several different types of cation exchange matrices can be employed; however, the preferred matrix is a SP-TSK column which is run under high pressure. If hydrophobic chromatography is selected, the ionic strength of the eluate from the anion exchanger should be increased to be compatible with hydrophobic interaction chromatography. The solution can then be passed through a hydrophobic interaction chromatographic matrix, and eluted using techniques known in the art, including decreasing the salt concentration, or eluting with a chaotropic agent. Either of the latter solutions may be used alone, or in combination.

A variety of hydrophobic interaction chromatographic matrixes may be utilized. Generally, the materials and methods for utilizing hydrophobic chromatography are described by S. Shaltie, 1984 *Methods in Enzymology*, 104:69. While it is apparent there are many hydrophobic chromatographic materials and methods that may be employed to purify GAP, phenyl Sepharose is preferred, and it is further preferred that the chromatography be employed under high pressure. The general procedures for forming high pressure liquid chromatography involving a phenyl derivatized matrix are described by F. Regmaer, 1983 *Methods in Enzymology*, 91:137. The preferred phenyl derivatized matrix is available commercially from Bio-Rad Corporation, and is sold under the trade name Biogel TSK phenyl-5-PW.

It will be additionally appreciated by those skilled in the art that an alternative purification scheme may consist of a cation and anion chromatographic exchange step, followed by an affinity chromatographic step. This may be achieved by binding GAP to one or more plant lectins having a known carbohydrate specificity compatible with carbohydrates which may be present on GAP, or by binding GAP to anti-GAP antibodies. In either event, GAP can then be released from the affinity matrix using the appropriate sugar if the matrix is composed of a lectin, or by pH or chaotropic agents if the matrix is composed of antibody.

Because GAP is a protease-sensitive molecule that is broken down into lower molecular weight species having GAP activity, in a preferred embodiment of the invention the entire purification procedure is carried out rapidly in the cold to reduce protease activity. In general, this temperature is in a range below 10° C., with a preferred temperature range being about 2°–8° C. Most preferred is a temperature of about 4° C.

Finally, it should be noted that while the preferred applications of the ion exchange materials described herein are in a column format, it will be appreciated that they may also be used in batch format as well.

A preferred embodiment purification scheme consists of isolating GAP from human placentas as follows.

GAP was isolated from 300 g of human placentas by the following three-step chromatographic procedure. Placentas were obtained shortly after delivery, and kept on ice until they were processed. After it was determined by standard tests that the placentas were free of HIV antibodies, they were processed as follows. The initial step consisted of mechanically removing connective tissue, and ridding the placentas of excess blood by multiple soakings in phosphate buffered saline (PBS). The placentas were then fragmented by freezing the tissue at −70° C., followed by placing the tissue in solution of PBS containing 5 mM EGTA, 100 AM PMSF and disrupting the tissue in a blender until a uniform, fine suspension was apparent. The suspension was centrifuged at 100,000×g to remove insoluble debris, the supernatant removed and the proteinaceous material therein precipitated with 40% ammonium sulfate. The ammonium sulfate was removed, and the precipitated proteins resuspended in PBS containing 0.1% NP40 and 100 µM PMSF. This solution was immediately dialyzed against 20 mM potassium phosphate, 1 mM MgCl$_2$, 5 mM EGTA, 0.1 mM DTT, 100 µM PMSF, pH 6.1 for six hours. This solution was then immediately chromatographed on a cation matrix, S-Sepharose (fast flow, obtainable from Pharmacia Corporation), pre-equilibrated in 20 mM potassium phosphate, 1 mM MgCl$_2$, 5 mM EGTA, 0.1 mM DTT, 100 µM PMSF, pH 6.1.

Proteins absorbed to the cation exchanger were eluted with a linear salt gradient containing 0–0.6 M sodium chloride. Using the GAP assay described below, most of the GAP activity was shown to be present in two peaks, a major peak eluting at a sodium chloride concentration of 100–150 mM, and a minor peak eluting at a sodium chloride concentration of 220–300 mM. The major peak was dialyzed against 30 mM Tris-HCl, 1 mM magnesium chloride, 1 mM EGTA, 0.1 mM DTT, 100 µM PMSF, pH 8.5. The dialyzate was applied to an anion exchange column, TSK-DEAE-5-PW (150×21.5 mm). The anion exchange matrix was treated with a linear salt gradient ranging from 0–0.6 M sodium chloride to elute the adherent proteins. Most of the GAP activity eluted at a sodium chloride concentration of about 130 mM NaCl. Those fractions containing GAP activity were pooled, brought to 0.5 M ammonium sulfate, and passed through a hydrophobic column, phenyl-TSK HPLC. Proteins were eluted from the hydrophobic column using a crisscross gradient consisting of increasing ethylene glycol 0–30%, and decreasing ammonium sulfate, 0.5 M-0. The majority of GAP activity eluted at a concentration of 24% ethylene glycol and 0.1 molar ammonium sulfate. GAP activity assays, as performed below, correlated with a protein band of about 120,000 daltons, as revealed by sodium dodecyl sulfate polyacrylamide gel electrophoresis on 6% gels run under reducing conditions (FIG. 1).

A second embodiment purification scheme was employed to purify GAP. Human placentas were again obtained shortly after delivery, and soaked in ice cold PBS, and homogenized and clarified as described in Example I. Ammonium sulfate was again added to the clarified homogenate to a final concentration of 40% to precipitate proteinaceous material. The ammonium sulfate solution was allowed to stand for one hour at 4° C. prior to recovering the precipitated proteinaceous material by centrifugation for 15 minutes at 10,000×g. The pellet was resuspended in PBS containing 0.1% NP40 and 100 µM PMSF. This solution was dialyzed for six hours at 4° C. against 20 mM potassium phosphate, pH 6.1, containing 1 mM MgCl$_2$, 5 mM EGTA, 0.1 mM DTT, and 100 µM PMSF. Because GAP is susceptible to proteolysis, longer dialysis times are not desirable.

The GAP dialyzate was diluted three-fold with 4 mM potassium phosphate, pH 6.1, containing 0.02 M MgCl$_2$, 1 mM EGTA, 0.1 mM DTT, and 100 µM PMSF to lower the conductivity of the solution to 1 millisiemens. This conductivity is compatible with application of the dialysate to a S-Sepharose cation exchange column. The dialysate was clarified by centrifugation at 10,000×g for 10 minutes, followed by a further clarification step consisting of filtration through a 0.45 µm filter, prior to adding the dialysate to the S-Sepharose column (fast-flow, Pharmacia). Most of the contaminating proteins passed through the S-Sepharose column, and the adsorbed proteins eluted with a 1.5 liter salt gradient consisting of 0–0.6 M NaCl. Those fractions containing GAP activity were identified using the GAP assay described below.

As observed in the first example, GAP eluted from the cation exchange column in predominantly two major peaks. The first peak eluting over a sodium chloride concentration of 100–150 mM was pooled and dialyzed against 30 mM Tris-HCl buffer, pH 8.5, containing 1 mM EGTA, 1 mM MgCl$_2$, 0.1 mM DTT and 100 µm PMSF. The solution was dialyzed at 4° C., and clarified by filtration with a 0.45 µm filter. The filtrate was divided into equal halves, and each half purified using two consecutive anion exchange columns.

Figure 2:
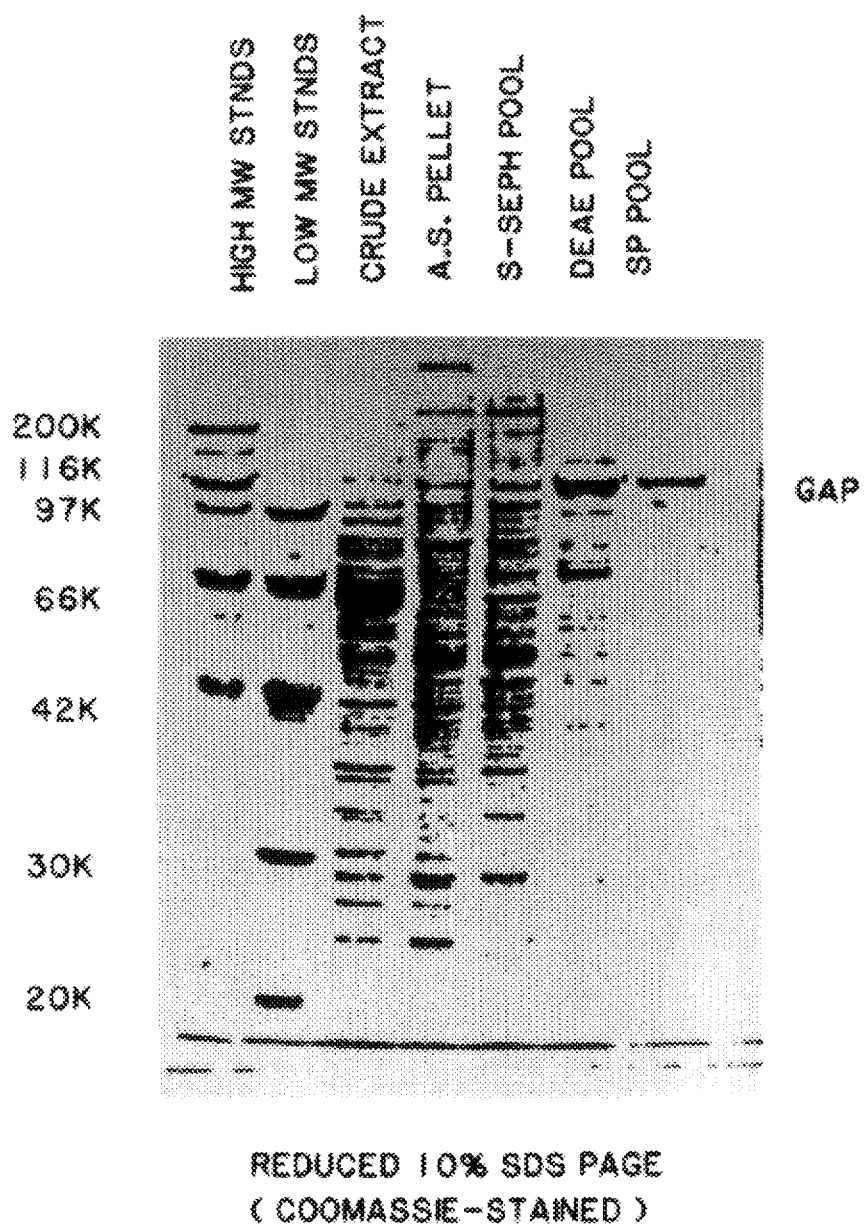
FIG. 2 shows the SDS gel profile of GAP purified by a three-step chromatographic scheme consisting of cation, and anion chromatography, followed by a second cation chromatographic step.

The two filtrates were separately loaded onto a TSK-DEAE-5-EW column having the dimensions 150×21.5 mm. The column was pre-equilibrated in the Tris-hydrochloride, pH 8.5 dialysis buffer described above. GAP was eluted from the column with a 60-minute 0–0.6 M NaCl gradient with a flow rate of 3 ml/minute. The majority of the GAP activity from both filtrates eluted as a single peak at a sodium chloride concentration of about 130 mM. Sodium dodecyl sulfate, polyacrylamide gel electrophoretic analysis of the DEAE fractions showed that GAP was the major protein in the peak activity fractions. Fractions containing GAP from both purifications were pooled and diluted 5-fold into 2 mM potassium phosphate, pH 6.1, containing 0.1 mM EGTA, 10 µM DTT, 10 µM PMSF to lower the salt concentration to insure that the solution was chromatographically compatible with a second cation exchange chromatographic step, that is, chromatography with a SP-TFK column. The pH of the solution was checked and adjusted to pH 6.1 with sodium acetate (3 M, pH 4.8) if necessary. Both of the GAP fractions isolated from the DEAE columns were further purified separately over a cation column, TSK-SP-5-PW having dimensions of 75×7.5 mm. A solution containing 20 mM potassium phosphate, pH 6.1, containing 1 mM EGTA, 0.1 DTT, and 0.1 mM PMSF was passed through the column, followed by eluting GAP with a 45-minute, 0–0.6 M sodium chloride gradient at 1 ml per minute. Those fractions containing GAP were identified using the assay described below and sodium dodecyl sulfate polyacrylamide gel electrophoresis. GAP activity corresponded to a protein having a molecular weight of about 116,000 daltons. Amino acid analysis was performed on purified GAP to determine protein concentration. Starting with about 300 grams of human placenta, approximately 430 micrograms of purified GAP was obtained. FIG. 2 shows the SDS PAGE analysis of GAP at the various stages of purification described above.

GAP ASSAY

Several assays have recently been described to measure GAP activity. M. Trahey and F. McCormick, 1987 *Science*, 238:542; Adari et al., 1988 *Science*, 240:518. These references are herein incorporated in their entirety. GAP may be assayed in vitro, and several different types of in vitro assays can be performed. The preferred assay involves measuring the presence of GDP resulting from the hydrolysis of GTP. This assay involves combining in an appropriate physiologically buffered aqueous solution, empirically determined optimal amounts of normal cellular p21, and α-32P-GTP, plus GAP. The solution may also contain protease inhibitors and a reducing agent. Also, since cations greatly stimulate GAP activity they should be present in an effective amount. The preferred cation is magnesium chloride.

The reaction solution is incubated for various times and may be conducted at temperatures typically employed to perform enzymatic assays, preferably 10°–40° C., and more preferably at 37° C. At the appropriate times aliquots are removed and assayed for α-32P-GDP. This is readily accomplished by first separating p21 containing bound α-32P-GDP from the other reactants in the solution, particularly free α-32P-GTP. This can be achieved by immunoprecipitating p21 with antibodies directed thereto. Immune precipitation techniques and anti-p21 antibodies are known, and routinely employed by those skilled in the art. For example, Adarti, et al., which has been incorporated by reference above, discloses immunoprecipitation reagents that include Y13–259 anti-ras monoclonal antibody, Y13–238 anti-ras monoclonal antibody, and, more preferably, anti-ras monoclonal antibody directed against Ras amino acid residues 157–181. Adari, et al., Science 240:518, 519 (1988). Anti-ras monoclonal antibody 157–181 binds to the carboxy terminus of normal p21 and does not interfere with GAP stimulation of the intrinsic GTPase of p21, unlike the Y13–259 and Y13–238 antibodies which bind elsewhere to p21 and do inhibit GAP stimulation of p21 GTPase. Id. α-32P-GDP, is released from the immune precipitate preferably by dissolving the sample in a denaturing detergent at an elevated temperature, more preferably in 1% sodium dodecyl sulfate at 65° C. for five minutes, and chromatographing the mixture on a suitable thin layer chromatographic plate. The chromatography is preferably carried out on a PEI cellulose plate in 1M LiCl. α-32P-GDP is identified by its mobility relative to a known standard using suitable radiodetection techniques, preferably autoradiography.

An alternative assay for GAP activity is to substitute gamma labeled 32P-GTP for α-labeled 32P-GTP in the above assay system, and assay for free 32P labeled phosphate using activated charcoal. This assay can be carried out as described by Tjian et al., 1980 *Cold Spring Harbor Symp. Quant. Biol.*, 44:103.

An additional assay does not involve immune precipitation. Rather, an aliquot from a GAP assay reaction mixture described above can be directly subjected to PEI cellulose chromatography in 1M LiCl. This assay, however, is most useful for assaying solutions having substantially purified GAP.

A typical GAP assay can be carried out as follows. Approximately 0.8 micrograms of H-ras protein obtained as described by Trahey, et al., supra was bound to α-32P-GTP followed by precipitation of the complex with 13 micrograms of an anti-ras antibody, 157–181, that recognizes the carboxyl terminal end of the molecule. Specifically, 157–181 recognizes the carboxyl terminal residues at positions 157–181. Adari t al., 1988 *Science*, 240:518. Next, 10 micrograms of sheep-anti-mouse IgG, and 10 microliters of protein A-Sepharose beads were added. As a control, the same reactants were combined except that rat IgG replaced 157–181, and goat anti-rat IgG replaced sheep anti-mouse IgG. The pellets were washed with 20 mM tris hydrochloride, pH 7.4, containing 20 mM sodium chloride, 1 mM magnesium chloride and 1 mM DTT and resuspended in the same solution. Four microliter aliquots of the immune complex were then mixed with 10 microliters of GAP, or, as a control, buffer without GAP. After 60 minutes incubation at room temperature the Sepharose beads were washed again, and the bound nucleotides analyzed using thin layer chromatography with 1M LiCl as the solvent. The thin layer plate was autoradiographed for one to two hours after which it was developed. The autoradiograph revealed that addition of sufficient GAP causes the near complete hydrolysis of GTP to GDP, whereas very little GTP hydrolysis occurs in the control lacking GAP. The assay detects GAP in a semi-quantitative, dose-dependent fashion. Quantitation can be improved by scraping the relevant regions of the plate and measuring cpm in GDP by use of a gamma counter. The immune precipitation controls having rat IgG substituted for the mouse antibodies revealed no GTP or GDP. In an in vivo GAP assay of Trahey, et al., human N-ras p21 is first expressed in *Escherichia coli*. Trahey, et al., Science 238:542, 543, FIG. 1 (1987). The p21 is purified using antibody affinity chromatography, preferably with a mouse anti-ras monoclonal antibody, recognizing Ras amino acid residues 29–44, as ligand. In other embodiments, the ligand is Y13–259 anti-ras monoclonal antibody, Y13–238 anti-ras monoclonal antibody, or anti-ras monoclonal antibody directed against Ras amino acid residues 157–181. Adari, et al., Science 240:518, 519 (1988). Elution of p21 bound to the antibody affinity matrix is effected with 100 mM sodium carbonate, pH 10.6. Eluted p21 is then dialyzed into buffer A (80 mM β-glycerophosphate, 5 mM MgCl$_2$, 1 mM DTT, pH 7.5).

According to Trahey, et al., the purified p21 was suitable for microinjection into stage VI *Xenopus laevis* oocytes. The oocytes were surgically excised from sexually mature female *X. laevis* toads stimulated with 25 units of pregnant mare serum gonadotropin 24 hours prior to surgery. Trahey, et al., at page 543, FIG. 1. Fifty nl of purified p21 (2–3 mg/ml in Buffer A) was microinjected into each oocyte and incubated for 23 hours in modified Ringer's saline (100 mM NaCl, 1.8 mM KCl, 2 mM MgCl$_2$, 1 mM CaCl$_2$, 4 mM NaHCO$_3$, pH 7.8). Oocyte maturation was determined by the appearance of a well-defined white spot at the pigmented animal pole by visual inspection, indicative of germinal vesicle breakdown. Alternatively, oocyte maturation was determined by directly determining the state of the germinal vesicle upon splitting open fixed oocytes. Oocyte fixation was accomplished using 5% trichloroacetic acid.

In another in vivo GAP assay of Trahey, et al., 2 μM p21 in Buffer A was incubated with 200 μM [α-$^{32}$P]GTP (8 Ci/mmol), 3 mM ATP, and 1–2 mg/ml bovine serum albumin for 3 hours at room temperature. Trahey, et al., at pages 543–544, FIGS. 2 and 3. Fifty nl of the radiolabelled p21 was microinjected into each of several *X. laevis* stage VI oocytes and incubated in modified Ringer's saline (100 mM NaCl, 1.8 mM KCl, 2 mM MgCl$_2$, 1 mM CaCl$_2$, 4 mM NaHCO$_3$, pH 7.8). At various times from 0–180 minutes, aliquots consisting of 20 microinjected oocytes were removed. The oocytes were crushed in Buffer B (20 mM Tris-HCl, pH 8.0, 100 mM NaCl, 5 mM MgCl$_2$) supplemented with 1% NP 40. Lysates were then centrifuged at 15,000×g for 10 minutes 4° C. Supernatants, diluted to 0.5% NP 40, were then exposed, in an optional step, to anti-ras monoclonal antibody Y13–259 at 0° C. Immune complexes were precipitated with goat anti-Rat IgG-Protein A Sepharose and washed ten times in Buffer B supplemented with 0.5% NP 40. Nucleotides were then eluted from p21 with 1% sodium dodecyl sulfate, 20 mM ethylenediamine tetraacetate at 65° C. for 5 minutes. Eluted nucleotides were fractionated on PEI Cellulose thin layer plates using 1M LiCl and visualized by autoradiography. Identification was facilitated by co-chromatographing radiolabelled nucleotide standards.

In another in vitro assay of Trahey, et al., p21 was purified by antibody affinity chromatography as previously recited. A 4 μM solution of p21 was incubated with 255 μM [α-$^{32}$P] GTP (16 Ci/mmol), 4 mM ATP, and 2.5 mg/ml bovine serum albumin at 37° C. for 30 minutes. Trahey, et al., at page 544, FIG. 4. Two μl of that solution was then added to 20 μl of X. laevis oocyte extract to initiate the assay. The oocyte extract was prepared from stage VI oocytes treated with 2.5 mg/ml collagenase for 12 hours. Following collagenase treatment, the oocytes were washed with Ringer's saline solution (100 mM NaCl, 1.8 mM KCl, 2 mM MgCl$_2$, 1 mM CaCl$_2$, 4 mM NaHCO$_3$, pH 7.8), packed by low-speed centrifugation, optionally washed in standard phosphate-buffered saline, and lysed by centrifugation at 16,000×g for 30 minutes. Trahey, et al., at pages 544–545, FIGS. 4 and 5. Following addition of radiolabelled p21 to the oocyte extract, the reaction was allowed to proceed for 60 minutes at room temperature. Subsequently, the p21 was immunoprecipitated as described previously and any associated nucleotides were eluted and fractionated on PEI Cellulose plates for autoradiographic comparison to co-chromatographed nucleotide standards, all as previously described.

In one of the in vitro GAP assays of Adari, et al., a modification of the method described above was used. In the modified assay, the oocyte extract was replaced by a human mammary cancer cell extract, MCF-7. Adari, et al., at page 519, FIG. 1. Initially, MCF-7 cells were lysed in TNMN buffer (20 mM Tris-HCI [pH 8.0], 100 mM NaCI, 5 mM MgCI$_2$, and 0.5% NP 40). The lysate was centrifuged to remove cell debris and the supernatant adjusted to a 1.5 mg/ml protein concentration using TNMN buffer. Two hundred nanograms of p21, purified as above, in 350 mM guanidine-HCI were then incubated in the presence of [α-$^{32}$P]GTP (1.3 mCi/ml; 1.7 μM) at 37° C. for 20 minutes. Radiolabelled p21 (1.5 μl) was then mixed with 10 μl of MCF-7 extract and incubation continued for 60 minutes at room temperature. The incubation was terminated by immunoprecipitation using 1 μg of Y13–259 anti-ras monoclonal antibody, 2 μg of goat anti-rat IgG, and 10 μl of protein A-Sepharose beads. Nucleotides were then eluted from the immune complexes by addition of 10 μl of buffer containing 1% sodium dodecyl sulfate and 20 mM ethylenediamine tetraacetate and incubation at 60° C. Eluted nucleotides were fractionated on PEI Cellulose plates in 1M LiCI and visualized by autoradiography. Identification was aided by co-chromatography of radiolabelled nucleotide standards. Additionally, the skilled artisan is aware that other mammalian, and non-mammalian, cell extracts can be subjected to GAP assays.

In addition to the above method, GAP can be preferably assayed as follows. 30 Four μM normal cellular p21 was dissolved in a buffer containing 80 mM β-glycerophosphate, 5 mM MgCl$_2$, 1 mM DTT, pH 7.5, plus 255 μM [α-32P] GTP (16 Ci/mmole), 4 mM ATP, and bovine serum albumin (2.5 mg/ml). The mixture was preincubated for 30 minutes at 37° C., followed by the addition of either a sample suspected of containing GAP, or an equal volume of buffer. After one hour at room temperature the monoclonal antibody Y13–259 in the presence of 0.5% NP40 was added in an amount sufficient to bind all the p21 present in the solution. Next, goat anti-Rat Ig-Protein A Sepharose was added to collect p21 bound to Y13–259, and the immune complex isolated and washed ten times in 20 mM Tris-HCl, pH 8.0, 100 mM NaCl, 5 mM MgCl$_2$, and 0.5% NP40. To determine the extent of GTP binding and hydrolysis during these steps a control was run consisting of adding 5 μg of p21 immediately before adding Y13–259.

Nucleotides were eluted from p21 with 1% SDS, 20 mM EDTA at 65° C. for five minutes and chromatographed on PEI Cellulose in 1M LiCl. GTP and GDP were visualized using standard autoradiographic techniques. The results showed that normal cellular p21 affects a nearly complete conversion of GTP to GDP when compared to mutant ras oncogenic proteins Asp 12 and Val 12 assayed similarly. Moreover, little or no GTP or GDP was detected in the control sample.

The assays described above are presented in more detail by Trahey and McCormick, 1987 in *Science*, 238:542, and by Adari et al., 1988 in *Science*, 240:518. Both of these references are hereby incorporated by reference.

GAP AMINO ACID SEQUENCE

The GAP protein, or fragments derived therefrom can be sequenced using standard techniques known to those skilled in the art. In the event that GAP is isolated having a blocked amino terminal end, internal sequencing can be achieved by fragmenting the molecule such as, for example, with lysyl endopeptidase, and sequencing one or more of the resulting fragments. Although this may not necessarily be the case for GAP isolated from sources other than placenta, in the instant invention it was determined that GAP exhibited a blocked amino terminal end.

The protein having a molecular weight of about 120,000 obtained by the purification method described above was electro-eluted from a 6% sodium dodecyl sulfate, polyacrylamide gel in 0.05 molar ammonia bicarbonate containing 0.1% sodium dodecyl sulfate. The procedure followed is described by Hunkapillar et al., 1983 *Methods in Enzymology*, 91:227. The electro-eluted protein was fragmented for internal sequencing using lysyl endopeptidase (5% w/w, 18 hours at 40° C., WAKO). Peptides were fractionated by reverse-phase high performance liquid chromatography using a Brownlee Aquapore RP-300 cartridge (100×2.1 mm, Applied Biosystems). Peptides were eluted with an Acetonitrile gradient from 0–70% in 120 minutes (Buffer A, 0.1% trifluoroacetic acid (TFA) in H20; Buffer B, 0.085% TFA in 85% acetonitrile). Automated sequence analysis of the peptides was conducted on an Applied Biosystems 470A gas-phase sequencer as reported. A peptide characteristic of GAP has the following amino acid sequence:

I M P E E E Y S E F K.

CLONING OF GAP

A full length cDNA sequence that encodes GAP was obtained as follows: first, partial cDNA sequences were identified in a cDNA library using as oligonucleotide probes, DNA sequences derived from the partial amino acid composition of GAP. One such partial cDNA sequence, referred to as GAP 6, was subcloned and sequenced. Knowledge of its DNA sequence led, in turn, to additional probes that were used to screen cDNA libraries for longer cDNA inserts, eventually yielding the full length clone, clone 101. Each of the various procedures will be discussed below.

1. General Cloning Techniques

Construction of suitable vectors containing the desired GAP coding sequence employs standard ligation and restriction techniques which are well understood in the art. Isolated vectors, DNA sequences, or synthesized oligonucleotides are cleaved, tailored, and religated in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution. In the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15 to 25 minutes at 20 to 25° C. in 50 mM Tris pH 7.6, 50 mM NaCl, 6 mM $MgCl_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 µl volumes under the following standard conditions and temperatures: 20 mM Tris-Cl pH 7.5, 10 mM $MgCl_2$, 10 mM DTT, 33 µg/ml BSA, 10 mM-50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 µg/ml total DNA concentration. In blunt end ligations, the total DNA concentration of the ends is about 1 µM.

In vector construction employing "vector fragments," the vector fragment is commonly treated with bacterial alkaline phosphatase (BAP) in order to remove the 5′ phosphate and prevent religation of the vector. BAP digestions are conducted at pH 8 in approximately 150 mM Tris, in the presence of $Na^+$ and $Mg^{+2}$ using about 1 unit of BAP per µg of vector at 60° C. for about 1 hour. Nucleic acid fragments are recovered by extracting the preparation with phenol/chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., (1981 *Nucleic Acids Res.* 9:2989) and analyzed by restriction and/or sequenced by the dideoxy method of F. Sanger et al., 1977 *Proc. Natl. Acad. Sci. (USA)*, 74:5463 as further described by Messing et al., 1981 *Nucleic Acids Res.*, 9:309, or by the method of Maxam et al., 1980 *Methods in Enzymology*, 65:499.

Host strains used in cloning in M13 consists of *E. coli* strains susceptible to phage infection, such as *E. coli* K12 strain DG98 are employed. The DG98 strain has been deposited with ATCC Jul. 13, 1984 and has accession number 1965.

Depending on the host cell used, transformation is done using standard techniques appropriate to such cells. The calcium treatment employing chloride, as described by S. N. Cohen, 1972 *Proc. Natl. Acad. Sci. (USA)* 69:2110, or the $RbCl_2$ method described in Maniatis et al., 1982 *Molecular Cloning: A Laboratory Manual* Cold Spring Harbor Press, p. 254 was used for procaryotes. Transfection of Sf9 cells was achieved using a modification of the calcium phosphate precipitation technique (Graham, F. L. et al., 1973 *Virology* 52:456) as adapted for insect cells (J. P. Burand et al., 1980 *Virology* 101; E. B. Casstens et al., 1980 *Virology* 101:311). Additional details regarding transfection of Sf9 cells are described by Summers and Smith in "A Manual of Methods for Baculovirus Vectors and Insect Cell Culture Procedures", Texas A & M Press: 1986. The baculovirus transfer vectors employed herein are derived from transfer vectors which have been described by G. E. Smith et al., 1983, above. These vectors were originally constructed by cloning the AcNPV EcoRI-1 fragment containing the polyhedrin gene into the Eco RI site of *E. coli* plasmid pUC8 as described by Vieira et al., 1982 *Gene* 19:259–268. A family of plasmids having single Bam HI cloning sites at various locations in the polyhedrin gene were created as described by Smith et al., 1983, above. The most used of these, pAc373, has a unique Bam HI site 50 base pairs downstream from the polyhedrin cap site, that is to say, 8 base pairs before the polyhedrin ATG translation initiation codon (Luckow and Summers in *Biotechnology*, Vol. 6, p. 47 (1988).

2. Oligonucleotide Probes

Synthetic oligonucleotides were prepared by the triester method of Matteucci et al., 1981 *J. Am Chem. Soc.* 103:3185 or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5mM dithiothreitol, 1–2 mM ATP, 1.7 pmoles gamma $^{32}$P-ATP (2.9 mCi/mmole), 0.1 mM spermidine, 0.1 mM EDTA.

Using the partial GAP amino acid sequence described above, and known codon redundancies thereto, several DNA oligonucleotide probes were synthesized and these are shown in FIGS. 3 and 4.

3. Identification and Isolation of GAP Sequences

Several procedures are available for identifying GAP DNA sequences. The preferred procedure is to use the oligonucleotide probes described above to screen cDNA libraries. cDNA libraries can be constructed using techniques known in the art, or can be purchased commercially.

An illustrative procedure for making a cDNA library containing GAP 20 sequences may consist of isolating total cytoplasmic RNA from suitable starting material, and further isolating messenger RNA therefrom. The latter can be further fractionated into Poly (A+) messenger RNA, which in turn is fractionated further still into Poly (A+) messenger RNA fractions containing GAP messenger RNA. The appropriate GAP messenger RNA can then be reverse transcribed and cloned into a 25 suitable vector to form the cDNA library.

More specifically, the starting material (i.e., tissue, cells) is washed with phosphate buffered saline, and a non-ionic detergent, such as ethylene oxide, polymer type (NP-40) is added in an amount to lyse the cellular, but not nuclear membranes, generally about 0.3%. Nuclei can then be removed by centrifugation at 1,000×g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25 M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA. Polyadenylated (Poly A+) messenger RNA (mRNA) can be obtained from the total cytoplasmic RNA by chromatography on oligo (dT) cellulose (J. Aviv et al., 1972 *Proc. Natl. Acad. Sci.* 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and slowly passed through an oligo (dT) cellulose column previously equilibrated with binding buffer (500 mM NaCl, 10 mM Tris, 1 mM EDTA, pH 7.5) The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and AMV reverse transcriptase employing the method of H. Okayama et al., 1983 *Mol. Cell Biol.* 3:280, incorporated herein by reference.

Other methods of preparing cDNA libraries are, of course, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Pat. No. 4,518,584, filed Dec. 20, 1983, and assigned to the same assignee, incorporated herein by reference.

As mentioned above, cDNA libraries are commercially available. A particularly useful library is sold by Clontech (Catalog number #L H1008). It is a lambda gt11 human placenta cDNA library made from total poly (A+) messenger RNA.

4. Identification of GAP DNA Sequences

The oligonucleotide probes described above, GW13, GW15, GW17 and GW19 were used to screen the commercially available Clontech library. The library was plated at about 50,000 plaques per plate using 17 plates. Thus, about 850,000 plaques were screened using the plaque hybridization procedure. While a variety of such procedures are known, a description of the preferred procedure follows. Each 150 mM plate was replicated onto duplicate nitrocellulose filter papers (S & S type BA-85). DNA was fixed to the filter by sequential treatment for 5 minutes with 0.5 N NaOH plus 1.0M NaCl; 1.5M NaCl plus 0.5M Tris-HCl pH 8; and 20 mM Tris plus 2 mM EDTA pH 8. Filters were air dried and baked at 80° C. for 2 hours.

The duplicate filters were prehybridized at 55° C. for 2 hours with 10 ml per filter of DNA hybridization buffer, 5×SSC, pH 7.0, 5×Denhardt's solution (polyvinylpyrrolidone, plus Ficoll and bovine serum albumin; 1×0.02% of each), 50 mM sodium phosphate buffer at pH 7.0, 5 mM EDTA, 0.1% SDS, and 100 µg/ml yeast RNA. The prehybridization buffer was removed and the samples were hybridized with a mixture of kinased probes under conditions which depend on the stringency desired. About 2×10⁶ cpm/ml total was used. Typical moderately stringent conditions employ a temperature of 42° C. plus 50% formamide for 24–36 hours with 1–5 ml/filter of DNA hybridization buffer containing probe. For higher stringencies high temperatures and shorter times were employed. The preferred hybridization conditions consisted of hybridizing the probes to the filters in 5×SSC (standard saline citrate), Denhardt's solution, 50 mM NaPO₄ pH 7.0, 5 mM EDTA, 0.1% SDS, and 100 mg/ml yeast RNA at 55° C. overnight. Next, the filters were washed twice, 30 minutes each wash, at room temperature with 2×SSC, 0.1% SDS and 50 mM sodium phosphate buffer pH 7, then washed once with 2×SSC and 0.1% SDS at 50° C., and air dried. Finally, the filters were autoradiographed at −70° C. for 36 hours.

The autoradiographic results revealed a single positive plaque. Using the washing and hybridization conditions described above, several lambda gt11 plaque purified isolates were identified and picked. Viral DNA was obtained from one of these, termed GAP 6, as follows. GAP 6 was plated at high density on a lawn of *E. coli* strain Y 1090 (r). Following lysis of the *E. coli*, phage particles were eluted into S M buffer (0.1M NaCl 8.1 mM MgSO₄ 50 mM Tris-HCl pH 7.5 0.01% Gelatin) by covering the *E. coli* with buffer and incubating the plate in the cold for several hours. The lysate containing phage particles was centrifuged at 11,500×g for 20 minutes to remove cellular debris, and the resulting supernatant titered using standard techniques. A titer of 2×10¹⁰ PFU/ml was determined. Finally, phage DNA was isolated by the procedure of Maniatis et al., above.

5. Characterization of GAP 6

GAP 6 was subcloned into a suitable vector in order to characterize the DNA both as to Eco RI restriction sites, and partial DNA sequence. Although GAP 6 DNA can be cloned into a variety of vectors, in the instant invention it was cloned into M13. More specifically GAP DNA was cloned into a M13 vector as follows. GAP 6 DNA was treated with Eco RI enzyme which produced two fragments, about 2.0 kb and 0.24 kb. These fragments were isolated using standard agarose gel techniques, and ligated into M13mp18. The M13 vector was designed so that vectors without DNA inserts show up blue under the proper culture conditions, whereas vectors with a DNA insert are clear.

The ligated M13mp18 phage were transduced into frozen competent *E. coli* K12 strain DG98 and cultured by plating on media containing $5 \times 10^4$ M isopropyl thiogalactoside (IPTG) obtained from Sigma Chem. (St. Louis, Mo.) and 40 µ/ml X-gal. Non alpha-complementing white plaques were picked onto fresh media. Minicultures were screened for recombinant single strand phage DNA containing inserts.

The white M13 plaques were screened for inserts by direct gel electrophoresis. The latter procedure was conducted essentially as described by J. Messing, 1983 *Methods of Enzymology* 101:20, which is hereby incorporated by reference. Four M13mp18 subclones were identified by this method. Two subclones, GAP 2 and GAP 8, contained the 2 kb fragment in both orientations. The remaining two subclones, GAP 12 and GAP 18, contained the 0.24 kb fragment in both orientations.

The partial DNA sequence of GAP 2 and GAP 8 was determined by the T. Sanger, S. Nicklen, and H. R. Coulson, 1977 *Proc. Natl. Acad. Sci. USA* 74:5463-5467 techniques described above:

oligonucleotides that flank both sides of the Eco RI site. Exemplary of primers useable with lambda gt11 are two 24-base sequencing primers, 1218 and 1222, produced by New England Biolabs. Similarly, primers compatible with lambda gt10 are also available from New England Biolabs, and these are 1231 and 1232. Thus, separate reactions were run with either 1218, 1219, or 1231 and 1232, and the appropriate GAP 6 primer.

The primers are annealed to denatured DNA acid, followed by extension with a suitable DNA polymerase enzyme, such as the large fragment of DNA polymerase I (Klenow), or preferably a DNA polymerase that is stable in the presence of detergents and nucleotides, which results in newly synthesized plus and minus strands containing the target sequence. Alternatively, a thermostable enzyme may be used which is present in thermostable bacteria. The enzyme may be produced using DNA recombinant techniques as described in U.S. patent application Ser. No. 063,509, Filed Jul. 17, 1987now U.S. Pat. No. 4,889 818. Because the newly synthesized sequences are also templates for the primers, repeated cycles of denaturing, primer

```
5' AAAACTCATGC  AAGGGAAGGG  CAAAACCCAG  TATGGTCAGA
   AGAGTTTGTC   TTTGATGATC  TTCCTCCTGA  CATCAATAGA
   TTTGAAATAA   CTCTTAGTAA  TAAAACAAAG  AAAAGCAAAG
   ATCCTGATAT   CTTATTTATG  CGCTGCCAGT  TGAGCCGATT
   ACAGAAAGGG   CATGCCACAG  ATGAATGGTT  TCTGCTCAGC
   TCCCATATAC   CATTAAAAGG  TATTGAACCA  GGGTCCCTGC
   GTGTTCGAGC   ACGATACTCT  ATGGAAAAAA  TCATGCCAGA
   AGAAGAGTAC   AGTGAATTTA  AAGAGCTTAT  ACTGCAAAAG
   GAACTTCATG   TAGTCTATGC  TTTATCACAT  3'(SEQ ID NO: 15)
```

6. Identification of GAP DNA Sequences Longer Than GAP 6

General Technique: A novel procedure was used to identify plaques that contain GAP cDNA inserts larger than those present in GAP 6 which consisted of elucidating inserts present in either the lambda gt11 library described above, or a lambda gt10 library described below. The procedure consisted of synthesizing cDNA inserts using DNA oligonucleotides having sequences complementary to the 5' region of GAP 6, and oligonucleotide primers that flank the EcoRI insertion sites of lambda gt11, or lambda gt10, using the polymerase chain reaction, or PCR. The newly identified PCR products were sequenced, and accordingly DNA probes were synthesized having sequences 5' of GAP 6. These probes were, in turn, used to identify plaques containing larger GAP cDNA inserts. The procedure was repeated several times using as probes, DNA sequences progressively further 5' of GAP 6 identified from each round of newly synthesized cDNA inserts.

PCR is described in U.S. Pat. Nos. 4,683,202 and 4,683,195, both of which are hereby incorporated in their entirety. In general, the synthesis/amplification of DNA sequences by PCR involves an enzymatic chain reaction that produces, in exponential quantities, a specific DNA sequence, provided that the termini of the sequence are known in sufficient detail so that oligonucleotide primers can be synthesized which will hybridize to them, and that a portion of the sequence is available to initiate the chain reaction. One primer is complementary to the negative strand, and the other is complementary to the positive strand. As applied to the instant invention, the primers employed are complementary to the 5' end of GAP 6, and are complementary to and flank the Eco RI sites of lambda gt11, or lambda gt10. Because the orientation of a particular cDNA insert in either vector is not known, it was necessary to run separate reactions with annealing and extension results in exponential accumulation of the region defined by the primer. PCR thus produces discrete nucleic acid duplexes of cDNA inserts having termini corresponding to the ends of the specific primers employed.

Although PCR can be performed using a variety of reaction conditions, as scribed in the references presented above, the preferred reaction conditions are as follows. Plaques that hybridize to a particular probe are eluted into either 0.5ml of water, or SM buffer, and 50 µl of the eluate combined with 10 µl of 10×PCR buffer, 1.5µl) of 10 mM dNTP's, 1 µl of a first and second primer, each at a concentration of about 20 pmoles, 0.2 µl of Taq polymerase equivalent to 1 unit of activity. The final volume is 100 µl. PCR 10×buffer consists of 500 mM KCl, 200 mM Tris-HCl, pH 8.4, 25 mM $MgCl_2$ and 1 mg/ml.

GAP encoding sequences: Gap 6 DNA was sequenced, and an oligonucleotide probe based on the sequence, GW50, synthesized, radiolabelled, and used to rescreen the Clontech lambda gt11 library, and to screen a second cDNA library made from K562 cells. K562 cDNA was cloned in lambda gt10, and a description of this library is presented by Mes-Masson et al., 1986, in the *Proceedings of the National Academy of Sciences*, 83, 9768. This publication is hereby incorporated by reference in its entirety. The oligonucleotide, GW50, has the following sequence: 5' TTTAAATTCACTGTACTCTTCTTCTGGCATGAT 3' (SEQ IN NO: 16)

Hybridization of GW50 to either library was conducted as described above with the exception that the washing steps after the hybridization were more stringent. Specifically, the filters containing plaques were washed twice, for 15 minutes each wash, with 2×SSC containing 0.1% SDS at room temperature and then two additional washes, for 15 minutes each, with 0.2×SSC containing 0.1% sodium dodecyl sulfate at 55° C. Autoradiography of the filters prepared from the Clontech library revealed 160 positive plaques, while only one plaque was detected from the K562 library.

Using the sequence of GAP 6, DNA primers, LC121 and LC122, with sequences complementary to the 5' region of GAP 6, were synthesized.

LC121 5' GAGGAAGATCATCAAAGACAAACTCT 3' (SEQ ID NO: 17)

LC122 5' TCTGTAATCGGCTCAACTGGCAGCG 3' (SEQ ID NO: 18)

LC121 corresponds to the 5' end of GAP 6 in the anti-sense direction.

The 163 positive plaques from the Clontech library, and the one positive plaque from the K562 library, were removed from agarose plates using a Pasteur pipette, and eluted into 0.5 ml of SM buffer for 30 minutes. Each isolate was then PCR processed as described above using LC121 in combination with the appropriate lambda primers. Typically, a denaturation step was run for 2 minutes at 94° C., followed by an annealing step for 30 seconds at 55° C., and an extension step for 5 minutes at 72° C. The reaction was most often run for 30 cycles. The resulting amplified cDNA inserts were sequenced.

Sequencing can be performed using the techniques referred to above, or by direct sequencing of single stranded DNA produced by PCR. The use of PCR to generate single stranded DNA is described in a co-pending U.S. patent application, Ser. No. 248,896, titled "Method for Generating Single Stranded DNA by the Polymerase Chain Reaction", Filed on Sep. 23, 1988,now U.S. Pat. No. 5,066,584. This patent application is hereby incorporated by reference in its entirety.

Typically about 50 µl of the PCR reaction was separated on a 1% agarose TAE gel, the region of the gel containing the amplified products excised, and the PCR products extracted from the agarose and suspended in about 10 µl–20 µl of TE buffer. Generally about one tenth of this volume was subjected to asymmetric PCR amplification. The reaction conditions employed are described in the above cited patent application. The primers were typically used in a ratio of about 100:1, or about 50:0.5 pmoles.

Using LC121, 14 of the 163 lambda gt11 plaques were found to have an additional 320, or greater number of base pairs 5' of GAP 6, while the single plaque isolated from the K562 lambda gt10 library, referred to as K16, was determined to have a cDNA insert consisting of GAP 6 plus an additional 700 base pairs 5' thereto. Based on the latter sequence, several additional oligonucleotides, LC136, LC138, and LC140 were synthesized and used in conjunction with LC121 to again screen the 163 plaques from the Clontech library. The primers have the following sequences:

LC136 5' CGTAAATTGCAAAATGCCTGCAGAC-CTTG 3' (SEQ ID NO: 19)

LC138 5' GTTTTCCTTTGCCCTTTTTCAGAA-GATAAC 3' (SEQ ID NO: 20)

LC140 5' TGTCATTGAGTACTTGTTCTTGATCCTGC 3' (SEQ ID NO: 21)

Figure 5A:
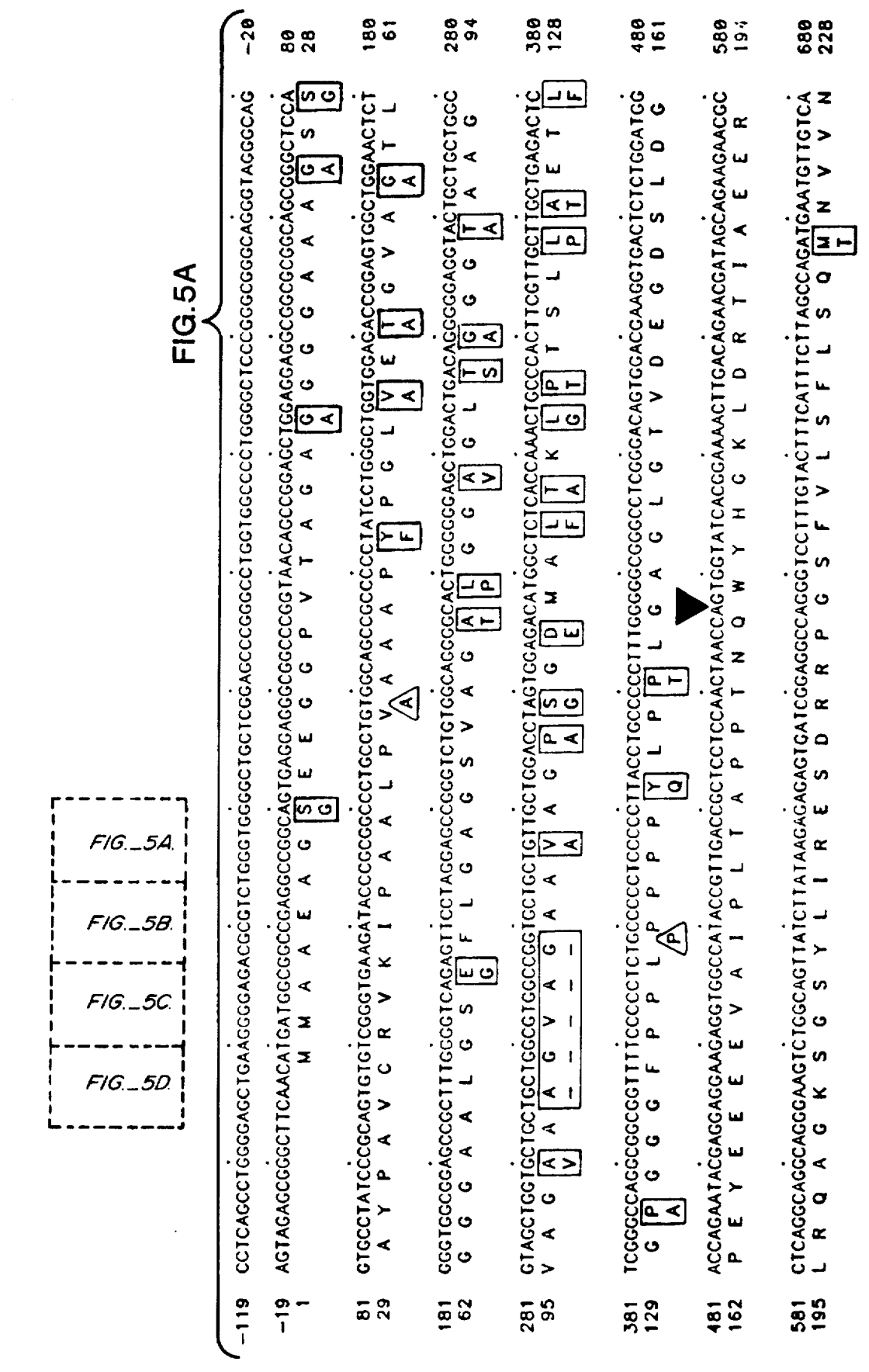
Figure 5B:
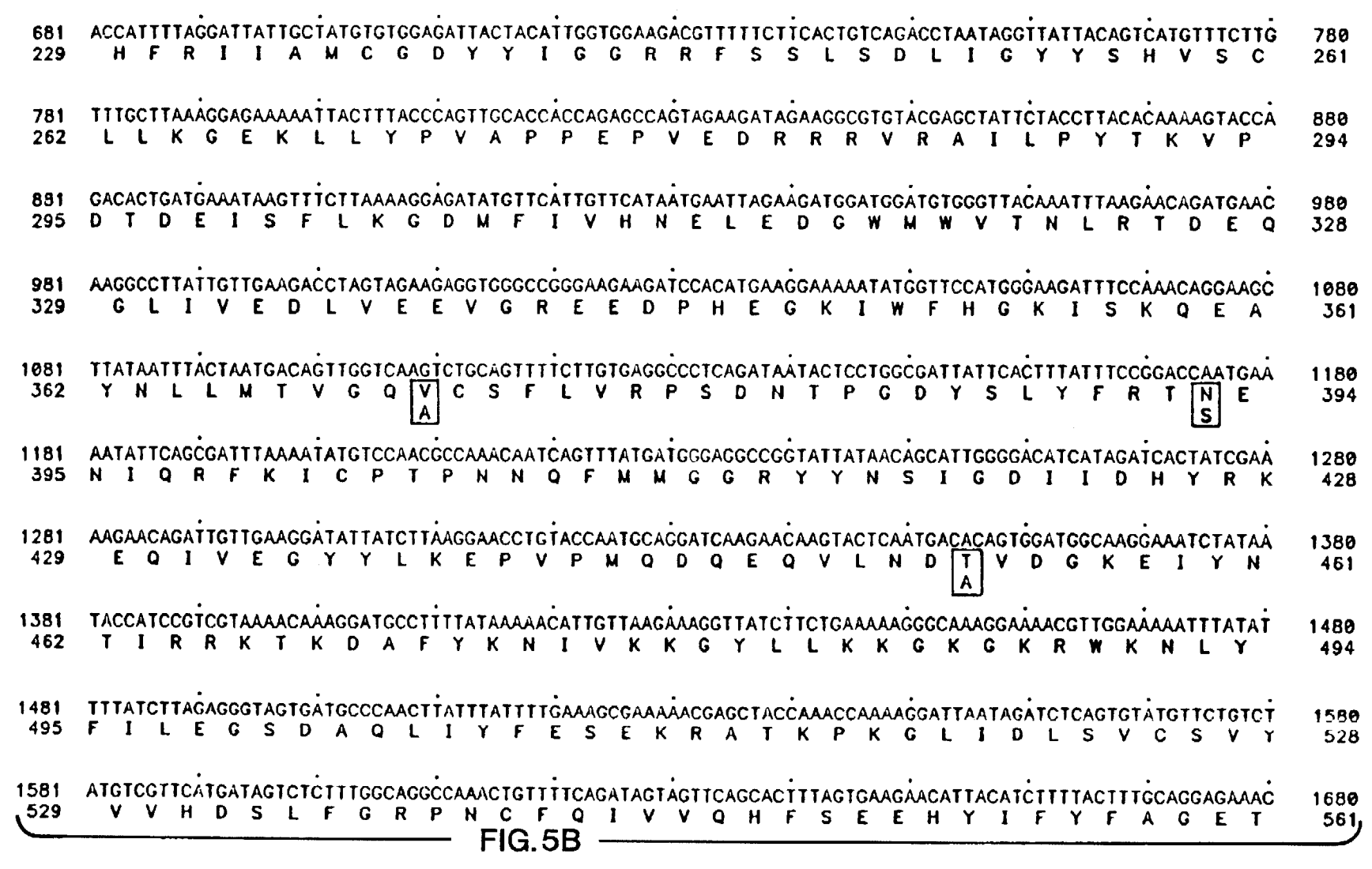

Rescreening the 163 plaques with LC136 revealed that 82 plaques were positive, while rescreening with LC138 plus LC140, revealed that 63 of the plaques were positive. Of the 63 positive plaques, 38 were subjected to PCR using the primers 1218 and LC138; and 1222 and LC138. Of these, six were found to have long stretches of DNA 5' to GAP 6. Sequencing in M13ml8 revealed that they represent different length fragments of the same type of transcript. Two of the clones were studied in detail, clone 7 and clone 101. Clone 101 contained sufficient DNA to encode a protein of 1047 amino acids, which would have a molecular weight of 116,000 daltons. This is similar to the molecular weight of the GAP protein purified from human placenta as described above. Thus, clone 101 contains the full length GAP cDNA. Clone 101 was sequenced, and the sequence is shown in FIG. 5. Clone 7 was also sequenced, and shown to have the identical sequence as clone 101 but lacking 33 base pairs from the 5' end.

Figure 6:
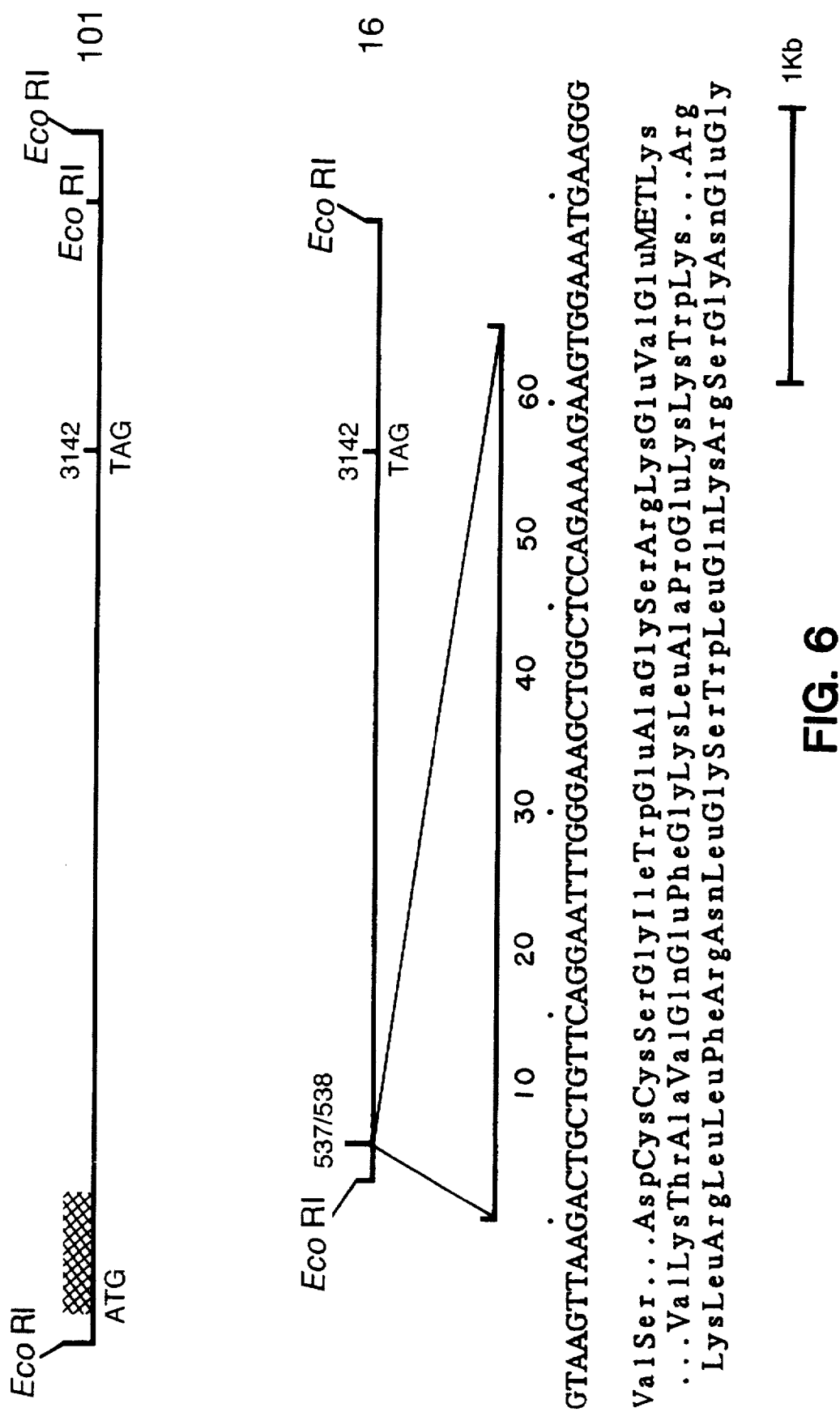
FIG. 6 presents the DNA sequence of the lambda clones, clone 16 and clone 101.

In addition to the above, two plaques were identified from the 163 plaques initially determined to be positive with GW50 that contained cDNA inserts consisting of an additional 65 base pairs inserted between nucleotides 537 and 538 of clone 101. One of the two clones, clone 16, lacks the first 180 amino acids of clone 101, while the other clone, clone "Sleepy", lacks at least the first 180 amino acids, and additionally has a truncated 3'end at about base 2448 of clone 101. The DNA sequence of the 65 base pair insert (SEQ ID NOS: 9, 10, 26 and 27)is shown in FIG. 6 for clone 16.

7. Expression of GAP

Figure 7A:
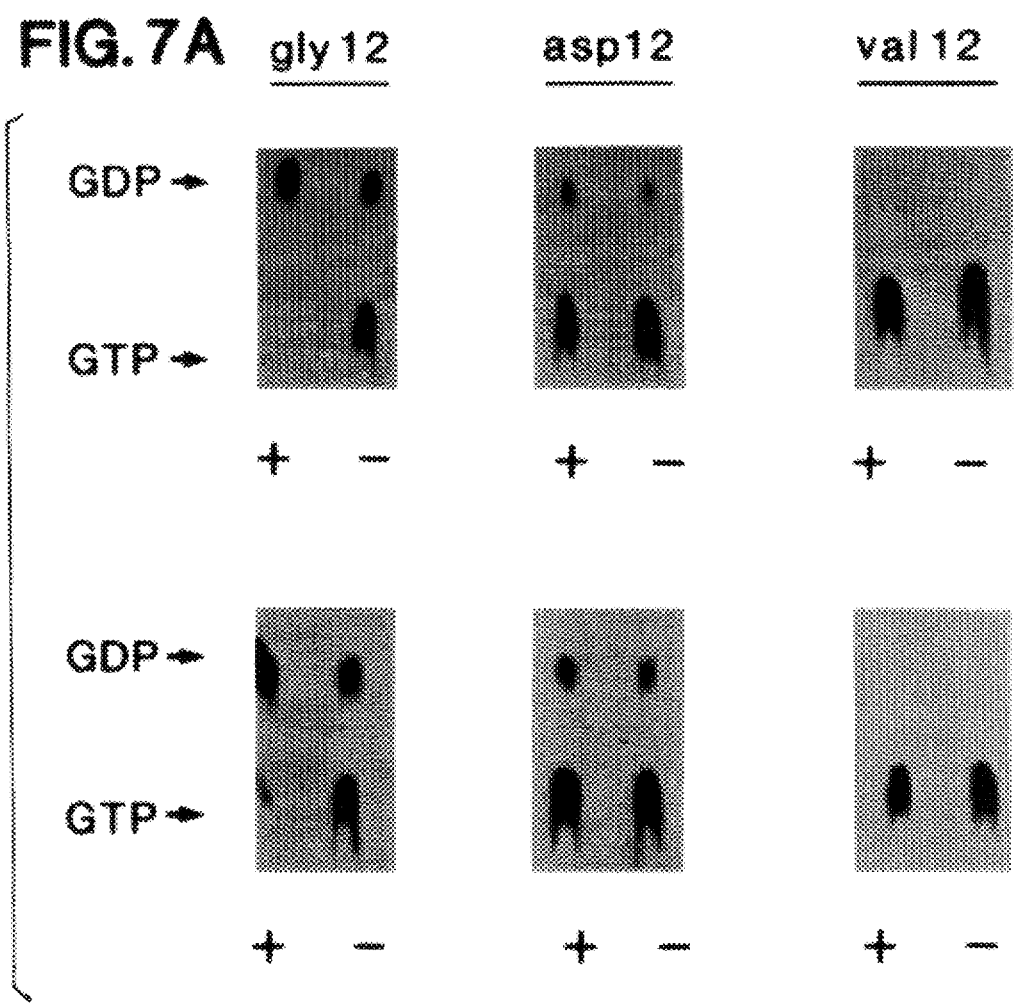
FIG. 7 shows the results of GAP assays conducted in the presence of lysates prepared from lambda lysogens of clones 7 (top panel A, top section) and 101 (top panel); A, bottom section and of Sf9 cell lysates transfected with pAcC121-GAP 5 (bottom panel).
Figure 7B:
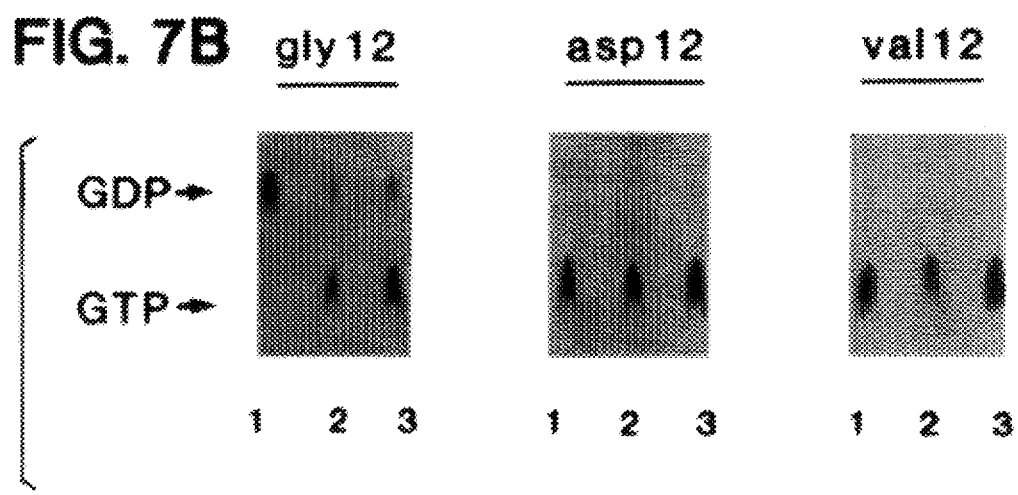

Lambda lysogens: GAP activity was detected from lysates of lambda lysogens of clones 7, 16, and 101. Lysogens were generated in *E. coli* strain Y1089. The procedures for growing, inducing, harvesting, and lysing the cells is described in T. Huynh et al., in "DNA Cloning Techniques: A Practical Approach", D. Glover, Ed. (IRL press, Oxford, 1985) pp 49–78. This publication is hereby incorporated by reference in its entirety. Briefly, supernatants obtained from lysates were dialyzed into GAP assay buffer consisting of 20 mM Tris-HCl, pH 7.0, 1 mM MgCl$_2$, 0.1 mM DTT, 0.1% NP40, 100 µM PMSF, and GAP activity measured using the TLC-based GTPase assay described above. 2.2 µM of either normal N-ras p21 protein having glycine at position 12, or mutant p21 proteins wherein glycine is substituted with aspartic acid or valine, were incubated with 0.25 µM [alpha-32P] GTP (800 Ci/mmole) for 15 minutes at 37° C. in the presence or absence of lambda lysate. As discussed earlier, the mutant p21 proteins have transforming activity and do not exhibit significant GAP stimulatable GTPase activity. About 10 µl of lysate or GAP assay buffer was added, and after 1 hour at room temperature, p21 was immunoprecipitated and associated nucleotides analyzed by chromatography on PEI cellulose in 1M LiCl. An additional control was run for GAP activity; it consisted of testing an irrelevant lysogen lysate, specifically lambda gt11 lacking a cDNA insert. The results are shown in FIG. 7 for clones 7 and 101. The upper part of panel A shows the results for clone 7, while the lower region of the panel shows the results for clone 101. It is apparent that lysates from both clones stimulate the hydrolysis of GTP to GDP in the presence of normal p21, but not in the presence of mutant p21 proteins. Moreover, when GAP buffer is substituted for normal p21, or the mutants, there was no effect on GTP hydrolysis. The irrelevant lysogen lysate also did not support GTP hydrolysis.

Transfection of Spodoptera frugiperda: The full length cDNA insert in clone 101 was expressed in insect cells, *Spodoptera frugiperda*. The insect cell line, Sf9, was transfected with a baculovirus expression vector, pAcC12, containing the GAP encoding Eco R1 fragment of clone 101, and GAP activity measured in cell extracts.

The baculovirus vector, pAcC12, was constructed from preexisting vectors, particularly pAc311 and pAc373, as described by Luckow and Summers in *Biotechnology*, Vol. 6, p. 47 (1988); U.S. Pat. No. 4,745,051; and EPA 127,839.

Figure 8:
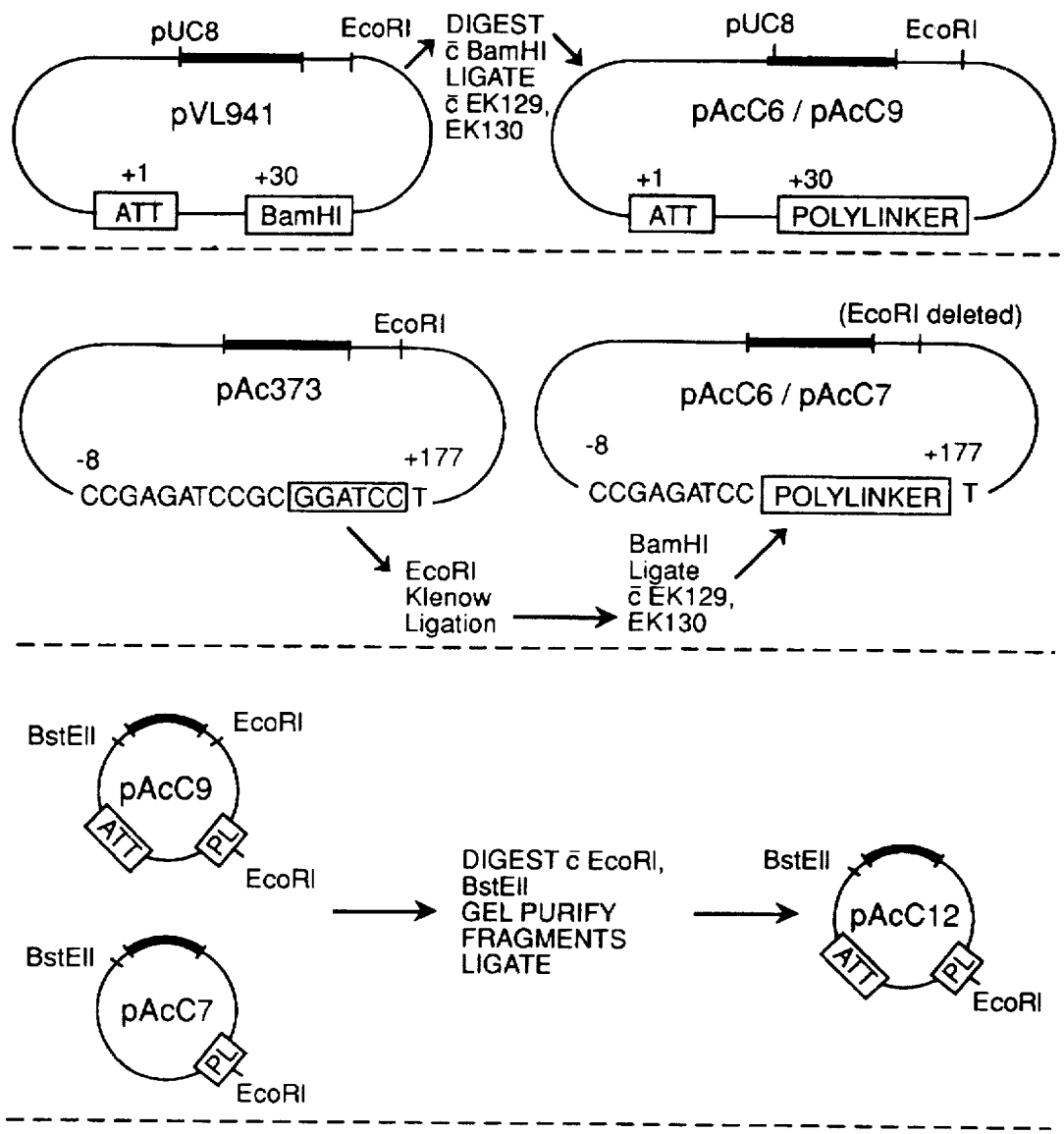
FIG. 8 shows the construction of pAcC12.

Additional details are presented by Summers and Smith in "A Manual of Methods for Baculovirus Vectors and Insect Cell Culture Procedures", Texas Agricultural Experiment Station Bulletin No. 1555, May, 1987. All of these references are hereby incorporated in their entirety. pAcC12 was constructed as described below, and as shown in FIG. 8 (SEQ ID NOS: 11–18. The transfer vector pAc311 was site-directed mutagenized using M13 mutagenesis techniques to convert the polyhedrin gene initiation codon, ATG, to ATT. The resulting vector was designated pVL941, and is described in detail by Luckow and Summers, 1989 *Virology* 170 (1) :31 titled High Level of Expression of Non-Fused Foreign Genes with Autographa Californica Nuclear Polyhedrosis Virus Expression Vectors". A polylinker was inserted into pVL941 at a unique BamHI site 30 base pairs downstream of the ATT sequence. pVL941 was digested with Bam HI, and the polylinker, consisting of two complementary self-annealed oligomers, EK 129 and EK130, having the sequences shown below, ligated to produce the vectors pAcC8 and pAcC9 that carry the polylinker in different orientations. The polylinker has a restriction site for Eco RI, as well as for other restriction enzymes.

Tris HCl, pH 8.0, and 150 mM NaCl. The extract was centrifuged for 15 minutes at 15,000xg and aliquotes diluted into GAP assay buffer, and assayed for GAP activity as described above. Methods for growing Sf9 cells are well known in the art, and detailed procedures for their cultivation can be found in M. Summers and G. Smith in "A Manual of Methods for Baculovirus Vectors and Insect Cell Culture Procedures", Texas Agricultural Experiment Station, Bulletin No. 1555 (May, 1987) or in EPO 127,839 to G. E. Smith and M. D. Summers. Preferred media and culturing conditions can be found in co-pending, commonly owned U.S. patent applications Ser. No. 77,181, titled "Airlift Insect Cell Culture ," filed Jul. 24, 1987, abandoned, continued-part in U.S. patent application Ser. No. 427,035, filed Oct. 24, 1989, abandoned, continued in U.S. patent application Ser. No. 830,513, filed Jan. 30, 1992; Ser. No. 77,303, now titled "Serum Free Media for the Growth of Insect Cells and Expression of Products Thereby," now U.S. Pat. No. 5,024,947; and Ser. No. 77,189, titled "Lipid Microemulsions for Culture Media," filed Jul. 24, 1987, abandoned, continued-in-part in U.S. patent application Ser. No. 248,830, filed Sep. 24, 1988, abandoned, continued in

EK 129:
5'GATCCACCATGGAGCTCGAGATCTAGAATTCTGCAGCCCGGGTACCGATC 3'(SEQ ID NO: 22)

EK 130:
5'GATCGGTACCCGGGCTGCAGAATTCTAGATCTCGAGCTCCATGGTGGATC 3'(SEQ ID NO: 24)

Because pAcC8 and pAcC9 have two Eco RI restriction sites, one in the polylinker and the other in the plasmid DNA as shown in FIG. 8, it was desirable to remove the plasmid Eco RI site so that the Gap Eco RI encoding fragment of clone 101 could be inserted into the polylinker site. This was achieved using the transfer vector pAc373. pAc373 is similar to pAc311 except that the nucleotide sequences spanning the polyhedrin start codon differ. Thus, the Eco RI site was removed from pAc373 by digesting the vector to completion with Eco RI, and the ends made blunt using the Klenow fragment under the appropriate reaction conditions. Following ligation and transformation into *E. coli* DH 5, colonies were identified that lacked the Eco RI site by restriction analysis of miniprep DNA.

pAc373 lacking the Eco RI site was further modified by incorporating the polylinker consisting of the oligomers, EK129 and EK130, shown above, by digesting the vector with Bam HI, followed by ligating the oligomers. The resulting vectors, pAcC6 and pAcC7, contain the polylinker in different orientations.

The final construct, pAcC12, was generated from pAcC7 and pAcC9 as shown in FIG. 8. These vectors contain the polylinker in the same orientation. Both vectors were digested with Bst EII and Eco RI and the resulting fragments electrophoretically purified. The Bst EII/Eco RI fragment of pAcC7 containing the pUC 8 sequences, and partial polylinker sequences was ligated to the large BstEII/Eco RI fragment of pAcC9. This latter fragment contains the ATT sequence and the remaining polylinker sequences.

The transfer vector, pAcC12, has the Eco RI GAP fragment of clone 101 inserted in both orientations. The correct orientation was designated pAcC12 GAP 5, while the incorrect orientation was designated pAcC12GAP 101–7. About 2 µg of either plasmid was transfected into 2×10⁵ Sf9 cells, the cells grown for 4 days, isolated by centrifugation, and cell extracts made by solubilizing the cell pellet. The preferred solubilization solution consists of 0.5% NP40, 10 mM U.S. patent application Ser. No. 829,610, filed Jan. 30, 1992. patent applications are hereby incorporated by reference. FIG. 7, panel B shows the results. The effect of pAcGAP 5 and pAcGAP 101–7 are shown in lanes 1 and 2, respectively; lane 3 presents a buffer control. Note that pAcGAP 5-stimulates normal ras p21 GTPase activity, whereas it is without effect on the p21 mutants. In contrast, there is no stimulation of GTPase activity by pAcGAP 101–7 of either normal ras p21 or the mutants.

It is important to note that baculovirus can be recovered from Sf9 cells transfected with the above described transfer vectors using the techniques described by Summers and Smith, above. Such virus can be employed to transform cells directly with the appropriate GAP clone.

8. Diagnostic Uses of GAP Sequences

The GAP DNA sequences described herein can be used to produce GAP, which, in turn, can be used to produce antibodies to GAP. These antibodies may be used to isolate GAP using antibody purification techniques generally known in the art. Since GAP is one reagent employed in assaying for the presence of normal ras p21, as described above, especially in tumors thought to result from the overexpression of ras p21, and is now available only in limited amounts because of the burdensome purification methods used to obtain it, the availability of large amounts of GAP will be a valuable addition to present cancer diagnostic methods.

The GAP DNA sequences disclosed herein may also be used to determine the number of copies of the GAP gene present per cell in various types of cancers, that is to say, whether the gene is amplified. It is applicant's belief that tumors thought to be causally related to ras expression, overexpress GAP via gene amplification. Thus, the GAP DNA sequences disclosed herein can be used to measure the degree of overamplification, and diagnostic and prognostic correlations established.

The GAP DNA sequences can be used to measure the level of amplification following techniques generally known in the art. D. Slamon et al., 1987 *Science* 235:177; U.S. Pat. No. 4,542,092 and U.S. Pat. No. 4,699,877; R. Schimke, 1982 *Gene Amplification*, Cold Spring Harbor Laboratory. These publications are hereby incorporated by reference in their entirety. GAP gene amplification can be measured directly using established DNA hybridization techniques. DNA is prepared from human tumor tissue as described by Maniatis et al., and Slamon et al., above, or J. Southern, 1975 *Mol. Biol.* 98:503, and reacted with labeled GAP DNA. GAP 6, GAP 2 or GAP 8 sequences may be used. The entire sequence may be used, or short nucleotide sequences derived therefrom. Normally, a sequence should have at least about 14 nucleotides, and preferably at least about 18 nucleotides. Various labels may be employed to label the GAP sequences, most commonly radionuclides, particularly 32 P are used. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescent molecules, enzymes, or the like. Alternatively, antibodies may be employed which can recognize specific duplexes, including DNA duplexes, RNA duplexes and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected. The DNA probe labelling procedures are known in the art. See, Maniatis et al., above.

A suitable DNA preparation and hybridization procedure to determine the number of GAP genes per cell using dilutional analysis as described by Slamon et al., above, consists of extracting and digesting tumor DNA using the procedure of Maniatis et al., above, followed by subjecting about 10–15 μg of EcoRI digested DNA to electrophoresis in 0.8% agarose gel, or dilutions of the digested DNA and transferring the DNA onto nylon filter papers. The filters are baked in a vacuum oven for 2 hours at 80° C., prehybridized in 5×SSC solution containing 50% formamide, 10% dextran sulfate, 0.1% SDS, denatured salmon sperm DNA (1 mg/ml), and 4×Denhardt's solution for 12 hours. The DNA can then be hybridized in the same solution containing 32 P-labeled nick-translated GAP 8 probe with a specific activity of about 1×10$^8$ cpm/μg DNA, or about 2×10$^6$ cpm/ml. Optimal hybridization and washing conditions can be especially determined, however results may be apparent if hybridization occurs for 48 hours at 42° C., and the filters are washed in succession as follows: 2×SSC for 20 minutes at room temperature; two washes of 30 minutes each in 2×SSC, 0.1% SDS at 65° C.; and one wash of 30 minutes in 0.5×SSC, 0.1% SDS at 65° C. Filters can then be exposed to x-ray film for autoradiography, and the degree of amplification ascertained using established methods, including soft laser densitometry scanning.

Using the above techniques, a correlation may be observed wherein individuals with tumors that have 2–4 copies of GAP enjoy a favorable diagnosis and are unlikely to develop an aggressive malignancy, whereas tumors with 4 or more copies are likely to have aggressive malignancies, and require extensive medical treatment.

In addition to directly detecting GAP gene amplification by the foregoing procedures, amplification may also be detected indirectly by measuring GAP gene messenger RNA levels with labelled GAP DNA sequences. The procedures generally applicable to this method are described in Maniatis et al., above, and in U.S. Pat. No. 4,699,877.

Deposit of Biological Materials: The following plasmids have been deposited with the American Type Culture Collection , 12301 Parklawn Drive, Rockville Md 20852, on Oct. 11, 1988.

| Designation | ATCC No. | CMCC No. |
| --- | --- | --- |
| pAcC GAP 5 (pAcC12 GAP 5) | 67821 | 3437 |
| pGAP 16-4 (Clone 16) | 40503 | 3479 |
| pGAP-SLE1 (Clone Sleepy) | 40504 | 3480 |

The deposit, pAcC GAP 5 (pAcC12 GAP 5), CMCC 3437, is an *Escherichia coli* plasmid. The other two deposits are bacteriophage deposits.

Having generally described the invention, it will be appreciated that the scope of the invention is limited only by the appended claims, and not by the particular materials and methods described above.

We claim:

1. An isolated DNA comprising the contiguous nucleotide sequence shown in SEQ ID NO: 7, said contiguous nucleotide sequence encoding a polypeptide possessing GAP activity.

2. A DNA according to claim 1 wherein said contiguous nucleotide sequence is operably linked to a control sequence which regulates the expression of said polypeptide in transformed host cells.

3. The DNA of claim 2 wherein said host cells are procaryotic or eucaryotic cells.

4. The DNA of claim 3 wherein said host cells are *Escherichia coli*.

5. The DNA of claim 3 wherein said host cells are insect cells.

6. The DNA of claim 5 wherein said insect cells are *Spodoptera frugiperda* cells.

7. A baculovirus transfer vector comprising the DNA of claim 1.

8. An isolated DNA comprising the nucleotide sequence of Clone Sleepy having ATCC No. 40504.

9. An isolated DNA encoding a polypeptide possessing GAP activity, said DNA comprising a contiguous portion of the nucleotide sequence shown in SEQ ID NO: 7, said portion encoding a polypeptide possessing GAP activity.

10. An isolated DNA comprising a contiguous, polypeptide-encoding insert of Clone 16 having ATCC No. 40503, said polypeptide having GAP activity.

11. An isolated DNA encoding a polypeptide possessing GAP activity, wherein the polypeptide has a molecular weight of about 115,000–120,000 daltons as determined by sodium dodecyl sulfate polyacrylamide gel electrophoresis run under reducing conditions.

12. An isolated DNA encoding a polypeptide possessing GAP activity and operatively linked to control sequences which regulate the synthesis of said DNA and the expression of said polypeptide in transformed host cells.

13. An isolated DNA encoding a polypeptide having the amino acid sequence shown in SEQ ID NO: 8, said polypeptide possessing GAP activity.

14. A baculovirus transfer vector, wherein said vector is pAcC12 GAP 5 having ATCC No. 67821.

15. An isolated DNA comprising a contiguous, polypeptide-encoding insert of pAcC12 GAP 5 having ATCC No. 67821, wherein said polypeptide possesses GAP activity.

16. A vector comprising a DNA according to claim 13.

17. A host cell transformed with a vector according to claim 16.

18. A DNA according to claim 13 having the contiguous nucleotide sequence corresponding to nucleotides 119 to 3259 of SEQ ID NO: 7.

19. An isolated DNA encoding a polypeptide possessing GAP activity, said polypeptide having a contiguous amino acid sequence corresponding to amino acid residues 181 to 1047 of SEQ ID NO: 8.

20. An isolated DNA according to claim 19, said DNA comprising nucleotides 659 to 3259 of SEQ ID NO: 7.

21. An isolated DNA having the contiguous nucleotide sequence corresponding to nucleotides 1 to 3456 of SEQ ID NO: 24.

22. An isolated DNA encoding a polypeptide possessing GAP activity, said DNA comprising a contiguous nucleotide sequence corresponding to nucleotides 43 to 2709 of SEQ ID NO: 24.

23. An isolated and GAP-specific polynucleotide comprising a contiguous portion of at least 14 nucleotides of a nucleotide sequence selected from the group consisting of SEQ ID NO: 7 and the sequence complementary to SEQ ID NO: 7, said isolated polynucleotide capable of specifically hybridizing under high stringency hybridization conditions to a DNA encoding a polypeptide possessing GAP activity, or to the non-coding strand complementary to said DNA.

24. A polynucleotide according to claim 23 wherein said DNA is a cDNA having the nucleotide sequence corresponding to nucleotides 119 to 3259 of SEQ ID NO: 7.

25. A polynucleotide according to claim 24, said polynucleotide having a nucleotide sequence comprising a contiguous portion of at least 18 nucleotides of the nucleotide sequence of SEQ ID NO: 7.

26. A polynucleotide according to claim 25 wherein said contiguous portion is at least 29 nucleotides in length.

27. A polynucleotide according to claim 24, said polynucleotide having a nucleotide sequence that is complementary to a contiguous portion of at least 18 nucleotides of the nucleotide sequence of SEQ ID NO: 7.

28. A polynucleotide according to claim 27 wherein said contiguous portion is at least 29 nucleotides in length.

29. A polynucleotide according to claim 23 comprising a nucleotide sequence selected from the group consisting of SEQ ID NO: 15, SEQ ID NO: 16, SEQ ID NO: 17, SEQ ID NO: 18, SEQ ID NO: 19, SEQ ID NO: 20, and SEQ ID NO: 21.

30. An isolated polynucleotide comprising a contiguous portion of at least 18 nucleotides of a nucleotide sequence selected from the group consisting of SEQ ID NO: 7 and the sequence complementary to SEQ ID NO: 7, said isolated polynucleotide capable of hybridizing under moderately stringent conditions to a DNA encoding a polypeptide possessing GAP activity, or to the non-coding strand complementary to said DNA, said moderately stringent hybridization conditions comprising a hybridization temperature of 42° C., a hybridization buffer comprising 50% formamide, and a hybridization period of 24–36 hours.

31. An isolated polynucleotide comprising at least 14 nucleotides and capable of hybridizing under stringent hybridization conditions to a DNA encoding a polypeptide possessing GAP activity, or to the non-coding strand complementary to said DNA, said DNA having the sequence set forth in SEQ ID NO: 7.

32. A polynucleotide according to claim 31, said polynucleotide having a nucleotide sequence comprising a contiguous portion of at least 18 nucleotides of the nucleotide sequence corresponding to nucleotides 119 to 3259 of SEQ ID NO: 7.

33. A polynucleotide according to claim 31, said polynucleotide having a nucleotide sequence comprising a contiguous portion of at least 29 nucleotides of the nucleotide sequence of SEQ ID NO: 7.

34. An isolated DNA encoding a polypeptide possessing GAP activity, said DNA capable of being isolated by a method comprising the steps of:

providing a DNA library comprising human genomic DNA or human cDNA;

screening said library with a polynucleotide according to claim 23, wherein said screening is performed under stringent hybridization conditions, and wherein said polynucleotide is detectably labeled;

detecting a DNA forming a detectable polynucleotide-DNA hybrid with said detectably labeled polynucleotide in said screening step; and isolating said DNA of said detectable polynucleotide-DNA hybrid, wherein said DNA encodes a polypeptide possessing GAP activity.

35. An isolated DNA according to claim 34 wherein said method further comprises the steps of:

expressing said isolated DNA in a host cell to make a recombinant protein encoded by said isolated DNA; and assaying said recombinant protein for GAP activity, to identify DNA encoding a polypeptide possessing GAP activity.

36. An isolated DNA according to claim 35 wherein said method further comprises the step of purifying said recombinant protein after said expressing step.

37. An isolated DNA according to claim 34 wherein in said screening step said polynucleotide is a polynucleotide according to claim 26.

38. An isolated DNA according to claim 34 wherein in said screening step said polynucleotide is a polynucleotide according to claim 29.

39. An isolated DNA encoding a polypeptide possessing GAP activity, said DNA capable of hybridizing under stringent hybridization conditions to a polynucleotide selected from the group consisting of a DNA having the nucleotide sequence shown in SEQ ID NO: 7, a DNA having the nucleotide sequence of the non-coding strand complementary to SEQ ID NO: 7, a DNA having the nucleotide sequence shown in SEQ ID NO: 24, and a DNA having the nucleotide sequence of the non-coding strand complementary to SEQ ID NO: 24.

\* \* \* \* \*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ile  Met  Pro  Glu  Glu  Glu  Tyr  Ser  Glu  Phe  Lys
 1              5                          1 0
```

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 22-24
        ( D ) OTHER INFORMATION: "The residues at positions 22-24 are
            TCN or AGY"

( x i ) SEQUENCE DESCRIPTION: SEQ ID NO:2:

ATHATGCCNG ARSARGARTA YNNNGARTTY AAR  33

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ATCATGCCTG AGCAGGAGTA CTCTGAGTTC AAG  33

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ATCATGCCTG AGCAGGAGTA CAGTGAGTTC AAG  33

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

ATCATGCCTG AGGAGGAGTA CTCTGAGTTC AAG  33

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

ATCATGCCTG AGGAGGAGTA CAGTGAGTTC AAG  33

-continued ( 2 ) INFORMATION FOR SEQ ID NO:7:

( i ) SEQUENCE CHARACTERISTICS:
        ( A ) LENGTH: 4307 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 119..3259

( x i ) SEQUENCE DESCRIPTION: SEQ ID NO:7:

```
CCTCAGCCTG GGGAGCTGAA GGGGAGACGC GTCTGGGTGG GGCTGCTCGG AGCCCGGGCC        60

TGGTGGCCCC TGGGGCTCCC GGGCGGGCAG GGTAGGGCAG AGTAGAGCGG GCTTCAAC         118

ATG ATG GCG GCC GAG GCC GGC AGT GAG GAG GGC GGC CCG GTA ACA GCC        166
Met Met Ala Ala Glu Ala Gly Ser Glu Glu Gly Gly Pro Val Thr Ala
  1               5                  10                  15

GGA GCT GGA GGA GGC GGC GCG GCA GCG GGC TCC AGT GCC TAT CCC GCA        214
Gly Ala Gly Gly Gly Gly Ala Ala Ala Gly Ser Ser Ala Tyr Pro Ala
              20                  25                  30

GTG TGT CGG GTG AAG ATA CCC GCG GCC CTG CCT GTG GCA GCC GCC CCC        262
Val Cys Arg Val Lys Ile Pro Ala Ala Leu Pro Val Ala Ala Ala Pro
          35                  40                  45

TAT CCT GGG CTG GTG GAG ACC GGA GTG GCT GGA ACT CTG GGT GGC GGA        310
Tyr Pro Gly Leu Val Glu Thr Gly Val Ala Gly Thr Leu Gly Gly Gly
      50                  55                  60

GCC GCT TTG GGG TCA GAG TTC CTA GGA GCC GGG TCT GTG GCA GGG GCA        358
Ala Ala Leu Gly Ser Glu Phe Leu Gly Ala Gly Ser Val Ala Gly Ala
 65                 70                  75                  80

CTG GGG GGA GCT GGA CTG ACA GGG GGA GGT ACT GCT GCT GGC GTA GCT        406
Leu Gly Gly Ala Gly Leu Thr Gly Gly Gly Thr Ala Ala Gly Val Ala
                  85                  90                  95

GGT GCT GCT GCT GGC GTG GCC GGT GCT GCT GTT GCT GGA CCT AGT GGA        454
Gly Ala Ala Ala Gly Val Ala Gly Ala Ala Val Ala Gly Pro Ser Gly
              100                 105                 110

GAC ATG GCT CTC ACC AAA CTG CCC ACT TCG TTG CTT GCT GAG ACT CTC        502
Asp Met Ala Leu Thr Lys Leu Pro Thr Ser Leu Leu Ala Glu Thr Leu
          115                 120                 125

GGG CCA GGC GGC GGT TTT CCC CCT CTG CCC CCT CCC CCT TAC CTG CCC        550
Gly Pro Gly Gly Gly Phe Pro Pro Leu Pro Pro Pro Pro Tyr Leu Pro
      130                 135                 140

CCT TTG GGG GCG GGC CTC GGG ACA GTG GAC GAA GGT GAC TCT CTG GAT        598
Pro Leu Gly Ala Gly Leu Gly Thr Val Asp Glu Gly Asp Ser Leu Asp
145                 150                 155                 160

GGA CCA GAA TAC GAG GAG GAA GAG GTG GCC ATA CCG TTG ACC GCT CCT        646
Gly Pro Glu Tyr Glu Glu Glu Glu Val Ala Ile Pro Leu Thr Ala Pro
                  165                 170                 175

CCA ACT AAC CAG TGG TAT CAC GGA AAA CTT GAC AGA ACG ATA GCA GAA        694
Pro Thr Asn Gln Trp Tyr His Gly Lys Leu Asp Arg Thr Ile Ala Glu
              180                 185                 190

GAA CGC CTC AGG CAG GCA GGG AAG TCT GGC AGT TAT CTT ATA AGA GAG        742
Glu Arg Leu Arg Gln Ala Gly Lys Ser Gly Ser Tyr Leu Ile Arg Glu
          195                 200                 205

AGT GAT CGG AGG CCA GGG TCC TTT GTA CTT TCA TTT CTT AGC CAG ATG        790
Ser Asp Arg Arg Pro Gly Ser Phe Val Leu Ser Phe Leu Ser Gln Met
      210                 215                 220

AAT GTT GTC AAC CAT TTT AGG ATT ATT GCT ATG TGT GGA GAT TAC TAC        838
Asn Val Val Asn His Phe Arg Ile Ile Ala Met Cys Gly Asp Tyr Tyr
225                 230                 235                 240
```

```
ATT GGT GGA AGA CGT TTT TCT TCA CTG TCA GAC CTA ATA GGT TAT TAC      886
Ile Gly Gly Arg Arg Phe Ser Ser Leu Ser Asp Leu Ile Gly Tyr Tyr
            245             250                 255

AGT CAT GTT TCT TGT TTG CTT AAA GGA GAA AAA TTA CTT TAC CCA GTT      934
Ser His Val Ser Cys Leu Leu Lys Gly Glu Lys Leu Leu Tyr Pro Val
            260             265                 270

GCA CCA CCA GAG CCA GTA GAA GAT AGA AGG CGT GTA CGA GCT ATT CTA      982
Ala Pro Pro Glu Pro Val Glu Asp Arg Arg Arg Val Arg Ala Ile Leu
            275             280                 285

CCT TAC ACA AAA GTA CCA GAC ACT GAT GAA ATA AGT TTC TTA AAA GGA     1030
Pro Tyr Thr Lys Val Pro Asp Thr Asp Glu Ile Ser Phe Leu Lys Gly
            290             295                 300

GAT ATG TTC ATT GTT CAT AAT GAA TTA GAA GAT GGA TGG ATG TGG GTT     1078
Asp Met Phe Ile Val His Asn Glu Leu Glu Asp Gly Trp Met Trp Val
305             310             315                 320

ACA AAT TTA AGA ACA GAT GAA CAA GGC CTT ATT GTT GAA GAC CTA GTA     1126
Thr Asn Leu Arg Thr Asp Glu Gln Gly Leu Ile Val Glu Asp Leu Val
            325             330                 335

GAA GAG GTG GGC CGG GAA GAA GAT CCA CAT GAA GGA AAA ATA TGG TTC     1174
Glu Glu Val Gly Arg Glu Glu Asp Pro His Glu Gly Lys Ile Trp Phe
            340             345                 350

CAT GGG AAG ATT TCC AAA CAG GAA GCT TAT AAT TTA CTA ATG ACA GTT     1222
His Gly Lys Ile Ser Lys Gln Glu Ala Tyr Asn Leu Leu Met Thr Val
            355             360                 365

GGT CAA GTC TGC AGT TTT CTT GTG AGG CCC TCA GAT AAT ACT CCT GGC     1270
Gly Gln Val Cys Ser Phe Leu Val Arg Pro Ser Asp Asn Thr Pro Gly
            370             375                 380

GAT TAT TCA CTT TAT TTC CGG ACC AAT GAA AAT ATT CAG CGA TTT AAA     1318
Asp Tyr Ser Leu Tyr Phe Arg Thr Asn Glu Asn Ile Gln Arg Phe Lys
385             390             395                 400

ATA TGT CCA ACG CCA AAC AAT CAG TTT ATG ATG GGA GGC CGG TAT TAT     1366
Ile Cys Pro Thr Pro Asn Asn Gln Phe Met Met Gly Gly Arg Tyr Tyr
            405             410                 415

AAC AGC ATT GGG GAC ATC ATA GAT CAC TAT CGA AAA GAA CAG ATT GTT     1414
Asn Ser Ile Gly Asp Ile Ile Asp His Tyr Arg Lys Glu Gln Ile Val
            420             425                 430

GAA GGA TAT TAT CTT AAG GAA CCT GTA CCA ATG CAG GAT CAA GAA CAA     1462
Glu Gly Tyr Tyr Leu Lys Glu Pro Val Pro Met Gln Asp Gln Glu Gln
            435             440                 445

GTA CTC AAT GAC ACA GTG GAT GGC AAG GAA ATC TAT AAT ACC ATC CGT     1510
Val Leu Asn Asp Thr Val Asp Gly Lys Glu Ile Tyr Asn Thr Ile Arg
450             455             460

CGT AAA ACA AAG GAT GCC TTT TAT AAA AAC ATT GTT AAG AAA GGT TAT     1558
Arg Lys Thr Lys Asp Ala Phe Tyr Lys Asn Ile Val Lys Lys Gly Tyr
465             470             475                 480

CTT CTG AAA AAG GGC AAA GGA AAA CGT TGG AAA AAT TTA TAT TTT ATC     1606
Leu Leu Lys Lys Gly Lys Gly Lys Arg Trp Lys Asn Leu Tyr Phe Ile
            485             490                 495

TTA GAG GGT AGT GAT GCC CAA CTT ATT TAT TTT GAA AGC GAA AAA CGA     1654
Leu Glu Gly Ser Asp Ala Gln Leu Ile Tyr Phe Glu Ser Glu Lys Arg
            500             505                 510

GCT ACC AAA CCA AAA GGA TTA ATA GAT CTC AGT GTA TGT TCT GTC TAT     1702
Ala Thr Lys Pro Lys Gly Leu Ile Asp Leu Ser Val Cys Ser Val Tyr
            515             520                 525

GTC GTT CAT GAT AGT CTC TTT GGC AGG CCA AAC TGT TTT CAG ATA GTA     1750
Val Val His Asp Ser Leu Phe Gly Arg Pro Asn Cys Phe Gln Ile Val
            530             535                 540

GTT CAG CAC TTT AGT GAA GAA CAT TAC ATC TTT TAC TTT GCA GGA GAA     1798
Val Gln His Phe Ser Glu Glu His Tyr Ile Phe Tyr Phe Ala Gly Glu
            545             550                 555                 560
```

| | | | | | | | | | | | | | | | | |
|---|---|---|---|---|---|---|---|---|---|---|---|---|---|---|---|---|
| ACT | CCA | GAA | CAA | GCA | GAG | GAT | TGG | ATG | AAA | GGT | CTG | CAG | GCA | TTT | TGC | 1846 |
| Thr | Pro | Glu | Gln | Ala | Glu | Asp | Trp | Met | Lys | Gly | Leu | Gln | Ala | Phe | Cys | |
| | | | | 565 | | | | | 570 | | | | | 575 | | |
| AAT | TTA | CGG | AAA | AGT | AGT | CCA | GGG | ACA | TCC | AAT | AAA | CGC | CTT | CGT | CAG | 1894 |
| Asn | Leu | Arg | Lys | Ser | Ser | Pro | Gly | Thr | Ser | Asn | Lys | Arg | Leu | Arg | Gln | |
| | | | 580 | | | | | 585 | | | | | 590 | | | |
| GTC | AGC | AGC | CTT | GTT | TTA | CAT | ATT | GAA | GAA | GCC | CAT | AAA | CTC | CCA | GTA | 1942 |
| Val | Ser | Ser | Leu | Val | Leu | His | Ile | Glu | Glu | Ala | His | Lys | Leu | Pro | Val | |
| | | 595 | | | | | 600 | | | | | 605 | | | | |
| AAA | CAT | TTT | ACT | AAT | CCA | TAT | TGT | AAC | ATC | TAC | CTG | AAT | AGT | GTC | CAA | 1990 |
| Lys | His | Phe | Thr | Asn | Pro | Tyr | Cys | Asn | Ile | Tyr | Leu | Asn | Ser | Val | Gln | |
| | 610 | | | | | 615 | | | | | 620 | | | | | |
| GTA | GCA | AAA | ACT | CAT | GCA | AGG | GAA | GGG | CAA | AAC | CCA | GTA | TGG | TCA | GAA | 2038 |
| Val | Ala | Lys | Thr | His | Ala | Arg | Glu | Gly | Gln | Asn | Pro | Val | Trp | Ser | Glu | |
| 625 | | | | 630 | | | | | 635 | | | | | 640 | | |
| GAG | TTT | GTC | TTT | GAT | GAT | CTT | CCT | CCT | GAC | ATC | AAT | AGA | TTT | GAA | ATA | 2086 |
| Glu | Phe | Val | Phe | Asp | Asp | Leu | Pro | Pro | Asp | Ile | Asn | Arg | Phe | Glu | Ile | |
| | | | | 645 | | | | | 650 | | | | | 655 | | |
| ACT | CTT | AGT | AAT | AAA | ACA | AAG | AAA | AGC | AAA | GAT | CCT | GAT | ATC | TTA | TTT | 2134 |
| Thr | Leu | Ser | Asn | Lys | Thr | Lys | Lys | Ser | Lys | Asp | Pro | Asp | Ile | Leu | Phe | |
| | | | 660 | | | | | 665 | | | | | 670 | | | |
| ATG | CGC | TGC | CAG | TTG | AGC | CGA | TTA | CAG | AAA | GGG | CAT | GCC | ACA | GAT | GAA | 2182 |
| Met | Arg | Cys | Gln | Leu | Ser | Arg | Leu | Gln | Lys | Gly | His | Ala | Thr | Asp | Glu | |
| | | 675 | | | | | ·680 | | | | | 685 | | | | |
| TGG | TTT | CTG | CTC | AGC | TCC | CAT | ATA | CCA | TTA | AAA | GGT | ATT | GAA | CCA | GGG | 2230 |
| Trp | Phe | Leu | Leu | Ser | Ser | His | Ile | Pro | Leu | Lys | Gly | Ile | Glu | Pro | Gly | |
| | | 690 | | | | | 695 | | | | | 700 | | | | |
| TCC | CTG | CGT | GTT | CGA | GCA | CGA | TAC | TCT | ATG | GAA | AAA | ATC | ATG | CCA | GAA | 2278 |
| Ser | Leu | Arg | Val | Arg | Ala | Arg | Tyr | Ser | Met | Glu | Lys | Ile | Met | Pro | Glu | |
| 705 | | | | 710 | | | | | 715 | | | | | 720 | | |
| GAA | GAG | TAC | AGT | GAA | TTT | AAA | GAG | CTT | ATA | CTG | CAA | AAG | GAA | CTT | CAT | 2326 |
| Glu | Glu | Tyr | Ser | Glu | Phe | Lys | Glu | Leu | Ile | Leu | Gln | Lys | Glu | Leu | His | |
| | | | | 725 | | | | | 730 | | | | | 735 | | |
| GTA | GTC | TAT | GCT | TTA | TCA | CAT | GTA | TGT | GGA | CAA | GAC | CGA | ACA | CTA | CTG | 2374 |
| Val | Val | Tyr | Ala | Leu | Ser | His | Val | Cys | Gly | Gln | Asp | Arg | Thr | Leu | Leu | |
| | | | 740 | | | | | 745 | | | | | 750 | | | |
| GCC | AGC | ATC | CTA | CTG | AGG | ATT | TTT | CTT | CAC | GAA | AAG | CTT | GAA | TCG | TTG | 2422 |
| Ala | Ser | Ile | Leu | Leu | Arg | Ile | Phe | Leu | His | Glu | Lys | Leu | Glu | Ser | Leu | |
| | | 755 | | | | | 760 | | | | | 765 | | | | |
| TTG | TTA | TGC | ACA | CTA | AAT | GAC | AGA | GAA | ATA | AGC | ATG | GAA | GAT | GAA | GCC | 2470 |
| Leu | Leu | Cys | Thr | Leu | Asn | Asp | Arg | Glu | Ile | Ser | Met | Glu | Asp | Glu | Ala | |
| | 770 | | | | | 775 | | | | | 780 | | | | | |
| ACT | ACC | CTA | TTT | CGA | GCC | ACA | ACA | CTT | GCA | AGC | ACC | TTG | ATG | GAG | CAG | 2518 |
| Thr | Thr | Leu | Phe | Arg | Ala | Thr | Thr | Leu | Ala | Ser | Thr | Leu | Met | Glu | Gln | |
| 785 | | | | 790 | | | | | 795 | | | | | 800 | | |
| TAT | ATG | AAA | GCC | ACT | GCT | ACA | CAG | TTT | GTT | CAT | CAT | GCT | TTG | AAA | GAC | 2566 |
| Tyr | Met | Lys | Ala | Thr | Ala | Thr | Gln | Phe | Val | His | His | Ala | Leu | Lys | Asp | |
| | | | | 805 | | | | | 810 | | | | | 815 | | |
| TCT | ATT | TTA | AAG | ATA | ATG | GAA | AGC | AAG | CAG | TCT | TGT | GAG | TTA | AGT | CCA | 2614 |
| Ser | Ile | Leu | Lys | Ile | Met | Glu | Ser | Lys | Gln | Ser | Cys | Glu | Leu | Ser | Pro | |
| | | | 820 | | | | | 825 | | | | | 830 | | | |
| TCA | AAG | TTA | GAA | AAA | AAT | GAA | GAT | GTG | AAC | ACT | AAT | TTA | ACA | CAC | CTA | 2662 |
| Ser | Lys | Leu | Glu | Lys | Asn | Glu | Asp | Val | Asn | Thr | Asn | Leu | Thr | His | Leu | |
| | | 835 | | | | | 840 | | | | | 845 | | | | |
| TTG | AAC | ATA | CTT | TCA | GAG | CTT | GTG | GAG | AAA | ATA | TTC | ATG | GCT | TCA | GAA | 2710 |
| Leu | Asn | Ile | Leu | Ser | Glu | Leu | Val | Glu | Lys | Ile | Phe | Met | Ala | Ser | Glu | |
| | 850 | | | | | 855 | | | | | 860 | | | | | |
| ATA | CTT | CCA | CCG | ACA | TTG | AGA | TAT | ATT | TAT | GGG | TGT | TTA | CAG | AAA | TCT | 2758 |
| Ile | Leu | Pro | Pro | Thr | Leu | Arg | Tyr | Ile | Tyr | Gly | Cys | Leu | Gln | Lys | Ser | |
| 865 | | | | 870 | | | | | 875 | | | | | 880 | | |

| | | | | | | | | | | | | | | | | |
|---|---|---|---|---|---|---|---|---|---|---|---|---|---|---|---|---|
| GTT | CAG | CAT | AAG | TGG | CCT | ACA | AAT | ACC | ACC | ATG | AGA | ACA | AGA | GTT | GTT | 2806 |
| Val | Gln | His | Lys | Trp | Pro | Thr | Asn | Thr | Thr | Met | Arg | Thr | Arg | Val | Val | |
| | | | | 885 | | | | 890 | | | | | | 895 | | |
| AGT | GGT | TTT | GTT | TTT | CTT | CGA | CTC | ATC | TGT | CCT | GCC | ATC | CTG | AAT | CCA | 2854 |
| Ser | Gly | Phe | Val | Phe | Leu | Arg | Leu | Ile | Cys | Pro | Ala | Ile | Leu | Asn | Pro | |
| | | | 900 | | | | | 905 | | | | | 910 | | | |
| CGG | ATG | TTC | AAT | ATC | ATC | TCA | GAT | TCT | CCA | TCT | CCT | ATT | GCT | GCA | AGA | 2902 |
| Arg | Met | Phe | Asn | Ile | Ile | Ser | Asp | Ser | Pro | Ser | Pro | Ile | Ala | Ala | Arg | |
| | | | 915 | | | | 920 | | | | | 925 | | | | |
| ACA | CTG | ATA | TTA | GTG | GCT | AAA | TCT | GTG | CAG | AAC | TTA | GCA | AAT | CTT | GTG | 2950 |
| Thr | Leu | Ile | Leu | Val | Ala | Lys | Ser | Val | Gln | Asn | Leu | Ala | Asn | Leu | Val | |
| | | 930 | | | | 935 | | | | | 940 | | | | | |
| GAA | TTT | GGA | GCT | AAG | GAG | CCC | TAC | ATG | GAA | GGT | GTC | AAT | CCA | TTC | ATC | 2998 |
| Glu | Phe | Gly | Ala | Lys | Glu | Pro | Tyr | Met | Glu | Gly | Val | Asn | Pro | Phe | Ile | |
| 945 | | | | | 950 | | | | | 955 | | | | | 960 | |
| AAA | AGC | AAC | AAA | CAT | CGT | ATG | ATC | ATG | TTT | TTA | GAT | GAA | CTT | GGG | AAT | 3046 |
| Lys | Ser | Asn | Lys | His | Arg | Met | Ile | Met | Phe | Leu | Asp | Glu | Leu | Gly | Asn | |
| | | | | 965 | | | | | 970 | | | | | 975 | | |
| GTA | CCT | GAA | CTT | CCG | GAC | ACT | ACA | GAG | CAT | TCT | AGA | ACG | GAC | CTG | TCC | 3094 |
| Val | Pro | Glu | Leu | Pro | Asp | Thr | Thr | Glu | His | Ser | Arg | Thr | Asp | Leu | Ser | |
| | | | 980 | | | | | 985 | | | | | 990 | | | |
| CGT | GAT | TTA | GCA | GCA | TTG | CAT | GAG | ATT | TGC | GTG | GCT | CAT | TCA | GAT | GAA | 3142 |
| Arg | Asp | Leu | Ala | Ala | Leu | His | Glu | Ile | Cys | Val | Ala | His | Ser | Asp | Glu | |
| | | | 995 | | | | | 1000 | | | | | 1005 | | | |
| CTT | CGA | ACG | CTC | AGT | AAT | GAG | CGT | GGT | GCA | CAG | CAG | CAC | GTA | TTG | AAA | 3190 |
| Leu | Arg | Thr | Leu | Ser | Asn | Glu | Arg | Gly | Ala | Gln | Gln | His | Val | Leu | Lys | |
| | | 1010 | | | | | 1015 | | | | | 1020 | | | | |
| AAG | CTT | CTG | GCT | ATA | ACA | GAA | CTG | CTT | CAA | CAA | AAA | CAA | AAC | CAG | TAT | 3238 |
| Lys | Leu | Leu | Ala | Ile | Thr | Glu | Leu | Leu | Gln | Gln | Lys | Gln | Asn | Gln | Tyr | |
| 1025 | | | | | 1030 | | | | | 1035 | | | | | 1040 | |
| ACA | AAA | ACC | AAT | GAT | GTC | AGG | TAGCAGCCTT | CGCCCCAGTG | TTCTGCATGG | | | | | | | 3289 |
| Thr | Lys | Thr | Asn | Asp | Val | Arg | | | | | | | | | | |
| | | | | 1045 | | | | | | | | | | | | |

```
ATTCAGCATG  TCCAACATGG  TAATTCACTT  CAGTTTAATG  TCTCCTTTGC  TCTTGCCAAA   3349
AAATAGCACA  CTTTTCCACA  TTCCAGTGAT  GTGTGAGCTA  TGCAAACAAA  ATCCAAGATT   3409
CTGCTGGTGA  ATAACTATGC  CAGCAACCTT  GTAAGCTATC  TGTGCAGGAT  ATTTGCACTA   3469
TTTCCACATG  GAATCAATCT  TTAACAACCT  CTGAGCCTTG  GTGTACAGAC  CACCTTTCAC   3529
AAAACGAAAT  GCTATGACTG  TATCTTGATA  TCTCGAACTT  TCAAAATATA  TTTTCAGTAC   3589
ACCCAGTTGC  CAAAGTTTTG  CTGTCTCTTA  GAGAAAGAAC  TATGAAATCA  ACTGACAAGA   3649
AACACATTCT  TATTGACAAT  TGTGTATAAC  TGGATTGCAG  ACTGTTCTTA  CTGTAACTAC   3709
TTCCTGATTA  GGAATATGAC  CATTTGACTG  TTCAATGATT  ATTTGTATTT  ACAGTTTCCA   3769
GAGTTTGTCA  TTATAATAGG  AACAATCTTT  GCTGTATACT  TTAAAAAAT   ACTCTGCTAT   3829
TTCTCTTGCT  GGAACTGTTG  AAAGAAAATA  TATAGAATGA  TCTATTGCTC  ATCAGCTTTA   3889
TTTTTAAAC   ATACGACTTA  TTTTGTTGAA  ATTGTCAAAG  ACTGTATTTA  GATCTCATAA   3949
TGCTTTGTTA  AATGTTTACA  AGTAAATAGT  TTGAATTCAG  TAAATATTAT  TGGTTGTTGT   4009
ATTGATCAAT  GCATGTTACC  CATTCAACCA  TTTTATAGAC  TACCAATTTC  TTTTATGTTA   4069
ACTAGAATGC  TTTTGTTAAA  AGTTATTTGT  TCATTATTTG  TGCTACCCCT  TTGATTATGC   4129
AGACAACCTC  ATCAGCTGCC  TAACTTATCC  ATCTTTGAAC  TTCTGACTAC  TTGTTGTATC   4189
TGCTGGATAT  TTAGTTCAAC  TGTATAGTTT  TATTTACTTC  TGTATGTGTA  TTTTGTGAA    4249
GTATTCACAA  AGGTTAAGTT  AAAATAAAAC  CAAGGGATAT  CTTGCAAAAA  AAAAAAA      4307
```

( 2 ) INFORMATION FOR SEQ ID NO:8:

( i ) SEQUENCE CHARACTERISTICS:
        ( A ) LENGTH: 1047 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Met Ala Ala Glu Ala Gly Ser Glu Glu Gly Gly Pro Val Thr Ala
 1               5                  10                  15
Gly Ala Gly Gly Gly Gly Ala Ala Ala Gly Ser Ser Ala Tyr Pro Ala
                20                  25                  30
Val Cys Arg Val Lys Ile Pro Ala Ala Leu Pro Val Ala Ala Ala Pro
            35                  40                  45
Tyr Pro Gly Leu Val Glu Thr Gly Val Ala Gly Thr Leu Gly Gly Gly
        50                  55                  60
Ala Ala Leu Gly Ser Glu Phe Leu Gly Ala Gly Ser Val Ala Gly Ala
65                  70                  75                  80
Leu Gly Gly Ala Gly Leu Thr Gly Gly Gly Thr Ala Ala Gly Val Ala
                85                  90                  95
Gly Ala Ala Ala Gly Val Ala Gly Ala Ala Val Ala Gly Pro Ser Gly
                100                 105                 110
Asp Met Ala Leu Thr Lys Leu Pro Thr Ser Leu Leu Ala Glu Thr Leu
            115                 120                 125
Gly Pro Gly Gly Gly Phe Pro Pro Leu Pro Pro Pro Pro Tyr Leu Pro
        130                 135                 140
Pro Leu Gly Ala Gly Leu Gly Thr Val Asp Glu Gly Asp Ser Leu Asp
145                 150                 155                 160
Gly Pro Glu Tyr Glu Glu Glu Glu Val Ala Ile Pro Leu Thr Ala Pro
                165                 170                 175
Pro Thr Asn Gln Trp Tyr His Gly Lys Leu Asp Arg Thr Ile Ala Glu
            180                 185                 190
Glu Arg Leu Arg Gln Ala Gly Lys Ser Gly Ser Tyr Leu Ile Arg Glu
        195                 200                 205
Ser Asp Arg Arg Pro Gly Ser Phe Val Leu Ser Phe Leu Ser Gln Met
210                 215                 220
Asn Val Val Asn His Phe Arg Ile Ile Ala Met Cys Gly Asp Tyr Tyr
225                 230                 235                 240
Ile Gly Gly Arg Arg Phe Ser Ser Leu Ser Asp Leu Ile Gly Tyr Tyr
                245                 250                 255
Ser His Val Ser Cys Leu Leu Lys Gly Glu Lys Leu Leu Tyr Pro Val
            260                 265                 270
Ala Pro Pro Glu Pro Val Glu Asp Arg Arg Arg Val Arg Ala Ile Leu
        275                 280                 285
Pro Tyr Thr Lys Val Pro Asp Thr Asp Glu Ile Ser Phe Leu Lys Gly
        290                 295                 300
Asp Met Phe Ile Val His Asn Glu Leu Glu Asp Gly Trp Met Trp Val
305                 310                 315                 320
Thr Asn Leu Arg Thr Asp Glu Gln Gly Leu Ile Val Glu Asp Leu Val
                325                 330                 335
Glu Glu Val Gly Arg Glu Glu Asp Pro His Glu Gly Lys Ile Trp Phe
                340                 345                 350
His Gly Lys Ile Ser Lys Gln Glu Ala Tyr Asn Leu Leu Met Thr Val
            355                 360                 365
```

```
Gly  Gln  Val  Cys  Ser  Phe  Leu  Val  Arg  Pro  Ser  Asp  Asn  Thr  Pro  Gly
     370            375                      380

Asp  Tyr  Ser  Leu  Tyr  Phe  Arg  Thr  Asn  Glu  Asn  Ile  Gln  Arg  Phe  Lys
385                      390                      395                      400

Ile  Cys  Pro  Thr  Pro  Asn  Asn  Gln  Phe  Met  Met  Gly  Gly  Arg  Tyr  Tyr
                    405                      410                      415

Asn  Ser  Ile  Gly  Asp  Ile  Ile  Asp  His  Tyr  Arg  Lys  Glu  Gln  Ile  Val
               420                      425                      430

Glu  Gly  Tyr  Tyr  Leu  Lys  Glu  Pro  Val  Pro  Met  Gln  Asp  Gln  Glu  Gln
          435                      440                      445

Val  Leu  Asn  Asp  Thr  Val  Asp  Gly  Lys  Glu  Ile  Tyr  Asn  Thr  Ile  Arg
     450                      455                      460

Arg  Lys  Thr  Lys  Asp  Ala  Phe  Tyr  Lys  Asn  Ile  Val  Lys  Lys  Gly  Tyr
465                      470                      475                      480

Leu  Leu  Lys  Lys  Gly  Lys  Gly  Lys  Arg  Trp  Lys  Asn  Leu  Tyr  Phe  Ile
                    485                      490                      495

Leu  Glu  Gly  Ser  Asp  Ala  Gln  Leu  Ile  Tyr  Phe  Glu  Ser  Glu  Lys  Arg
               500                      505                      510

Ala  Thr  Lys  Pro  Lys  Gly  Leu  Ile  Asp  Leu  Ser  Val  Cys  Ser  Val  Tyr
          515                      520                      525

Val  Val  His  Asp  Ser  Leu  Phe  Gly  Arg  Pro  Asn  Cys  Phe  Gln  Ile  Val
     530                      535                      540

Val  Gln  His  Phe  Ser  Glu  Glu  His  Tyr  Ile  Phe  Tyr  Phe  Ala  Gly  Glu
545                      550                      555                      560

Thr  Pro  Glu  Gln  Ala  Glu  Asp  Trp  Met  Lys  Gly  Leu  Gln  Ala  Phe  Cys
                    565                      570                      575

Asn  Leu  Arg  Lys  Ser  Ser  Pro  Gly  Thr  Ser  Asn  Lys  Arg  Leu  Arg  Gln
               580                      585                      590

Val  Ser  Ser  Leu  Val  Leu  His  Ile  Glu  Glu  Ala  His  Lys  Leu  Pro  Val
     595                      600                      605

Lys  His  Phe  Thr  Asn  Pro  Tyr  Cys  Asn  Ile  Tyr  Leu  Asn  Ser  Val  Gln
     610                      615                      620

Val  Ala  Lys  Thr  His  Ala  Arg  Glu  Gly  Gln  Asn  Pro  Val  Trp  Ser  Glu
625                      630                      635                      640

Glu  Phe  Val  Phe  Asp  Asp  Leu  Pro  Pro  Asp  Ile  Asn  Arg  Phe  Glu  Ile
                    645                      650                      655

Thr  Leu  Ser  Asn  Lys  Thr  Lys  Lys  Ser  Lys  Asp  Pro  Asp  Ile  Leu  Phe
               660                      665                      670

Met  Arg  Cys  Gln  Leu  Ser  Arg  Leu  Gln  Lys  Gly  His  Ala  Thr  Asp  Glu
          675                      680                      685

Trp  Phe  Leu  Leu  Ser  Ser  His  Ile  Pro  Leu  Lys  Gly  Ile  Glu  Pro  Gly
     690                      695                      700

Ser  Leu  Arg  Val  Arg  Ala  Arg  Tyr  Ser  Met  Glu  Lys  Ile  Met  Pro  Glu
705                      710                      715                      720

Glu  Glu  Tyr  Ser  Glu  Phe  Lys  Glu  Leu  Ile  Leu  Gln  Lys  Glu  Leu  His
                    725                      730                      735

Val  Val  Tyr  Ala  Leu  Ser  His  Val  Cys  Gly  Gln  Asp  Arg  Thr  Leu  Leu
               740                      745                      750

Ala  Ser  Ile  Leu  Leu  Arg  Ile  Phe  Leu  His  Glu  Lys  Leu  Glu  Ser  Leu
          755                      760                      765

Leu  Leu  Cys  Thr  Leu  Asn  Asp  Arg  Glu  Ile  Ser  Met  Glu  Asp  Glu  Ala
     770                      775                      780

Thr  Thr  Leu  Phe  Arg  Ala  Thr  Thr  Leu  Ala  Ser  Thr  Leu  Met  Glu  Gln
785                      790                      795                      800
```

| | | | | | | | | | | | | | | |
|---|---|---|---|---|---|---|---|---|---|---|---|---|---|---|
|Tyr|Met|Lys|Ala|Thr|Ala|Thr|Gln|Phe|Val|His|His|Ala|Leu|Lys|Asp|
| | | |805| | | | |810| | | | |815| |
|Ser|Ile|Leu|Lys|Ile|Met|Glu|Ser|Lys|Gln|Ser|Cys|Glu|Leu|Ser|Pro|
| | | |820| | | |825| | | | |830| | |
|Ser|Lys|Leu|Glu|Lys|Asn|Glu|Asp|Val|Asn|Thr|Asn|Leu|Thr|His|Leu|
| | |835| | | |840| | | | |845| | | |
|Leu|Asn|Ile|Leu|Ser|Glu|Leu|Val|Glu|Lys|Ile|Phe|Met|Ala|Ser|Glu|
| |850| | | |855| | | | |860| | | | |
|Ile|Leu|Pro|Pro|Thr|Leu|Arg|Tyr|Ile|Tyr|Gly|Cys|Leu|Gln|Lys|Ser|
|865| | | |870| | | | |875| | | | |880| |
|Val|Gln|His|Lys|Trp|Pro|Thr|Asn|Thr|Thr|Met|Arg|Thr|Arg|Val|Val|
| | | |885| | | | |890| | | | |895| | |
|Ser|Gly|Phe|Val|Phe|Leu|Arg|Leu|Ile|Cys|Pro|Ala|Ile|Leu|Asn|Pro|
| | |900| | | | |905| | | | |910| | | |
|Arg|Met|Phe|Asn|Ile|Ile|Ser|Asp|Ser|Pro|Ser|Pro|Ile|Ala|Ala|Arg|
| | |915| | | | |920| | | | |925| | | |
|Thr|Leu|Ile|Leu|Val|Ala|Lys|Ser|Val|Gln|Asn|Leu|Ala|Asn|Leu|Val|
| |930| | | | |935| | | | |940| | | | |
|Glu|Phe|Gly|Ala|Lys|Glu|Pro|Tyr|Met|Glu|Gly|Val|Asn|Pro|Phe|Ile|
|945| | | |950| | | | |955| | | | | |960|
|Lys|Ser|Asn|Lys|His|Arg|Met|Ile|Met|Phe|Leu|Asp|Glu|Leu|Gly|Asn|
| | | |965| | | |970| | | | |975| | | |
|Val|Pro|Glu|Leu|Pro|Asp|Thr|Thr|Glu|His|Ser|Arg|Thr|Asp|Leu|Ser|
| | |980| | | | |985| | | | |990| | | |
|Arg|Asp|Leu|Ala|Ala|Leu|His|Glu|Ile|Cys|Val|Ala|His|Ser|Asp|Glu|
| |995| | | | |1000| | | | |1005| | | | |
|Leu|Arg|Thr|Leu|Ser|Asn|Glu|Arg|Gly|Ala|Gln|Gln|His|Val|Leu|Lys|
| |1010| | | | |1015| | | | |1020| | | | |
|Lys|Leu|Leu|Ala|Ile|Thr|Glu|Leu|Leu|Gln|Gln|Lys|Gln|Asn|Gln|Tyr|
|1025| | | |1030| | | | |1035| | | | | |1040|
|Thr|Lys|Thr|Asn|Asp|Val|Arg| | | | | | | | | |
| | | |1045| | | | | | | | | | | | |

( 2 ) INFORMATION FOR SEQ ID NO:9:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
GTAAGTTAAG ACTGCTGTTC AGGAATTTGG GAAGCTGGCT CCAGAAAAGA AGTGGAAATG    60

AAGGG                                                                65
```

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | |
|---|---|---|---|---|---|---|---|---|---|---|---|---|
|Asp|Cys|Cys|Ser|Gly|Ile|Trp|Glu|Ala|Gly|Ser|Arg|Lys|
|1| | | |5| | | | |10| | | |

```
Glu Val Glu Met Lys
    15
```

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

```
CCGAGATCCG CGGATCCT                                                                 18
```

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
CCGAGATCC                                                                            9
```

( 2 ) INFORMATION FOR SEQ ID NO:13:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

```
GATCCACCAT GGAGCTCGAG ATCTAGAATT CTGCAGCCCG GGTACCGATC                              50
```

( 2 ) INFORMATION FOR SEQ ID NO:14:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
GATCGGTACC CGGGCTGCAG AATTCTAGAT CTCGAGCTCC ATGGTGGATC                              50
```

( 2 ) INFORMATION FOR SEQ ID NO:15:

( i ) SEQUENCE CHARACTERISTICS:
        ( A ) LENGTH: 351 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

```
AAAACTCATG CAAGGGAAGG GCAAAACCCA GTATGGTCAG AAGAGTTTGT CTTTGATGAT                   60
CTTCCTCCTG ACATCAATAG ATTTGAAATA ACTCTTAGTA ATAAAACAAA GAAAAGCAAA                  120
```

| | | | | | |
|---|---|---|---|---|---|
| GATCCTGATA | TCTTATTTAT | GCGCTGCCAG | TTGAGCCGAT | TACAGAAAGG | GCATGCCACA | 180
| GATGAATGGT | TTCTGCTCAG | CTCCCATATA | CCATTAAAAG | GTATTGAACC | AGGGTCCCTG | 240
| CGTGTTCGAG | CACGATACTC | TATGGAAAAA | ATCATGCCAG | AAGAAGAGTA | CAGTGAATTT | 300
| AAAGAGCTTA | TACTGCAAAA | GGAACTTCAT | GTAGTCTATG | CTTTATCACA | T | 351

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

TTTAAATTCA CTGTACTCTT CTTCTGGCAT GAT        33

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GAGGAAGATC ATCAAAGACA AACTCT        26

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TCTGTAATCG GCTCAACTGG CAGCG        25

( 2 ) INFORMATION FOR SEQ ID NO:19:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

CGTAAATTGC AAAATGCCTG CAGACCTTG        29

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GTTTCCTTT GCCCTTTTTC AGAAGATAAC                                              30

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

TGTCATTGAG TACTTGTTCT TGATCCTGC                                              29

( 2 ) INFORMATION FOR SEQ ID NO:22:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

GATCCACCAT GGAGCTCGAG ATCTAGAATT CTGCAGCCCG GGTACCGATC                       50

( 2 ) INFORMATION FOR SEQ ID NO:23:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

GATCGGTACC CGGGCTGCAG AATTCTAGAT CTCGAGCTCC ATGGTGGATC                       50

( 2 ) INFORMATION FOR SEQ ID NO:24:

( i ) SEQUENCE CHARACTERISTICS:
        ( A ) LENGTH: 3456 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 100..2709

( x i ) SEQUENCE DESCRIPTION: SEQ ID NO:24:

```
GGAAGAGGTG GCCATACCGT TGACCGCTCC TCCAACTAAC CAGTAAGTTA AGACTGCTGT         60

TCAGGAATTT GGGAAGCTGG CTCCAGAAAA GAAGTGGAA ATG AAG GGG TGG TAT          114
                                             Met Lys Gly Trp Tyr
                                               1               5

CAC GGA AAA CTT GAC AGA ACG ATA GCA GAA GAA CGC CTC AGG CAG GCA         162
His Gly Lys Leu Asp Arg Thr Ile Ala Glu Glu Arg Leu Arg Gln Ala
             10                  15                  20

GGG AAG TCT GGC AGT TAT CTT ATA AGA GAG AGT GAT CGG AGG CCA GGG         210
Gly Lys Ser Gly Ser Tyr Leu Ile Arg Glu Ser Asp Arg Arg Pro Gly
         25                  30                  35
```

| | | | | | | | | | | | | | | | | |
|---|---|---|---|---|---|---|---|---|---|---|---|---|---|---|---|---|
| TCC | TTT | GTA | CTT | TCA | TTT | CTT | AGC | CAG | ATG | AAT | GTT | GTC | AAC | CAT | TTT | 258 |
| Ser | Phe | Val | Leu | Ser | Phe | Leu | Ser | Gln | Met | Asn | Val | Val | Asn | His | Phe | |
| | | 40 | | | | | 45 | | | | | 50 | | | | |
| AGG | ATT | ATT | GCT | ATG | TGT | GGA | GAT | TAC | TAC | ATT | GGT | GGA | AGA | CGT | TTT | 306 |
| Arg | Ile | Ile | Ala | Met | Cys | Gly | Asp | Tyr | Tyr | Ile | Gly | Gly | Arg | Arg | Phe | |
| | 55 | | | | | 60 | | | | | 65 | | | | | |
| TCT | TCA | CTG | TCA | GAC | CTA | ATA | GGT | TAT | TAC | AGT | CAT | GTT | TCT | TGT | TTG | 354 |
| Ser | Ser | Leu | Ser | Asp | Leu | Ile | Gly | Tyr | Tyr | Ser | His | Val | Ser | Cys | Leu | |
| 70 | | | | | 75 | | | | | 80 | | | | | 85 | |
| CTT | AAA | GGA | GAA | AAA | TTA | CTT | TAC | CCA | GTT | GCA | CCA | CCA | GAG | CCA | GTA | 402 |
| Leu | Lys | Gly | Glu | Lys | Leu | Leu | Tyr | Pro | Val | Ala | Pro | Pro | Glu | Pro | Val | |
| | | | | 90 | | | | | 95 | | | | | 100 | | |
| GAA | GAT | AGA | AGG | CGT | GTA | CGA | GCT | ATT | CTA | CCT | TAC | ACA | AAA | GTA | CCA | 450 |
| Glu | Asp | Arg | Arg | Arg | Val | Arg | Ala | Ile | Leu | Pro | Tyr | Thr | Lys | Val | Pro | |
| | | | 105 | | | | | 110 | | | | | 115 | | | |
| GAC | ACT | GAT | GAA | ATA | AGT | TTC | TTA | AAA | GGA | GAT | ATG | TTC | ATT | GTT | CAT | 498 |
| Asp | Thr | Asp | Glu | Ile | Ser | Phe | Leu | Lys | Gly | Asp | Met | Phe | Ile | Val | His | |
| | | | 120 | | | | | 125 | | | | | 130 | | | |
| AAT | GAA | TTA | GAA | GAT | GGA | TGG | ATG | TGG | GTT | ACA | AAT | TTA | AGA | ACA | GAT | 546 |
| Asn | Glu | Leu | Glu | Asp | Gly | Trp | Met | Trp | Val | Thr | Asn | Leu | Arg | Thr | Asp | |
| 135 | | | | | 140 | | | | | 145 | | | | | | |
| GAA | CAA | GGC | CTT | ATT | GTT | GAA | GAC | CTA | GTA | GAA | GAG | GTG | GGC | CGG | GAA | 594 |
| Glu | Gln | Gly | Leu | Ile | Val | Glu | Asp | Leu | Val | Glu | Glu | Val | Gly | Arg | Glu | |
| 150 | | | | | 155 | | | | | 160 | | | | | 165 | |
| GAA | GAT | CCA | CAT | GAA | GGA | AAA | ATA | TGG | TTC | CAT | GGG | AAG | ATT | TCC | AAA | 642 |
| Glu | Asp | Pro | His | Glu | Gly | Lys | Ile | Trp | Phe | His | Gly | Lys | Ile | Ser | Lys | |
| | | | | 170 | | | | | 175 | | | | | 180 | | |
| CAG | GAA | GCT | TAT | AAT | TTA | CTA | ATG | ACA | GTT | GGT | CAA | GTC | TGC | AGT | TTT | 690 |
| Gln | Glu | Ala | Tyr | Asn | Leu | Leu | Met | Thr | Val | Gly | Gln | Val | Cys | Ser | Phe | |
| | | | 185 | | | | | 190 | | | | | 195 | | | |
| CTT | GTG | AGG | CCC | TCA | GAT | AAT | ACT | CCT | GGC | GAT | TAT | TCA | CTT | TAT | TTC | 738 |
| Leu | Val | Arg | Pro | Ser | Asp | Asn | Thr | Pro | Gly | Asp | Tyr | Ser | Leu | Tyr | Phe | |
| | | 200 | | | | | 205 | | | | | 210 | | | | |
| CGG | ACC | AAT | GAA | AAT | ATT | CAG | CGA | TTT | AAA | ATA | TGT | CCA | ACG | CCA | AAC | 786 |
| Arg | Thr | Asn | Glu | Asn | Ile | Gln | Arg | Phe | Lys | Ile | Cys | Pro | Thr | Pro | Asn | |
| | 215 | | | | | 220 | | | | | 225 | | | | | |
| AAT | CAG | TTT | ATG | ATG | GGA | GGC | CGG | TAT | TAT | AAC | AGC | ATT | GGG | GAC | ATC | 834 |
| Asn | Gln | Phe | Met | Met | Gly | Gly | Arg | Tyr | Tyr | Asn | Ser | Ile | Gly | Asp | Ile | |
| 230 | | | | | 235 | | | | | 240 | | | | | 245 | |
| ATA | GAT | CAC | TAT | CGA | AAA | GAA | CAG | ATT | GTT | GAA | GGA | TAT | TAT | CTT | AAG | 882 |
| Ile | Asp | His | Tyr | Arg | Lys | Glu | Gln | Ile | Val | Glu | Gly | Tyr | Tyr | Leu | Lys | |
| | | | | 250 | | | | | 255 | | | | | 260 | | |
| GAA | CCT | GTA | CCA | ATG | CAG | GAT | CAA | GAA | CAA | GTA | CTC | AAT | GAC | ACA | GTG | 930 |
| Glu | Pro | Val | Pro | Met | Gln | Asp | Gln | Glu | Gln | Val | Leu | Asn | Asp | Thr | Val | |
| | | | 265 | | | | | 270 | | | | | 275 | | | |
| GAT | GGC | AAG | GAA | ATC | TAT | AAT | ACC | ATC | CGT | CGT | AAA | ACA | AAG | GAT | GCC | 978 |
| Asp | Gly | Lys | Glu | Ile | Tyr | Asn | Thr | Ile | Arg | Arg | Lys | Thr | Lys | Asp | Ala | |
| | | 280 | | | | | 285 | | | | | 290 | | | | |
| TTT | TAT | AAA | AAC | ATT | GTT | AAG | AAA | GGT | TAT | CTT | CTG | AAA | AAG | GGC | AAA | 1026 |
| Phe | Tyr | Lys | Asn | Ile | Val | Lys | Lys | Gly | Tyr | Leu | Leu | Lys | Lys | Gly | Lys | |
| 295 | | | | | 300 | | | | | 305 | | | | | | |
| GGA | AAA | CGT | TGG | AAA | AAT | TTA | TAT | TTT | ATC | TTA | GAG | GGT | AGT | GAT | GCC | 1074 |
| Gly | Lys | Arg | Trp | Lys | Asn | Leu | Tyr | Phe | Ile | Leu | Glu | Gly | Ser | Asp | Ala | |
| 310 | | | | | 315 | | | | | 320 | | | | | 325 | |
| CAA | CTT | ATT | TAT | TTT | GAA | AGC | GAA | AAA | CGA | GCT | ACC | AAA | CCA | AAA | GGA | 1122 |
| Gln | Leu | Ile | Tyr | Phe | Glu | Ser | Glu | Lys | Arg | Ala | Thr | Lys | Pro | Lys | Gly | |
| | | | | 330 | | | | | 335 | | | | | 340 | | |
| TTA | ATA | GAT | CTC | AGT | GTA | TGT | TCT | GTC | TAT | GTC | GTT | CAT | GAT | AGT | CTC | 1170 |
| Leu | Ile | Asp | Leu | Ser | Val | Cys | Ser | Val | Tyr | Val | Val | His | Asp | Ser | Leu | |
| | | | 345 | | | | | 350 | | | | | 355 | | | |

| | | | | | | | | | | | | | | | | |
|---|---|---|---|---|---|---|---|---|---|---|---|---|---|---|---|---|
| TTT | GGC | AGG | CCA | AAC | TGT | TTT | CAG | ATA | GTA | GTT | CAG | CAC | TTT | AGT | GAA | 1218 |
| Phe | Gly | Arg<br>360 | Pro | Asn | Cys | Phe | Gln<br>365 | Ile | Val | Val | Gln | His<br>370 | Phe | Ser | Glu | |
| GAA | CAT | TAC | ATC | TTT | TAC | TTT | GCA | GGA | GAA | ACT | CCA | GAA | CAA | GCA | GAG | 1266 |
| Glu | His<br>375 | Tyr | Ile | Phe | Tyr | Phe<br>380 | Ala | Gly | Glu | Thr | Pro<br>385 | Glu | Gln | Ala | Glu | |
| GAT | TGG | ATG | AAA | GGT | CTG | CAG | GCA | TTT | TGC | AAT | TTA | CGG | AAA | AGT | AGT | 1314 |
| Asp<br>390 | Trp | Met | Lys | Gly | Leu<br>395 | Gln | Ala | Phe | Cys | Asn<br>400 | Leu | Arg | Lys | Ser | Ser<br>405 | |
| CCA | GGG | ACA | TCC | AAT | AAA | CGC | CTT | CGT | CAG | GTC | AGC | AGC | CTT | GTT | TTA | 1362 |
| Pro | Gly | Thr | Ser | Asn<br>410 | Lys | Arg | Leu | Arg | Gln<br>415 | Val | Ser | Ser | Leu | Val<br>420 | Leu | |
| CAT | ATT | GAA | GAA | GCC | CAT | AAA | CTC | CCA | GTA | AAA | CAT | TTT | ACT | AAT | CCA | 1410 |
| His | Ile | Glu | Glu<br>425 | Ala | His | Lys | Leu | Pro<br>430 | Val | Lys | His | Phe | Thr<br>435 | Asn | Pro | |
| TAT | TGT | AAC | ATC | TAC | CTG | AAT | AGT | GTC | CAA | GTA | GCA | AAA | ACT | CAT | GCA | 1458 |
| Tyr | Cys | Asn<br>440 | Ile | Tyr | Leu | Asn | Ser<br>445 | Val | Gln | Val | Ala | Lys<br>450 | Thr | His | Ala | |
| AGG | GAA | GGG | CAA | AAC | CCA | GTA | TGG | TCA | GAA | GAG | TTT | GTC | TTT | GAT | GAT | 1506 |
| Arg | Glu<br>455 | Gly | Gln | Asn | Pro | Val<br>460 | Trp | Ser | Glu | Glu | Phe<br>465 | Val | Phe | Asp | Asp | |
| CTT | CCT | CCT | GAC | ATC | AAT | AGA | TTT | GAA | ATA | ACT | CTT | AGT | AAT | AAA | ACA | 1554 |
| Leu<br>470 | Pro | Pro | Asp | Ile | Asn<br>475 | Arg | Phe | Glu | Ile | Thr<br>480 | Leu | Ser | Asn | Lys | Thr<br>485 | |
| AAG | AAA | AGC | AAA | GAT | CCT | GAT | ATC | TTA | TTT | ATG | CGC | TGC | CAG | TTG | AGC | 1602 |
| Lys | Lys | Ser | Lys | Asp<br>490 | Pro | Asp | Ile | Leu | Phe<br>495 | Met | Arg | Cys | Gln | Leu<br>500 | Ser | |
| CGA | TTA | CAG | AAA | GGG | CAT | GCC | ACA | GAT | GAA | TGG | TTT | CTG | CTC | AGC | TCC | 1650 |
| Arg | Leu | Gln | Lys<br>505 | Gly | His | Ala | Thr | Asp<br>510 | Glu | Trp | Phe | Leu | Leu<br>515 | Ser | Ser | |
| CAT | ATA | CCA | TTA | AAA | GGT | ATT | GAA | CCA | GGG | TCC | CTG | CGT | GTT | CGA | GCA | 1698 |
| His | Ile | Pro<br>520 | Leu | Lys | Gly | Ile | Glu<br>525 | Pro | Gly | Ser | Leu | Arg<br>530 | Val | Arg | Ala | |
| CGA | TAC | TCT | ATG | GAA | AAA | ATC | ATG | CCA | GAA | GAA | GAG | TAC | AGT | GAA | TTT | 1746 |
| Arg | Tyr<br>535 | Ser | Met | Glu | Lys | Ile<br>540 | Met | Pro | Glu | Glu | Glu<br>545 | Tyr | Ser | Glu | Phe | |
| AAA | GAG | CTT | ATA | CTG | CAA | AAG | GAA | CTT | CAT | GTA | GTC | TAT | GCT | TTA | TCA | 1794 |
| Lys<br>550 | Glu | Leu | Ile | Leu | Gln<br>555 | Lys | Glu | Leu | His | Val<br>560 | Val | Tyr | Ala | Leu | Ser<br>565 | |
| CAT | GTA | TGT | GGA | CAA | GAC | CGA | ACA | CTA | CTG | GCC | AGC | ATC | CTA | CTG | AGG | 1842 |
| His | Val | Cys | Gly | Gln<br>570 | Asp | Arg | Thr | Leu | Leu<br>575 | Ala | Ser | Ile | Leu | Leu<br>580 | Arg | |
| ATT | TTT | CTT | CAC | GAA | AAG | CTT | GAA | TCG | TTG | TTG | TTA | TGC | ACA | CTA | AAT | 1890 |
| Ile | Phe | Leu | His<br>585 | Glu | Lys | Leu | Glu | Ser<br>590 | Leu | Leu | Leu | Cys | Thr<br>595 | Leu | Asn | |
| GAC | AGA | GAA | ATA | AGC | ATG | GAA | GAT | GAA | GCC | ACT | ACC | CTA | TTT | CGA | GCC | 1938 |
| Asp | Arg | Glu<br>600 | Ile | Ser | Met | Glu | Asp<br>605 | Glu | Ala | Thr | Thr | Leu<br>610 | Phe | Arg | Ala | |
| ACA | ACA | CTT | GCA | AGC | ACC | TTG | ATG | GAG | CAG | TAT | ATG | AAA | GCC | ACT | GCT | 1986 |
| Thr | Thr | Leu<br>615 | Ala | Ser | Thr | Leu | Met<br>620 | Glu | Gln | Tyr | Met | Lys<br>625 | Ala | Thr | Ala | |
| ACA | CAG | TTT | GTT | CAT | CAT | GCT | TTG | AAA | GAC | TCT | ATT | TTA | AAG | ATA | ATG | 2034 |
| Thr<br>630 | Gln | Phe | Val | His | His<br>635 | Ala | Leu | Lys | Asp | Ser<br>640 | Ile | Leu | Lys | Ile | Met<br>645 | |
| GAA | AGC | AAG | CAG | TCT | TGT | GAG | TTA | AGT | CCA | TCA | AAG | TTA | GAA | AAA | AAT | 2082 |
| Glu | Ser | Lys | Gln | Ser<br>650 | Cys | Glu | Leu | Ser | Pro<br>655 | Ser | Lys | Leu | Glu | Lys<br>660 | Asn | |
| GAA | GAT | GTG | AAC | ACT | AAT | TTA | ACA | CAC | CTA | TTG | AAC | ATA | CTT | TCA | GAG | 2130 |
| Glu | Asp | Val | Asn<br>665 | Thr | Asn | Leu | Thr | His<br>670 | Leu | Leu | Asn | Ile | Leu<br>675 | Ser | Glu | |

| | | | | | | | | | | | | | | | | |
|---|---|---|---|---|---|---|---|---|---|---|---|---|---|---|---|---|
| CTT | GTG | GAG | AAA | ATA | TTC | ATG | GCT | TCA | GAA | ATA | CTT | CCA | CCG | ACA | TTG | 2178 |
| Leu | Val | Glu 680 | Lys | Ile | Phe | Met | Ala 685 | Ser | Glu | Ile | Leu | Pro 690 | Pro | Thr | Leu | |
| AGA | TAT | ATT | TAT | GGG | TGT | TTA | CAG | AAA | TCT | GTT | CAG | CAT | AAG | TGG | CCT | 2226 |
| Arg | Tyr 695 | Ile | Tyr | Gly | Cys | Leu 700 | Gln | Lys | Ser | Val | Gln 705 | His | Lys | Trp | Pro | |
| ACA | AAT | ACC | ACC | ATG | AGA | ACA | AGA | GTT | GTT | AGT | GGT | TTT | GTT | TTT | CTT | 2274 |
| Thr 710 | Asn | Thr | Thr | Met | Arg 715 | Thr | Arg | Val | Val | Ser 720 | Gly | Phe | Val | Phe | Leu 725 | |
| CGA | CTC | ATC | TGT | CCT | GCC | ATC | CTG | AAT | CCA | CGG | ATG | TTC | AAT | ATC | ATC | 2322 |
| Arg | Leu | Ile | Cys | Pro 730 | Ala | Ile | Leu | Asn | Pro 735 | Arg | Met | Phe | Asn | Ile 740 | Ile | |
| TCA | GAT | TCT | CCA | TCT | CCT | ATT | GCT | GCA | AGA | ACA | CTG | ATA | TTA | GTG | GCT | 2370 |
| Ser | Asp | Ser | Pro 745 | Ser | Pro | Ile | Ala | Ala 750 | Arg | Thr | Leu | Ile | Leu 755 | Val | Ala | |
| AAA | TCT | GTG | CAG | AAC | TTA | GCA | AAT | CTT | GTG | GAA | TTT | GGA | GCT | AAG | GAG | 2418 |
| Lys | Ser | Val 760 | Gln | Asn | Leu | Ala | Asn 765 | Leu | Val | Glu | Phe | Gly 770 | Ala | Lys | Glu | |
| CCC | TAC | ATG | GAA | GGT | GTC | AAT | CCA | TTC | ATC | AAA | AGC | AAC | AAA | CAT | CGT | 2466 |
| Pro | Tyr 775 | Met | Glu | Gly | Val | Asn 780 | Pro | Phe | Ile | Lys | Ser 785 | Asn | Lys | His | Arg | |
| ATG | ATC | ATG | TTT | TTA | GAT | GAA | CTT | GGG | AAT | GTA | CCT | GAA | CTT | CCG | GAC | 2514 |
| Met 790 | Ile | Met | Phe | Leu | Asp 795 | Glu | Leu | Gly | Asn | Val 800 | Pro | Glu | Leu | Pro | Asp 805 | |
| ACT | ACA | GAG | CAT | TCT | AGA | ACG | GAC | CTG | TCC | CGT | GAT | TTA | GCA | GCA | TTG | 2562 |
| Thr | Thr | Glu | His | Ser 810 | Arg | Thr | Asp | Leu | Ser 815 | Arg | Asp | Leu | Ala | Ala 820 | Leu | |
| CAT | GAG | ATT | TGC | GTG | GCT | CAT | TCA | GAT | GAA | CTT | CGA | ACG | CTC | AGT | AAT | 2610 |
| His | Glu | Ile | Cys 825 | Val | Ala | His | Ser | Asp 830 | Glu | Leu | Arg | Thr | Leu 835 | Ser | Asn | |
| GAG | CGT | GGT | GCA | CAG | CAG | CAC | GTA | TTG | AAA | AAG | CTT | CTG | GCT | ATA | ACA | 2658 |
| Glu | Arg | Gly 840 | Ala | Gln | Gln | His | Val 845 | Leu | Lys | Lys | Leu | Leu 850 | Ala | Ile | Thr | |
| GAA | CTG | CTT | CAA | CAA | AAA | CAA | AAC | CAG | TAT | ACA | AAA | ACC | AAT | GAT | GTC | 2706 |
| Glu | Leu 855 | Leu | Gln | Gln | Lys | Gln 860 | Asn | Gln | Tyr | Thr | Lys 865 | Thr | Asn | Asp | Val | |
| AGG | TAG | CAGCCTTCGC | CCCAGTGTTC | TGCATGGATT | CAGCATGTCC | AACATGGTAA | | | | | | | | | | 2762 |
| Arg 870 | | | | | | | | | | | | | | | | |

| | | | | | |
|---|---|---|---|---|---|
| TTCACTTCAG | TTTAATGTCT | CCTTTGCTCT | TGCCAAAAAA | TAGCACACTT | TTCCACATTC | 2822 |
| CAGTGATGTG | TGAGCTATGC | AAACAAAATC | CAAGATTCTG | CTGGTGAATA | ACTATGCCAG | 2882 |
| CAACCTTGTA | AGCTATCTGT | GCAGGATATT | TGCACTATTT | CCACATGGAA | TCAATCTTTA | 2942 |
| ACAACCTCTG | AGCCTTGGTG | TACAGACCAC | CTTTCACAAA | ACGAAATGCT | ATGACTGTAT | 3002 |
| CTTGATATCT | CGAACTTTCA | AAATATATTT | TCAGTACACC | CAGTTGCCAA | AGTTTTGCTG | 3062 |
| TCTCTTAGAG | AAAGAACTAT | GAAATCAACT | GACAAGAAAC | ACATTCTTAT | TGACAATTGT | 3122 |
| GTATAACTGG | ATTGCAGACT | GTTCTTACTG | TAACTACTTC | CTGATTAGGA | ATATGACCAT | 3182 |
| TTGACTGTTC | AATGATTATT | TGTATTTACA | GTTCCAGAG | TTTGTCATTA | TAATAGGAAC | 3242 |
| AATCTTTGCT | GTATACTTTT | AAAAAATACT | CTGCTATTTC | TCTTGCTGGA | ACTGTTGAAA | 3302 |
| GAAAATATAT | AGAATGATCT | ATTGCTCATC | AGCTTTATTT | TTTAAACATA | CGACTTATTT | 3362 |
| TGTTGAAATT | GTCAAAGACT | GTATTTAGAT | CTCATAATGC | TTTGTTAAAT | GTTTACAAGT | 3422 |
| AAATAGTTTG | AATTCAGTAA | ATATTAAAAA | AAAA | | | 3456 |

( 2 ) INFORMATION FOR SEQ ID NO:25:

( i ) SEQUENCE CHARACTERISTICS:

(A) LENGTH: 870 amino acids
(B) TYPE: amino acid
(D) TOPOLOGY: linear (ii) MOLECULE TYPE: protein (xi) SEQUENCE DESCRIPTION: SEQ ID NO:25:

| | | | | | | | | | | | | | | |
|---|---|---|---|---|---|---|---|---|---|---|---|---|---|---|
| Met 1 | Lys | Gly | Trp | Tyr 5 | His | Gly | Lys | Leu | Asp 10 | Arg | Thr | Ile | Ala | Glu Glu 15 |
| Arg | Leu | Arg | Gln 20 | Ala | Gly | Lys | Ser | Gly 25 | Ser | Tyr | Leu | Ile | Arg 30 | Glu Ser |
| Asp | Arg | Arg 35 | Pro | Gly | Ser | Phe | Val 40 | Leu | Ser | Phe | Leu | Ser 45 | Gln | Met Asn |
| Val | Val 50 | Asn | His | Phe | Arg | Ile 55 | Ile | Ala | Met | Cys | Gly 60 | Asp | Tyr | Tyr Ile |
| Gly 65 | Gly | Arg | Arg | Phe | Ser 70 | Ser | Leu | Ser | Asp | Leu 75 | Ile | Gly | Tyr | Tyr Ser 80 |
| His | Val | Ser | Cys | Leu 85 | Leu | Lys | Gly | Glu | Lys 90 | Leu | Leu | Tyr | Pro | Val Ala 95 |
| Pro | Pro | Glu | Pro 100 | Val | Glu | Asp | Arg | Arg 105 | Arg | Val | Arg | Ala | Ile 110 | Leu Pro |
| Tyr | Thr | Lys 115 | Val | Pro | Asp | Thr | Asp 120 | Glu | Ile | Ser | Phe | Leu 125 | Lys | Gly Asp |
| Met | Phe 130 | Ile | Val | His | Asn | Glu 135 | Leu | Glu | Asp | Gly | Trp 140 | Met | Trp | Val Thr |
| Asn 145 | Leu | Arg | Thr | Asp | Glu 150 | Gln | Gly | Leu | Ile | Val 155 | Glu | Asp | Leu | Val Glu 160 |
| Glu | Val | Gly | Arg | Glu 165 | Glu | Asp | Pro | His | Glu 170 | Gly | Lys | Ile | Trp | Phe His 175 |
| Gly | Lys | Ile | Ser 180 | Lys | Gln | Glu | Ala | Tyr 185 | Asn | Leu | Leu | Met | Thr 190 | Val Gly |
| Gln | Val | Cys 195 | Ser | Phe | Leu | Val | Arg 200 | Pro | Ser | Asp | Asn | Thr 205 | Pro | Gly Asp |
| Tyr | Ser 210 | Leu | Tyr | Phe | Arg | Thr 215 | Asn | Glu | Asn | Ile | Gln 220 | Arg | Phe | Lys Ile |
| Cys 225 | Pro | Thr | Pro | Asn | Asn 230 | Gln | Phe | Met | Met | Gly 235 | Gly | Arg | Tyr | Tyr Asn 240 |
| Ser | Ile | Gly | Asp | Ile 245 | Ile | Asp | His | Tyr | Arg 250 | Lys | Glu | Gln | Ile | Val Glu 255 |
| Gly | Tyr | Tyr | Leu 260 | Lys | Glu | Pro | Val | Pro 265 | Met | Gln | Asp | Gln | Glu 270 | Gln Val |
| Leu | Asn | Asp 275 | Thr | Val | Asp | Gly | Lys 280 | Glu | Ile | Tyr | Asn | Thr 285 | Ile | Arg Arg |
| Lys | Thr 290 | Lys | Asp | Ala | Phe | Tyr 295 | Lys | Asn | Ile | Val | Lys 300 | Lys | Gly | Tyr Leu |
| Leu 305 | Lys | Lys | Gly | Lys | Gly 310 | Lys | Arg | Trp | Lys | Asn 315 | Leu | Tyr | Phe | Ile Leu 320 |
| Glu | Gly | Ser | Asp | Ala 325 | Gln | Leu | Ile | Tyr | Phe 330 | Glu | Ser | Glu | Lys | Arg Ala 335 |
| Thr | Lys | Pro | Lys 340 | Gly | Leu | Ile | Asp | Leu 345 | Ser | Val | Cys | Ser | Val 350 | Tyr Val |
| Val | His | Asp 355 | Ser | Leu | Phe | Gly | Arg 360 | Pro | Asn | Cys | Phe | Gln 365 | Ile | Val Val |
| Gln | His 370 | Phe | Ser | Glu | Glu | His 375 | Tyr | Ile | Phe | Tyr | Phe 380 | Ala | Gly | Glu Thr |

```
Pro  Glu  Gln  Ala  Glu  Asp  Trp  Met  Lys  Gly  Leu  Gln  Ala  Phe  Cys  Asn
385                      390                      395                      400

Leu  Arg  Lys  Ser  Ser  Pro  Gly  Thr  Ser  Asn  Lys  Arg  Leu  Arg  Gln  Val
                    405                      410                      415

Ser  Ser  Leu  Val  Leu  His  Ile  Glu  Glu  Ala  His  Lys  Leu  Pro  Val  Lys
                    420                      425                      430

His  Phe  Thr  Asn  Pro  Tyr  Cys  Asn  Ile  Tyr  Leu  Asn  Ser  Val  Gln  Val
               435                      440                      445

Ala  Lys  Thr  His  Ala  Arg  Glu  Gly  Gln  Asn  Pro  Val  Trp  Ser  Glu  Glu
     450                      455                      460

Phe  Val  Phe  Asp  Asp  Leu  Pro  Pro  Asp  Ile  Asn  Arg  Phe  Glu  Ile  Thr
465                      470                      475                      480

Leu  Ser  Asn  Lys  Thr  Lys  Lys  Ser  Lys  Asp  Pro  Asp  Ile  Leu  Phe  Met
                    485                      490                      495

Arg  Cys  Gln  Leu  Ser  Arg  Leu  Gln  Lys  Gly  His  Ala  Thr  Asp  Glu  Trp
               500                      505                      510

Phe  Leu  Leu  Ser  Ser  His  Ile  Pro  Leu  Lys  Gly  Ile  Glu  Pro  Gly  Ser
          515                      520                      525

Leu  Arg  Val  Arg  Ala  Arg  Tyr  Ser  Met  Glu  Lys  Ile  Met  Pro  Glu  Glu
     530                      535                      540

Glu  Tyr  Ser  Glu  Phe  Lys  Glu  Leu  Ile  Leu  Gln  Lys  Glu  Leu  His  Val
545                      550                      555                      560

Val  Tyr  Ala  Leu  Ser  His  Val  Cys  Gly  Gln  Asp  Arg  Thr  Leu  Leu  Ala
                    565                      570                      575

Ser  Ile  Leu  Leu  Arg  Ile  Phe  Leu  His  Glu  Lys  Leu  Glu  Ser  Leu  Leu
               580                      585                      590

Leu  Cys  Thr  Leu  Asn  Asp  Arg  Glu  Ile  Ser  Met  Glu  Asp  Glu  Ala  Thr
          595                      600                      605

Thr  Leu  Phe  Arg  Ala  Thr  Thr  Leu  Ala  Ser  Thr  Leu  Met  Glu  Gln  Tyr
     610                      615                      620

Met  Lys  Ala  Thr  Ala  Thr  Gln  Phe  Val  His  His  Ala  Leu  Lys  Asp  Ser
625                      630                      635                      640

Ile  Leu  Lys  Ile  Met  Glu  Ser  Lys  Gln  Ser  Cys  Glu  Leu  Ser  Pro  Ser
                    645                      650                      655

Lys  Leu  Glu  Lys  Asn  Glu  Asp  Val  Asn  Thr  Asn  Leu  Thr  His  Leu  Leu
               660                      665                      670

Asn  Ile  Leu  Ser  Glu  Leu  Val  Glu  Lys  Ile  Phe  Met  Ala  Ser  Glu  Ile
          675                      680                      685

Leu  Pro  Pro  Thr  Leu  Arg  Tyr  Ile  Tyr  Gly  Cys  Leu  Gln  Lys  Ser  Val
     690                      695                      700

Gln  His  Lys  Trp  Pro  Thr  Asn  Thr  Thr  Met  Arg  Thr  Arg  Val  Val  Ser
705                      710                      715                      720

Gly  Phe  Val  Phe  Leu  Arg  Leu  Ile  Cys  Pro  Ala  Ile  Leu  Asn  Pro  Arg
                    725                      730                      735

Met  Phe  Asn  Ile  Ile  Ser  Asp  Ser  Pro  Ser  Pro  Ile  Ala  Ala  Arg  Thr
               740                      745                      750

Leu  Ile  Leu  Val  Ala  Lys  Ser  Val  Gln  Asn  Leu  Ala  Asn  Leu  Val  Glu
          755                      760                      765

Phe  Gly  Ala  Lys  Glu  Pro  Tyr  Met  Glu  Gly  Val  Asn  Pro  Phe  Ile  Lys
     770                      775                      780

Ser  Asn  Lys  His  Arg  Met  Ile  Met  Phe  Leu  Asp  Glu  Leu  Gly  Asn  Val
785                      790                      795                      800

Pro  Glu  Leu  Pro  Asp  Thr  Thr  Glu  His  Ser  Arg  Thr  Asp  Leu  Ser  Arg
                    805                      810                      815
```

```
Asp Leu Ala Ala Leu His Glu Ile Cys Val Ala His Ser Asp Glu Leu
            820             825                 830

Arg Thr Leu Ser Asn Glu Arg Gly Ala Gln Gln His Val Leu Lys Lys
        835             840                 845

Leu Leu Ala Ile Thr Glu Leu Leu Gln Gln Lys Gln Asn Gln Tyr Thr
    850                 855                 860

Lys Thr Asn Asp Val Arg
865                 870
```

(2) INFORMATION FOR SEQ ID NO:26:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:26:

```
Val Lys Thr Ala Val Gln Glu Phe Gly Lys Leu Ala Pro Glu Lys
1               5                   10                  15

Lys Trp Lys
```

(2) INFORMATION FOR SEQ ID NO:27:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:27:

```
Lys Leu Arg Leu Leu Phe Arg Asn Leu Gly Ser Trp Leu Gln Lys Arg
1               5                   10                  15

Ser Gly Asn Glu Gly
                20
```